(12) United States Patent
Williams

(10) Patent No.: US 11,701,078 B2
(45) Date of Patent: *Jul. 18, 2023

(54) SYSTEMS AND METHODS FOR DETECTING COMPLEX NETWORKS IN MRI IMAGE DATA

(71) Applicant: The Board of Trustees of the Leland Stanford Junior University, Stanford, CA (US)

(72) Inventor: Leanne Maree Williams, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,388

(22) Filed: Jul. 6, 2020

(65) Prior Publication Data
US 2020/0397394 A1 Dec. 24, 2020

Related U.S. Application Data

(63) Continuation of application No. 16/368,774, filed on Mar. 28, 2019, now Pat. No. 10,702,232, which is a
(Continued)

(51) Int. Cl.
*A61B 6/00* (2006.01)
*G06T 3/00* (2006.01)
(Continued)

(52) U.S. Cl.
CPC .............. *A61B 6/501* (2013.01); *A61B 5/055* (2013.01); *A61B 5/165* (2013.01); *A61B 5/168* (2013.01);
(Continued)

(58) Field of Classification Search
CPC ... G06K 9/0014; G06T 3/0093; G06T 7/0014; G06T 2207/10088; G06T 2207/30016;
(Continued)

(56) References Cited

U.S. PATENT DOCUMENTS

| 5,938,688 A | 8/1999 | Schiff |
| 6,066,163 A | 5/2000 | John |

(Continued)

FOREIGN PATENT DOCUMENTS

| AT | 493932 T | 1/2011 |
| CN | 104207778 A | 12/2014 |

(Continued)

OTHER PUBLICATIONS

Schreibmann et al., 2015, "Automated population-based planning for whole brain radiation therapy" (pp. 76-86). (Year: 2015).*
(Continued)

*Primary Examiner* — Manav Seth
(74) *Attorney, Agent, or Firm* — KPPB LLP

(57) ABSTRACT

Systems and methods for detecting complex networks in MRI image data in accordance with embodiments of the invention are illustrated. One embodiment includes an image processing system, including a processor, a display device connected to the processor, an image capture device connected to the processor, and a memory connected to the processor, the memory containing an image processing application, wherein the image processing application directs the processor to obtain a time-series sequence of image data from the image capture device, identify complex networks within the time-series sequence of image data, and provide the identified complex networks using the display device.

20 Claims, 18 Drawing Sheets

Related U.S. Application Data continuation of application No. 15/997,631, filed on Jun. 4, 2018, now Pat. No. 10,285,658, which is a continuation of application No. 15/820,338, filed on Nov. 21, 2017, now Pat. No. 10,034,645.

(60) Provisional application No. 62/485,196, filed on Apr. 13, 2017, provisional application No. 62/563,611, filed on Sep. 26, 2017, provisional application No. 62/568,676, filed on Oct. 5, 2017, provisional application No. 62/589,452, filed on Nov. 21, 2017.

(51) Int. Cl.
| | |
|---|---|
| *G06T 7/00* | (2017.01) |
| *A61B 5/00* | (2006.01) |
| *A61B 5/16* | (2006.01) |
| *A61B 5/055* | (2006.01) |
| *G06V 20/69* | (2022.01) |
| *G06V 10/26* | (2022.01) |
| *G06V 10/34* | (2022.01) |

(52) U.S. Cl.
CPC .......... *A61B 5/4064* (2013.01); *A61B 5/4088* (2013.01); *G06T 3/0093* (2013.01); *G06T 7/0012* (2013.01); *G06T 7/0014* (2013.01); *G06T 7/0016* (2013.01); *G06V 20/695* (2022.01); *A61B 5/7267* (2013.01); *A61B 2576/026* (2013.01); *G06T 2207/10076* (2013.01); *G06T 2207/10088* (2013.01); *G06T 2207/10104* (2013.01); *G06T 2207/20076* (2013.01); *G06T 2207/20081* (2013.01); *G06T 2207/30016* (2013.01); *G06V 10/26* (2022.01); *G06V 10/34* (2022.01)

(58) Field of Classification Search
CPC ........ G06T 2207/20104; A61B 5/4064; A61B 5/165; A61B 5/4088; A61B 2034/2065; A61B 5/0022; A61B 6/037; A61B 6/501; A01K 2267/0312; G06F 19/3456

See application file for complete search history.

(56) References Cited

U.S. PATENT DOCUMENTS

| | | | |
|---|---|---|---|
| 6,167,311 A | 12/2000 | Rezai | |
| 6,198,958 B1 | 3/2001 | Ives et al. | |
| 6,272,370 B1 | 8/2001 | Gillies et al. | |
| 6,463,328 B1 | 10/2002 | John | |
| 6,539,263 B1 | 3/2003 | Schiff et al. | |
| 6,708,064 B2 | 3/2004 | Rezai | |
| 7,068,842 B2* | 6/2006 | Liang | A61B 5/1116 382/103 |
| 7,123,952 B2* | 10/2006 | Nakai | A61B 6/503 600/509 |
| 7,269,516 B2 | 9/2007 | Brunner et al. | |
| 7,338,455 B2 | 3/2008 | White et al. | |
| 7,565,193 B2 | 7/2009 | Laken | |
| 7,729,755 B2 | 6/2010 | Laken | |
| 8,014,847 B2* | 9/2011 | Shastri | A61B 5/055 600/545 |
| 8,090,164 B2 | 1/2012 | Bullitt et al. | |
| 8,861,815 B2* | 10/2014 | Cecchi | G16H 30/40 600/416 |
| 9,101,276 B2 | 8/2015 | Georgopoulos | |
| 9,501,829 B2 | 11/2016 | Carlton et al. | |
| 9,510,756 B2* | 12/2016 | Grady | A61B 5/055 |
| 10,006,978 B2* | 6/2018 | Hart | G06T 7/0016 |
| 10,034,645 B1* | 7/2018 | Williams | A61B 6/501 |
| 10,206,632 B2* | 2/2019 | Halter | G06T 7/0016 |
| 10,285,658 B2* | 5/2019 | Williams | G06T 7/0014 |
| 10,586,326 B2* | 3/2020 | Silbersweig | G06T 11/206 |
| 10,702,232 B2* | 7/2020 | Williams | G06V 20/64 |
| 2004/0059241 A1* | 3/2004 | Suffin | A61B 5/165 600/544 |
| 2007/0191704 A1 | 8/2007 | DeCharms | |
| 2009/0099623 A1* | 4/2009 | Bentwich | A61N 1/36025 607/45 |
| 2010/0191124 A1 | 7/2010 | Prokoski | |
| 2013/0231552 A1 | 9/2013 | Grady et al. | |
| 2013/0308860 A1* | 11/2013 | Mainali | G06V 10/757 382/199 |
| 2015/0018664 A1 | 1/2015 | Pereira et al. | |
| 2015/0272469 A1 | 10/2015 | Fox et al. | |
| 2016/0038049 A1 | 2/2016 | Geva et al. | |
| 2016/0379382 A1 | 12/2016 | Ishii et al. | |
| 2017/0188932 A1* | 7/2017 | Singer | A61B 5/369 |
| 2018/0325482 A1 | 11/2018 | Williams | |
| 2019/0282191 A1 | 9/2019 | Williams | |

FOREIGN PATENT DOCUMENTS

| | | |
|---|---|---|
| CN | 104605853 A | 5/2015 |
| CN | 110662490 A | 1/2020 |
| EP | 3606432 A1 | 2/2020 |
| JP | 06058913 U | 8/1994 |
| JP | 2015062817 A | 4/2015 |
| JP | 2015534856 A | 12/2015 |
| JP | 2017012480 A | 1/2017 |
| JP | 2020516372 A | 6/2020 |
| KR | 10-2019-0138821 A | 12/2019 |
| WO | 2016110358 A1 | 7/2016 |
| WO | 2016120869 A1 | 8/2016 |
| WO | 2018191685 A1 | 10/2018 |

OTHER PUBLICATIONS

Williams, Sep. 21, 2016, Defining biotypes for depression and anxiety based on large-scale circuit dysfunction: A theoretical review of the evidence and future directions for clinical translation (pp. 1-30). (Year: 2016).*
Siuly, "Medical Big Data: Neurological Diseases Diagnosis Through Medical Data Analysis", (pp. 54-64) (Year: 2016).*
Extended European Search Report for European Application No. 18784682.9, Search completed Mar. 20, 2020, dated Jun. 30, 2020, 13 Pgs.
International Preliminary Report on Patentability for International Application PCT/US2018/027606, Report dated Oct. 15, 2019, dated Oct. 24, 2019, 9 Pgs.
American Psychiatric Association, Diagnostic and Statistical Manual of Mental Disorders, American Psy. Also. Pub., Arlington, 4th Ed., 2000.
International Search Report and Written Opinion for International Application No. PCT/US2018/027606, Search completed Jun. 27, 2018, dated Aug. 23, 2018, 20 Pgs.
ISPOT-D, Retrieved from: http://williamspanlab.com/ispot-d, Printed on May 9, 2017.
Partial European Search Report for European Application No. 18784682.9, Search completed Mar. 20, 2020, dated Mar. 27, 2020, 15 Pgs.
Substance Abuse and Mental Health Services Administration, 2013, Results from the 2012 National Summary on Drug Use and Health: Mental Health Findings, Rockville, MD, 178 pgs.
"Basics of fMRI Analysis: Preprocessing, First Level Analysis, and Group Analysis", Massachusetts General Hospital, Harvard Medical School, Retrieved from https://ftp.nmr.mgh.harvard.edu/pub/docs/SavoyfMRI2014/fmri.april2011.pdf, Apr. 2011, Last modified Mar. 29, 2011, 69 pgs.
"FMRI Basics: Single subject analysis using the general linear model", University of Cambridge, MRC Cognition and Brain Sciences Unit, Retrieved from: http://imaging.mrc-cbu.cam.ac.uk/imaging/Introduction_to_fMRI_2010?action=AttachFile&do=get&target=Intro_fMRI_2010_02_GLM.pdf, 2010, 31 pgs.

(56) References Cited

OTHER PUBLICATIONS

"FMRIB Software Library v5.0", Analysis Group, FMRIB, Oxford, UK, FSL, Last edited by MarkJenkinson Nov. 25, 2017, Retrieved from https://fsl.fmrib.ox.ac.uk/fsl/fslwiki/, 1 pg.

"PPI—what and why (and how)", Nov. 17, 2008, 12 pgs.

Achaibou et al., "Distinct frontal and amygdala correlates of change detection for facial identity and expression", Social Cognitive and Affective Neuroscience, 2016, vol. 11, No. 2, pp. 225-233, advance access publication: Aug. 4, 2015.

Adamson et al., "An improved brief measure of cannabis misuse: The Cannabis Use Disorders Identification Test—Revised (CUDIT-R)", Drug and Alcohol Dependence, Mar. 2010, vol. 110, pp. 137-143.

Afzali et al., "A network approach to the comorbidity between posttraumatic stress disorder and major depressive disorder: The role of overlapping symptoms", Journal of Affective Disorders, Jan. 15, 2017, available online Oct. 25, 2019, vol. 208, pp. 490-496.

Aizenstein et al., "Altered Functioning of the Executive Control Circuit in Late-Life Depression: Episodic and Persistent Phenomena", Am. J. Geriatr. Psychiatry, Jan. 2009, vol. 17, No. 1, pp. 30-42.

Aizenstein et al., "Altered Functioning of the Executive Control Circuit in Late-Life Depression: Episodic and Persistent Phenomena", NIH Public Access—Author Manuscript, 20 pgs.—Am. J. Geriatr. Psychiatry, Jan. 2009, vol. 17, No. 1, pp. 30-42.

Alexopoulos et al., "Functional Connectivity in the cognitive control network and the default mode network in late-life depression", Journal of Affective Disorders, Mar. 2012, vol. 139, pp. 56-65.

Almeida et al., "Elevated Amygdala Activity to Sad Face Expressions: A State Marker of Bipolar but Not Unipolar Depression", NIH Public Access—author manuscript, 18 pgs., published in final form as Biol. Psychiatry, Mar. 1, 2010, vol. 67, No. 5, pp. 414-421, doi.10.1016/j.biopsych.2009.09.027.

Almeida et al., "Elevated Amygdala Activity to Sad Facial Expressions: A State Marker of Bipolar but Not Unipolar Depression", Biol. Psychiatry, Mar. 2010, vol. 67, Issue 5, pp. 414-421.

Andersson et al., "Non-linear optimisation", FMRIB Technical Report TR07JA1, Jun. 28, 2007, 17 pgs.

Andersson et al., "Non-linear registration aka Spatial normalisation", FMRIB Technical Report TR04JA2, Jun. 28, 2007, 22 pgs.

Andreescu et al., "Resting state functional connectivity and treatment response in late-life depression", Psychiatry Research: Neuroimaging, Oct. 2013, vol. 214, pp. 313-321.

Anteraper et al., "Hyper-Connectivity of Subcortical Resting-State Networks in Social Anxiety Disorder", Brain Connectivity, 2014, vol. 4, No. 2, pp. 81-90.

Anticevic et al., "The role of default network deactivation in cognition and disease", Trends in Cognitive Sciences, Dec. 2012, vol. 16, No. 12, pp. 584-592.

Anticevic et al., "When less is more: TPJ and default network deactivation during encoding predicts working memory performance", NeuroImage, Feb. 1, 2010, available online Nov. 12, 2009, vol. 49, Issue 3, pp. 2638-2648.

Arato et al., "Elevated CSF CRF in Suicide Victims", Biol. Psychiatry, Feb. 1, 1989, vol. 25, Issue 3, pp. 355-359.

Arlt et al., "Genetic Risk Factors for Depression in Alzheimer's Disease Patients", Current Alzheimer Research, 2013, vol. 10, pp. 72-81.

Arnone et al., "Increased Amygdala Responses to Sad But Not Fearful Faces in Major Depression: Relation to Mood State and Pharmacological Treatment", American Journal Psychiatry, Aug. 2012, vol. 169, No. 8, pp. 841-850.

Asarnow et al., "Treatment of Selective Serotonin Reuptake Inhibitor-Resistant Depression in Adolescents: Predictors and Moderators of Treatment Response", Journal of the American Academy of Child and Adolescent Psychiatry, Mar. 2009, vol. 48, No. 3, pp. 330-339.

Ashburner et al., "SPM8 Manual", Functional Imaging Laboratory, Wellcome Trust Centre for Neuroimaging, Feb. 4, 2013, Retrieved from: www.fil.ion.ucl.ac.uk/spm/doc/spm8_manual.pdf, 475 pgs.

Ashburner et al., "Unified segmentation", NeuroImage, 2005, vol. 26, available online Apr. 1, 2005, pp. 839-851.

Auerbach et al., "Emotion processing biases and resting EEG activity in depressed adolescents", HHS Public Access—Author manuscript, 18 pgs., published in final form as Depress Anxiety, Sep. 2015, vol. 32, No. 9, pp. 693-701, doi:10.1002/da.22381.

Austin et al., "Cognitive deficits in depression", British Journal of Psychiatry, 2001, vol. 178, pp. 200-206.

Austin et al., "Cognitive function in major depression", Journal of Affective Disorders, 1992, vol. 25, pp. 21-30.

Austin et al., "Effect of apomorphine on motor and cognitive function in melancholic patients: a preliminary report", Psychiatry Research, 2000, vol. 97, pp. 207-215.

Baca et al., "Gender differences in treatment response to sertraline versus imipramine in patients with nonmelancholic depressive disorders", Progress in Neuro-Psychopharmacology & Biological Psychiatry, 2004, vol. 28, pp. 57-65.

Bachmeier et al., "Effect of Venlafaxine and Desvenlafaxine on Drug Efflux Protein Expression and Biodistribution In Vivo", Journal of Pharmaceutical Sciences, 2013, vol. 102, pp. 3838-3843.

Ball et al., "Quantifying person-level brain network functioning to facilitate clinical translation", Translational Psychiatry, No. 7, Published online Oct. 17, 2017, 8 pgs.

Banki et al., "CSF Corticotropin-Releasing Factor-Like Immunoreactivity in Depression and Schizophrenia", Am. J. Psychiatry, Jul. 1987, vol. 144, No. 7, pp. 873-877.

Barbe et al., "Lifetime History of Sexual Abuse, clinical Presentation, and Outcome in a Clinical Trial for Adolescent Depression", J Clin. Psychiatry, Jan. 2004, vol. 65, pp. 77-83.

Barch et al., "Function in the human connectome: Task-fMRI and individual differences in behavior", NeuroImage, 2013, vol. 80, pp. 169-189.

Barch et al., "Selecting Paradigms From Cognitive Neuroscience for Translation into Use in Clinical Trials: Proceedings of the Third CNTRICS Meeting", Schizophrenia Bulletin, 2009, Advance Access publication Nov. 20, 2008, vol. 35, No. 1, pp. 109-114.

Barrett et al., "Haploview: analysis and visualization of LD and haplotype maps", Bioinformatics, 2005, Advance Access publication Aug. 5, 2004, vol. 21, No. 2, pp. 263-265.

Bartova et al., "Reduced default mode network suppression during a working memory task in remitted major depression", Journal of Psychiatric Research, 2015, vol. 64, pp. 9-18.

Baum et al., "Heightened Susceptibility Traumatization: A Meta-Analysis of Gender Differences", American Journal of Orthopsychiatry, vol. 2014, vol. 84, No. 2, pp. 111-122.

Baxter et al., "Global prevalence of anxiety disorders: a systematic review and meta-regression", Psychological Medicine, 2013, published online Jul. 10, 2012, vol. 43, pp. 897-910.

Beaudreau et al., "Late-Life anxiety and Cognitive Impairment: A Review", American Journal Geriatric Psychiatry, Oct. 2008, vol. 16, No. 10, pp. 790-803.

Beck et al., "An Inventory for Measuring Clinical Anxiety: Psychometric Properties", Journal of Consulting and Clinical Psychology, 1988, vol. 56, No. 6, pp. 893-897.

Becker-Lausen et al., "Mediation of Abusive Childhood Experiences: Depression, Dissociation, and Negative Life Outcomes", Amer. J. Orthopsychiatry, Oct. 1995, vol. 65, No. 4, pp. 560-573.

Behan et al., "Corticotropin-Releasing Factor (CRF), CRF-Binding Protein (CRF-BP, and CRF/CRF-BP Complex in Alzheimer's Disease and Control Postmortem Human Brain", Journal of Neurochemistry, 1997, vol. 68, pp. 2053-2060.

Belzung et al., "Depression: from psychopathology to pathophysiology", Current Opinion in Neurobiology, 2015, vol. 30, pp. 24-30.

Bernet et al., "Relationship of Childhood Maltreatment to the Onset and Course of Major Depression in Adulthood", Depression and Anxiety, 1999, vol. 9, pp. 169-174.

Berridge et al., "Affective neuroscience of pleasure: reward in humans and animals", NIH Public Access—Author Manuscript, 39 pgs., Psychopharmacology (Berl), Aug. 2008, vol. 199, No. 3, pp. 457-480, dio: 10.1007/s00213-008-1099-6.

Berry et al., "A randomised controlled trial to compare opt-in and opt-out parental consent for childhood vaccine safety surveillance using data linkage study protocol", Trials, 2011, vol. 12, No. 1, pp. 1-10.

(56) References Cited

OTHER PUBLICATIONS

Binder et al., "Association of Polymorphisms in Genes Regulating the Corticotropin-Releasing Factor System with Antidepressant Treatment Response", Archives of General Psychiatry, Apr. 2010, published online Dec. 15, 2009, vol. 67, No. 4, pp. 369-379.
Binder et al., "The CRF system, stress, depression and anxiety-insights from human genetic studies", Molecular Psychiatry, 2010, vol. 15, pp. 574-588.
Biswal et al., "Simultaneous Assessment of Flow and BOLD Signals in Resting-State Functional Connectivity Maps", NMR in Biomedicine, 1997, vol. 10, pp. 165-170.
Biswal et al., "Toward discovery science of human brain function", Proc. Nat. Acad. Sci., 107, 2010, pp. 4734-4739.
Blair et al., "Reduced Dorsal Anterior Cingulate Cortical Activity During Emotional Regulation and Top-Down Attentional Control in Generalized Social Phobia, Generalized Anxiety Disorder, and Comorbid Generalized Social Phobia/Generalized Anxiety Disorder", Biol. Psychiatry, 2012, vol. 72, pp. 476-482.
Blair et al., "Response to Emotional Expressions in Generalized Social Phobia and Generalized Anxiety Disorder: Evidence for Separate Disorders", Am. J. Psychiatry, Sep. 2008, vol. 165, pp. 1193-1202.
Blake et al., "The Development of a Clinician-Administered PTSD Scale", Journal of Traumatic Stress, 1995, vol. 8, No. 1, pp. 75-90.
Blanchard et al., "Psychometric Properties of the PTSD Checklist (PCL)", Behav. Res. Then, 1996, vol. 34, No. 8, pp. 669-673.
Blugeot et al., "Vulnerability to Depression: From Brain Neuroplasticity to Identification of Biomarkers", The Journal of Neuroscience, Sep. 7, 2011, vol. 31, No. 36, pp. 12889-12899.
Boebinger et al., "Introduction to Connectivity: resting-state and PPI", UCL, Methods for Dummies 2012-2013, 47 pgs.
Boone et al., "Factor Analysis of Four Measures of Prefrontal Lobe Functioning", Archives of Clinical Neuropsychology, 1998, vol. 13, No. 7, pp. 585-595.
Boyle et al., "Annotation of functional variation in personal genomes using RegulomeDB", Genome Research 22:1790-1797, Sep. 2012.
Bracht et al., "White matter microstructure alterations of the medial forebrain bundle in melancholic depression", Journal of Affective Disorders, 2014, vol. 155, pp. 186-193, available online Nov. 5, 2013.
Brassen et al., "Ventromedial Prefrontal Cortex Processing During Emotional Evaluation In Late-Life Depression: A Longitudinal Functional Magnetic Resonance Imaging Study", Biol. Psychiatry, 2008, vol. 64, pp. 349-355.
Brett et al., "Region of interest analysis using an SPM toolbox (Abstract)", 8th International Conference on Functional Mapping of the human Brain, Jun. 2-6, 2002, 1 pg.
Brodersen et al., "Dissecting psychiatric spectrum disorders by generative embedding", NeuroImage: Clinical, 2014, available online Nov. 16, 2013, vol. 4, pp. 98-111.
Broen et al., "Factor analysis of the Hamilton Depression Rating Scale in Parkinson's Disease", Parkinsonism and Related Disorders, Feb. 2015, vol. 21, Issue 2, pp. 142-146.
Browning et al., "The modification of attentional bias to emotional information: A review of the techniques, mechanisms, and relevance to emotional disorders", Cognitive, Affective, & Behavioral Neuroscience, 2010, vol. 10, No. 1, pp. 8-20.
Broyd et al., "Default-mode brain dysfunction in mental disorders: A systematic review", Neuroscience and Biobehavioral Reviews, 2009, vol. 33, pp. 279-296.
Bruce et al., "Altered emotional interference processing in the amygdala and insula in women with Post-Traumatic Stress Disorder", NeuroImage: Clinical, 2013, available online Nov. 13, 2012, vol. 2, pp. 43-49.
Bruder et al., "Neurocognitive Predictors of Antidepressant Clinical Response", J. Affect Disorder, Sep. 2014, vol. 166, pp. 108-114.
Bryant et al., "Enhanced Amygdala and Medial Prefrontal Activation During Nonconscious Processing of Fear in Posttraumatic Stress Disorder: an fMRI Study", Human Brain Mapping, 2008, vol. 29, pp. 517-523, published online May 24, 2007.

Buckner et al., "Opportunities and limitations of intrinsic functional connectivity MRI", Nature Neuroscience, Jul. 2013, vol. 16, No. 7, pp. 832-837, published online Jun. 25, 2013.
Buckner et al., "The Brain's Default Network", Annals of the New York Academy of Science, 2008, vol. 1124, pp. 1-38.
Bullmore et al., "Complex brain networks: graph theoretical analysis of structural and functional systems", Reviews, Mar. 2009, vol. 10, pp. 186-198.
Burt et al., "Depression and Memory Impairment: A Meta-Analysis of the Association, Its Pattern and Specificity", Psychological Bulletin, 1995, vol. 117, No. 2, pp. 285-305.
Calhoun et al., "A Method for Making Group Inferences from Functional MRI Data Using Independent Component Analysis", Human Brain Mapping, 2001, vol. 14, pp. 140-151.
Calinski et al., "A dendrite method for cluster analysis", Communications in Statistics—Theory and Methods, 1974, vol. 3, No. 1, pp. 1-27, published online Jun. 27, 2007.
Camardese et al., "Imaging studies on dopamine transporter and depression: A review of literature and suggestions for future research", Journal of Psychiatric Research, 2014, vol. 51, pp. 7-18.
Cannistraro et al., "Amygdala Responses to Human Faces in Obsessive-Compulsive Disorder", Biol. Psychiatry, 2004, vol. 56, pp. 916-920.
Carlson et al., "A Left Amygdala Mediated Network for Rapid Orienting to Masked Fearful Faces", Neuropsychologia, May 2009, available Jan. 39, 2009, vol. 47, pp. 1386-1389.
Carroll et al., "Urinary free cortisol excretion in depression", Psychological Medicine, Mar. 1976, vol. 6, pp. 43-50.
Carstensen et al., "Package 'Epi'—A Package for Statistical Analysis in Epidemiology", Version 2.24, Jan. 27, 2018, 159 pgs.
Carvalho et al., "High-Dimensional Sparse Factor Modeling: Applications in Gene Expression Genomics", J. Am. Stat. Assoc., Dec. 1, 2008, vol. 103, No. 484, pp. 1438-1456.
Carver et al., "Assessing Coping Strategies: A Theoretically Based Approach", Journal of Personality and Social Psychology, 1989, vol. 56, No. 2, pp. 267-283.
Castelli et al., "Movement and Mind: A Functional Imaging Study of Perception and Interpretation of Complex Intentional Movement Patterns", NeuroImage, 2000, vol. 12, pp. 314-325.
Castro et al., "Role of the Amygdala in Antidepressant Effects on Hippocampal Cell Proliferation and Survival and on Depression-like Behavior in the Rat", PLoS one, Jan. 8, 2010, vol. 5, Issue 1, e8618, pp. 1-11.
Chang et al., "Reduction of dorsolateral prefrontal cortex gray matter in late-life depression", NIH Public Access, 15 pgs., Psychiatry Res. 2011, Jul. 30, 2011, vol. 198, No. 1.
Chattarji et al., "Neighborhood matters: divergent patterns of stress-induced plasticity across the brain", Nature Neuroscience, Oct. 2015, published online Sep. 25, 2015, vol. 18, No. 10, pp. 1364-1375.
Chen et al., "Causal interactions between fronto-parietal central executive and default-mode networks in humans", PNAS, Dec. 3, 2013, vol. 110, No. 49, pp. 19944-19949.
Chen et al., "Functional coupling of the amygdala in depressed patients treated with antidepressant medication", Neuropsychopharmacology, vol. 33, 2008, pp. 1909-1918.
Chinn et al., "ABCB1 Pharmacogenetics: Progress, Pitfalls, and Promise", Clinical Pharmacology & Therapeutics, Feb. 2007, vol. 81, No. 2, pp. 265-269.
Chu et al., "Early life trauma predicts self-reported levels of depressive and anxiety symptoms in nonclinical community adults: Relative contributions of early life stressor types and adult trauma exposure", Journal of Psychiatric Research, 2013, vol. 47, pp. 23-32.
Claes et al., "The Corticotropin-Releasing Hormone Binding Protein Is Associated with Major Depression in a Population from Northern Sweden", Biol. Psychiatry, 2003, vol. 54, pp. 867-872.
Clark et al., "Standardized assessment of cognitive functioning during development and aging using an automated touchscreen battery", Archives of Clinical Neuropsychology, Nov. 2006, vol. 21, pp. 449-467.

(56) References Cited

OTHER PUBLICATIONS

Clauss et al., "Neurocircuitry Underlying Risk and Resilience to Social Anxiety Disorder", Depression and Anxiety, 2014, vol. 31, pp. 822-833.
Clementz et al., "Identification of Distinct Psychosis Biotypes Using Brain-Based Biomarkers", Am. J. Psychiatry, Apr. 2016, vol. 173, pp. 373-384.
Cole et al., "Advances and Pitfalls in the Analysis and Interpretation of Resting-State FMRI Data", Frontiers in Systems Neuroscience, published online Apr. 6, 2010, prepublished online Feb. 28, 2010, vol. 4, No. 8, printed Apr. 1, 2017 from https://www.ncbi.nlm.nih.gov/pmc/articles/PMC2854531, 25 pgs.
Cole et al., "Advances and pitfalls in the analysis and interpretation of resting-state FMRI data", Frontiers in Systems Neuroscience, Review Article, published Apr. 6, 2010, Apr. 2010, vol. 4, Article 8, pp. 1-15.
Cole et al., "Intrinsic and Task-Evoked Network Architectures of the Human Brain", Neuron, Jul. 2, 2014, vol. 83, pp. 238-251.
Cole et al., "The cognitive control network: Integrated cortical regions with dissociable functions", NeuroImage, 2007, vol. 37, pp. 343-360.
Connolly et al., "Resting-State Functional Connectivity of Subgenual Anterior Cingulate Cortex in Depressed Adolescents", NIH Public Access—Author manuscript, 22 pgs., published in final form as: Biol. Psychiatry, Dec. 15, 2013, vol. 74, No. 12, pp. 898-907, doi:10.1016/j.biopsych.2013.05.036.
Corbetta et al., "Control of goal-directed and stimulus-driven attention in the brain", Nat. Rev. Neursci, vol. 3, No. 3, 2002, pp. 201-215.
Corbetta et al., "The reorienting system of the human brain: from environment to theory of mind", Neuron, vol. 58, No. 3, 2008, pp. 306-324.
Corrigan et al., "Comparison of Pramipexole, Fluoxetine, and Placebo in Patients with Major Depression", Depression and Anxiety, 2000, vol. 11, pp. 58-65.
Costa Dias et al., "Characterizing heterogeneity in children with and without ADHD based on reward system connectivity", Developmental Cognitive Neuroscience, Feb. 2015, vol. 11, pp. 155-174.
Costafreda et al., "Predictors of amygdala activation during the processing of emotional stimuli: A meta-analysis of 385 PET and fMRI studies", Brain Research Reviews, 2008, available online Nov. 12, 2007, vol. 58, pp. 57-70.
Craske et al., "What Is An Anxiety Disorder?", Depression and Anxiety, 2009, vol. 26, pp. 1066-1085.
Crawford et al., "The Depression Anxiety Stress Scales (DASS): Normative data and latent structure in a large non-clinical sample", British Journal of Clinical Psychology, 2003, vol. 42, pp. 111-131.
Crittenden et al., "Recruitment of the default mode network during a demanding act of executive control", eLife, 4, 2015, e06481, 12 pgs.
Crowther et al., "Resting-State Connectivity Predictors of Response to Psychotherapy in Major Depressive Disorder", Neuropsychopharmacology, Jan. 2015, vol. 40, No. 7, pp. 1659-1673.
Cui et al., "Functional Magnetic Resonance Imaging Connectivity Analyses Reveal Efference-Copy to Primary Somatosensory Area, BA2", PLOS One, Jan. 8, 2014, Retrieved from: http://journals.plos.org/plosone/article?id=10.1371/journal.pone.0084367, 12 pgs.
Cullen et al., "A preliminary study of functional connectivity in comorbid adolescent depression", Neuroscience Letters, Jun. 2009, vol. 460, pp. 227-231.
Cuthbert et al., "Toward the future of psychiatric diagnosis: the seven pillars of RDoC", BMC Medicine, 2013, vol. 11, No. 126, pp. 1-8.
Czeh et al., "Animal models of major depression and their clinical implications", Progress in Neuro-Psychopharmacology & Biological Psychiatry, 2016, available online Apr. 17, 2015, vol. 64, pp. 293-310.
Damoiseaux et al., "Consistent resting-state networks across healthy subjects", PNAS, Sep. 12, 2006, vol. 103, No. 37, pp. 13848-13853.

Danese et al., "Adverse Childhood Experiences and Adult Risk Factors for Age-Related Disease", Arch. Pediatr. Adolesc. Med., Dec. 2009, vol. 163, No. 12, pp. 1135-1143.
Daniels et al., "Switching between executive and default mode networks in posttraumatic stress disorder: alterations in functional connectivity", J. Psychiatry Neuroscience, 2010, vol. 35, No. 4, pp. 258-266.
Dannlowski et al., "Childhood Maltreatment is Associated with an Automatic Negative Emotion Processing Bias in the Amygdala", Human Brain Mapping, 2013, vol. 34, pp. 2899-2909.
Dannlowski et al., "Limbic Scars: Long-Term Consequences of Childhood Maltreatment Revealed by Functional and Structural Magnetic Resonance Imaging", Biol. Psychiatry, 2012, vol. 71, pp. 286-293.
Davidson, "Affective Neuroscience and Psychophysiology: Toward a synthesis", Psychophysiology, 2003, vol. 40, pp. 655-665.
Davidson, "Anterior electrophysiological asymmetries, emotion, and depression: Conceptual and methodological conundrums", Psychophysiology, 1998, vol. 35, pp. 607-614.
Davidson, "Anxiety and Affective Style: Role of Prefrontal Cortex and Amygdala", Biol. Psychiatry, 2002, vol. 51, pp. 68-80.
Davidson et al., "Social influences of neuroplasticity: stress and interventions to promote well-being", Nature Neuroscience, May 2012, published online Apr. 15, 2012, vol. 15, No. 5, pp. 689-695.
Day et al., "Cognitive and emotional biomarkers of melancholic depression: An iSPOT-D report", Journal of Affective Disorders, No. 176, 2015, Published online Feb. 7, 2015, pp. 141-150.
Day et al., "Impairment and distress patterns distinguishing the melancholic depression subtype: An iSPOT-D report", Journal of Affective Disorders, 2015, vol. 174, pp. 493-502, available online Nov. 7, 2014.
De Kwaasteniet et al., "Decreased resting-state connectivity between neurocognitive networks in treatment resistant depression", Frontiers in Psychiatry, Mar. 2, 2015, vol. 6, Article 28, pp. 1-8.
De Vries et al., "Compensatory Frontoparietal Activity During Working Memory: An Endophenotype of Obsessive-Compulsive Disorder", Biol. Psychiatry, Dec. 2014, vol. 76, pp. 878-887.
Debattista et al., "Pramipexole Augmentation of a Selective Serotonin Reuptake Inhibitor in the Treatment of Depression", Journal of Clinical Psychopharmacology, Apr. 2000, vol. 20, No. 2, p. 274-275, printed from https://ovidsp.tx.ovid.com/sp-3.28.0a/ovidweb.cgi, 3 pgs.
Debellis et al., "Association of Fluoxetine Treatment with Reductions in CSF Concentrations of Corticotropin-Releasing Hormone and Arginine Vasopressin in Patients with Major Depression", American Journal of Psychiatry, Apr. 1993, vol. 150, No. 4, pp. 656-657.
Deblaere et al., "Developing a comprehensive presurgical functional MRI protocol for patients with intractable temporal lobe epilepsy: a pilot study", Neuroradiology, 2002, vol. 44, pp. 667-673.
Dedovic et al., "Psychological, endocrine, and neural correlates of attentional bias in subclinical depression", Ann. Depress Anxiety, Sep. 18, 2014, vol. 1, Issue 4, 14 pgs.
Deklerk et al., "ABCB1 gene variants influence tolerance to selective serotonin reuptake inhibitors in a large sample of Dutch cases with major depressive disorder", The Pharmacogenomics Journal 2013, published online May 29, 2012, vol. 13, pp. 349-353.
Delaneau et al., "A linear complexity phasing method for thousands of genomes", Nature Methods, Feb. 2012, published online Dec. 4, 2011, vol. 9, No. 2, 6 pgs.
Den Hollander-Gusman et al., "Distinguishing symptom dimensions of depression and anxiety: An integrative approach", Journal of Affective Disorders, 2012, available online Nov. 1, 2011, No. 136, pp. 693-701.
Dept. of Health & Human Services, "Results from the 2012 National Survey on Drug Use and Health: Summary of National Findings", Sep. 2013, 178 pgs.
Der-Avakian et al., "Assessment of reward responsiveness in the response bias probabilistic reward task in rats: implications for cross-species translation research", Trans. Psychiatry, 2013, vol. 3, e297, pp. 1-8.
Dichter et al., "A Systematic Review of Relations between Resting-State Functional-MRI and Treatment Response in Major Depressive

(56) References Cited

OTHER PUBLICATIONS

Disorder", HHS Public Access—Author Manuscript, 21 pgs., published in final form as J. Affect. Disord., Feb. 1, 2015, vol. 172, pp. 8-17, doi:10.1016/j.jad.2014.09.028.
Dichter et al., "A systematic review of relations between resting-state functional-MRI and treatment response in major depressive disorder", Journal of Affective Disorders, 2015, available online Sep. 26, 2014, vol. 172, pp. 8-17.
Dichter et al., "Remitted major depression is characterized by reward network hyperactivation during reward anticipation and hypoactivation during reward outcomes", Journal of Affective Disorders, 2012, available online Oct. 28, 2011, vol. 136, pp. 1126-1134.
Diener et al., "The Satisfaction with Life Scale", Journal of Personality Assessment, 1985, vol. 49, No. 1, pp. 71-75.
Dong et al., "Sequence variations of ABCB1, SLC6A2, SLC6A3, SLC6A4, CREB1, CHRH1 and NTRL2: association with major depression and antidepressant response in in Mexican-Americans", Molecular Psychiatry, 2009, vol. 14, pp. 1105-1118.
Doshi-Velez et al., "Comorbidity Clusters in Autism Spectrum Disorders: An Electronic Health Record Time-Series Analysis", Pediatrics, Jan. 2014, vol. 133, pp. e54-e63.
Drevets et al., "Functional anatomical correlates of antidepressant drug treatment assessed with PET measures of regional glucose metabolism", European Neuropsychopharmacology, Dec. 2002, vol. 12, Issue 6, pp. 527-544.
Drevets et al., "Subgenual prefrontal cortex abnormalities in mood disorders", Nature, 386, 1997, pp. 824-822.
Drysdale et al., "Resting-state connectivity biomarkers define neurophysiological subtypes of depression", HHS Public Access—Author Manuscript, 35 pgs., published in final form as Nat. Med, Jan. 2017, vol. 23, No. 1, pp. 28-38, doi:10.1038/nm.4246.
Drysdale et al., "Resting-state connectivity biomarkers define neurophysiological subtypes of depression", Nature Medicine, No. 23, 2017, pp. 28-38, Published online Dec. 5, 2016, printed Mar. 21, 2017 from http://www.nature.com/nm/journal/v23/n1/full/nm.4246.html, 5 pgs.
Dube et al., "Long-Term Consequences of Childhood Sexual Abuse by Gender of Victim", American Journal of Preventive Medicine, 2005, vol. 29, No. 5, pp. 430-438.
Dubois et al., "Building a Science of Individual Differences from fMRI", Trends in Cognitive Sciences, Jun. 2016, vol. 20, No. 6, pp. 425-443.
Dunkin et al., "Executive dysfunction predicts nonresponse to fluoxetine in major depression", Journal of Affective Disorders, 2000. vol. 60, pp. 13-23.
Dunlop et al., "Effects of Patient Preferences on Outcomes in the Predictors of Remission in Depression to Individual and Combined Treatments (PReDICT) Study", Am. J. Psychiatry, Jun. 2017, vol. 174, No. 6, pp. 546-556.
Dunlop et al., "Functional Connectivity of the Subcallosal Cingulate Cortex and Differential Outcomes to Treatment with Cognitive-Behavioral Therapy of Antidepressant Medication for Major Depressive Disorder", Am. J. Psychiatry, Jun. 1, 2017, vol. 174, No. 6, pp. 533-545.
Dunlop et al., "Neuroimaging-based biomarkers for treatment selection in major depressive disorder", Dialogues in Clinical Neuroscience, 2014, vol. 16, No. 4, pp. 479-490.
Dunlop et al., "Preliminary Findings Supporting Insula Metabolic activity as a Predictor of Outcome to Psychotherapy and Medication Treatments for Depression", J. Neuropsychiatry Clin. Neuroscience, Summer 2015, vol. 27, pp. 237-239.
Dunlop et al., "The Role of Dopamine in the Pathophysiology of Depression", Arch. Gen. Psychiatry, Mar. 2007, vol. 64, pp. 327-337.
Egner et al., "Dissociable Neural Systems Resolve Conflict from Emotional versus Nonemotional Distracters", Cerebral Cortex, Jun. 2008, vol. 18, pp. 1475-1484.
Egner Lab, "Functional Connectivity: Psychophysiological Interaction (PPI) and Residual Correlation Analyses", Retrieved from: https://wiki.biac.duke.edu/lib/exe/fetch.php?media=biac:methods_journal_club:egner_functional_connectivity_talk.pdf, Mar. 25, 2013, 6 pgs.
Elliott, "The neuropsychological profile in unipolar depression", Trends in Cognitive Sciences, Nov. 1998, vol. 2, No. 11, pp. 447-454.
Elliott et al., "Abnormal response to negative feedback in unipolar depression: evidence for a diagnosis specific impairment", Journal of Neurology, Neurosurgery, and Psychiatry, 1997, vol. 63, pp. 74-82.
Elliott et al., "Prefrontal dysfunction in depressed patients performing a complex planning task: a study using positron emission tomography", Psychological Medicine, 1997, vol. 27, pp. 931-942.
Elliott et al., "The Neural Basis of Mood-Congruent Processing Biases in Depression", Arch. Gen. Psychiatry, 2002, vol. 59, pp. 597-604.
Etkin et al., "A Cognitive-Emotional Biomarker for Predicting Remission with Antidepressant Medications: A Report from the iSPOT-D Trial", Neuropsychopharmacology, 2015, vol. 40, pp. 1332-1342.
Etkin et al., "Disrupted Amygdala Subregion Functional Connectivity and Evidence of a Compensatory Network in Generalized Anxiety Disorder", Arch. Gen. Psychiatry, 2009, vol. 66, No. 12, pp. 1361-1372.
Etkin et al., "Failure of Anterior Cingulate Activation and Connectivity with the Amygdala During Implicit Regulation of Emotional Processing in Generalized Anxiety Disorder", Am. J. Psychiatry, 2010, vol. 167, pp. 545-554.
Etkin et al., "Functional Neuroimaging of Anxiety: A Meta-Analysis of Emotional Processing in PTSD, Social Anxiety Disorder, and Specific Phobia", Am. J. Psychiatry, 2007, vol. 164, pp. 1476-1488.
Etkin et al., "Individual Differences in Trait Anxiety Predict the Response of the Basolateral Amygdala to Unconsciously Processed Fearful Faces", Neuron, Dec. 16, 2004, vol. 44, pp. 1043-1055.
Etkin et al., "Resolving Emotional Conflict: A Role for the Rostral Anterior Cingulate Cortex in Modulating Activity in the Amygdala", Neuron, Sep. 21, 2006, vol. 51, pp. 871-882.
Exner et al., "Impaired implicit learning and reduced pre-supplementary motor cortex size in early-onset major depression with melancholic features", Journal of Affective Disorders, 2009, 119, pp. 156-162.
Eysenck et al., "Anxiety and Cognitive Performance: Attentional Control Theory", Emotion, 2007, vol. 7, No. 2, pp. 336-353.
Fair et al., "A method for using blocked and event-related fMRI data to study "resting state" functional connectivity", NeuroImage, 2007, vol. 35, pp. 396-405.
Falconer et al., "Inhibitory Neural Activity Predicts Response to Cognitive-Behavioral Therapy for Posttraumatic Stress Disorder", J. Clin. Psychiatry, 2013, vol. 74, No. 9, pp. 895-901.
Falconer et al., "The neural networks of inhibitory control in posttraumatic stress disorder", J. Psychiatry Neurosci., 2008, vol. 33, No. 3, pp. 413-422.
Fales et al., "Antidepressant treatment normalizes hypoactivity in dorsolateral prefrontal cortex during emotional interference processing in major depression", Journal of Affective Disorders, 2009, available online Jun. 17, 2008, vol. 112, pp. 206-211.
Fales et al., "Anxiety and cognitive efficiency: Differential modulation of transient and sustained neural activity during a working memory task", Cognitive, Affective, & Behavioral Neuroscience, 2008, vol. 8, No. 3, pp. 239-253.
Feldman et al., "Change in emotional processing during a dialectical behavior therapy-based skills group for major depressive disorder", Behaviour Research and Therapy, 2009, vol. 47, pp. 316-321.
Felleman et al., "Distributed Hierarchical Processing in the Primate Cerebral Cortex", Cerebral Cortex, Jan./Feb. 1991, vol. 1, pp. 1-47.
Fernandez-Corcuera et al., "Bipolar depressed patients show both failure to activate and failure to de-activate during performance of a working memory task", Journal of Affective Disorders, Jun. 2013, vol. 148, No. 2, pp. 170-178.
Ferrari et al., "Global variation in the prevalence and incidence of major depressive disorder: a systematic review of the epidemiological literature", Psychological Medicine, 2013, vol. 43, pp. 471-481.

(56) References Cited

OTHER PUBLICATIONS

Filippini et al., "Distinct patterns of brain activity in young carriers of the APOE-ε4 allele", PNAS, Apr. 28, 2009, vol. 106, No. 17, pp. 7209-7214.
Fitzgerald et al., "An analysis of functional neuroimaging studies of dorsolateral prefrontal cortical activity in depression", Psychiatry Research: Neuroimaging, 2006, vol. 148, pp. 33-45.
Fitzgerald et al., "An fMRI Study of Prefrontal Brain Activation During Multiple Tasks in Patients With Major Depressive Disorder", Human Brain Mapping, 2008, vol. 28, pp. 490-501.
Fonzo et al., "Common and disorder-specific neural responses to emotional faces in generalised anxiety, social anxiety and panic disorders", The British Journal of Psychiatry, 2015, vol. 206, pp. 206-215.
Fornito et al., "Competitive and cooperative dynamics of large-scale brain functional networks supporting recollection", PNAS, Jul. 31, 2012, vol. 109, No. 31, pp. 12788-12793.
Fornito et al., "Genetic Influences on Cost-Effective Organization of Human Cortical Functional Networks", The Journal of Neuroscience, Mar. 2, 2011, vol. 31, No. 9, pp. 3261-3270.
Fornito et al., "The connectomics of brain disorders", Nature Reviews | Neuroscience, Mar. 2015, vol. 16, pp. 159-172.
Forster et al., "Unraveling the anxious mind: anxiety, worry and frontal engagement in sustained attention versus off-task processing", Cerebral Cortex, vol. 25, Mar. 2015, pp. 609-618, Advance Access publications Sep. 22, 2013.
Fox et al., "Clinical applications of resting state functional connectivity", Frontiers in Systems Neuroscience, Jun. 17, 2010, vol. 4, Article 19, pp. 1-13.
Fox et al., "Efficacy of Transcranial Magnetic Stimulation Targets for Depression Is Related to Intrinsic Functional Connectivity with the Subgenual Cingulate", Biol. Psychiatry, 2012, vol. 72, pp. 595-603.
Fox et al., "The human brain is intrinsically organized into dynamic, anticorrelated functional networks", PNAS, Jul. 5, 2005, vol. 102, No. 27, pp. 9673-9678.
Friston et al., "Movement-Related Effects in fMRI Time-Series", Magnetic Resonance in Medicine, Mar. 1996, vol. 35, pp. 346-355.
Fu et al., "Attenuation of the Neural Response to sad Faces in Major Depression by Antidepressant Treatment", Arch. Gen Psychiatry, Sep. 2004, available online Jun. 1, 2012, vol. 61, pp. 877-889.
Fu et al., "Multimodal functional and structural neuroimaging investigation of major depressive disorder following treatment with duloxetine", BMC Psychiatry, 2015, vol. 15, No. 82, pp. 1-11.
Fu et al., "Predictive neural biomarkers of clinical response in depression: A meta-analysis of functional and structural neuroimaging studies of pharmacological and psychological therapies", Neurobiology of Disease, 2013, vol. 52, pp. 75-83.
Garrity et al., "Aberrant 'Default Mode' Functional Connectivity in Schizophrenia", Am. J. Psychiatry, 2007, vol. 164, pp. 450-457.
Gatt et al., "Association between BDNF Val66Met polymorphism and trait depression is mediated via resting EEG alpha ban activity", Biological Psychology, Nov. 2008, available online Jul. 31, 2008, vol. 79, No. 2, pp. 275-284.
Gatt et al., "Early Life Stress Combined with Serotonin 3A Receptor and Brain-Derived Neurotrophic Factor Valine 66 to Methionine Genotypes Impacts Emotional Brain and Arousal Correlates of Risk for Depression", Biol. Psychiatry, 2010, vol. 68, pp. 818-824.
Gatt et al., "Interactions between BDNF Val66Met polymorphism and early life stress predict brain and arousal pathways to syndromal depression and anxiety", Molecular Psychiatry, 2009, vol. 14, pp. 681-695.
Gatt et al., "The TWIN-E Project in Emotional Wellbeing: Study Protocol and Preliminary Heritability Results Across Four MRI and DTI Measures", Twin Research and Human Genetics, Jun. 2012, vol. 15, No. 3, pp. 419-441.
Gavrilescu et al., "Functional Connectivity Estimation in fMRI Data: Influence of Preprocessing and Time Course Selection", Human Brain Mapping, 2008, vol. 28, pp. 1040-1052.
Geisler et al., "Brain structure and function correlates of cognitive subtypes in schizophrenia", Psychiatry Research: Neuroimaging, 2015, vol. 234, pp. 74-83, available online Aug. 21, 2015.
Georgiades et al., "Investigating phenotypic heterogeneity in children with autism spectrum disorder: a factor mixture modeling approach", The Journal of Child Psychology and Psychiatry, 2013, vol. 54, No. 2, pp. 206-215.
Gibb et al., "Reported History of Childhood Abuse and Young Adults' Information-Processing Biases for Facial Displays of Emotion", Child Maltreatment, May 2009, vol. 14, No. 2, pp. 148-156.
Gladding et al., "Open access integrated therapeutic and diagnostic platforms for personalized cardiovascular medicine", J. Pers. Med., 3, 2013, pp. 203-237.
Glahn et al., "Genetic control over the resting brain", PNAS, Jan. 19, 2010, vol. 107, No. 3, pp. 1223-1228.
Glasser et al., "The minimal preprocessing pipelines for the Human Connectome Project", NeuroImage, 2013, available online May 11, 2013, vol. 80, pp. 105-124.
Godlewska et al., "Short-term SSRI treatment normalises amygdala hyperactivity in depressed patients", Psychological Medicine, 2012, vol. 42, pp. 2609-2617.
Goldberg et al., "Executive Subprocesses in Working Memory", Arch. Gen. Psychiatry, Sep. 2003, vol. 60, pp. 889-896.
Goldman et al., "Revising Axis V for DSM-IV: A Review of Measures of Social Functioning", Am. J. Psychiatry, 1992, vol. 149, pp. 1148-1156.
Goldstein-Piekarski et al., "A trans-diagnostic review of anxiety disorder comorbidity and the impact of multiple exclusion criteria on studying clinical outcomes in anxiety disorders", Translational Psychiatry, Jun. 2016, vol. 6, No. 6, e847, pp. 1-9.
Goldstein-Piekarski et al., "Human amygdala engagement moderated by early life stress exposure is a biobehavioral target for predicting recovery on antidepressants", PNAS, vol. 113, No. 42, Oct. 18, 2016, pp. 11955-11960.
Goodyer et al., "Serotonin transporter genotype, morning cortisol and subsequent depression in adolescents", The British Journal of Psychiatry, 2009, vol. 195, pp. 39-45.
Gordon et al., "EEG Alpha Asymmetry in Schizophrenia, Depression, PTSD, Panic Disorder, ADHD and Conduct Disorder", Clinical EEG and Neuroscience, 2010, vol. 41, No. 4, pp. 178-183.
Gordon et al., "Generation and Evaluation of a Cortical Area Parcellation from Resting-State Correlations", Cerebral Cortex, Jan. 2016, vol. 26, pp. 288-303, advance access publication Oct. 15, 2014.
Gordon et al., "Working Memory-Related Changes in Functional Connectivity Persist Beyond Task Disengagement", Human Brain Mapping, Mar. 2014, vol. 35, No. 3, pp. 1004-1017.
Gorgolewski et al., "BIDS apps: Improving ease of use, accessibility, and reproducibility of neuroimaging data analysis and methods", PLoS Computational Biology, Mar. 9, 2017, https://doi.org/10.1371/journal.pcbi.1005209, pp. 1-16.
Gotlib et al., "Cognition and Depression: Current Status and Future Directions", Annu. Rev. Clin. Psychol., 2010, vol. 6, pp. 285-312.
Gotlib et al., "Neural Processing of Reward and Loss in Girls at Risk for Major Depression", Arch. Gen. Psychiatry, 2010, vol. 67, No. 4, pp. 380-387.
Gottesman et al., "The Endophenotype Concept in Psychiatry: Etymology and Strategic Intensions", American Journal Psychiatry, 2003, vol. 160, pp. 636-645.
Green et al., "Personalizing antidepressant choice by sex, body mass index, and symptom profile: An iSPOT-D report", Personalized Medicine in Psychiatry, 2017, vol. 1-2, Available online Dec. 8, 2016, pp. 65-73.
Greicius et al., "Functional connectivity in the resting brain: A network analysis of the default mode hypothesis", PNAS, Jan. 7, 2003, vol. 100, No. 1, pp. 253-258.
Greicius et al., "Resting-State Functional Connectivity in Major Depression: Abnormally Increased Contributions from Subgenual Cingulate Cortex and Thalamus", Biol. Psychiatry, Sep. 1, 2007, vol. 62, Issue 5, pp. 429-437.
Greicius et al., "Resting-State Functional Connectivity Reflects Structural Connectivity in the Default Mode Network", Cerebral Cortex, Jan. 2009, vol. 19, pp. 72-78.

(56) References Cited

OTHER PUBLICATIONS

Greve et al., "Accurate and robust brain image alignment using boundary-based registration", NeuroImage, 2009, vol. 48, pp. 63-72, published online Jun. 30, 2009.

Grieve et al., "Brain imaging predictors and the international study to predict optimized treatment for depression: study protocol for a randomized controlled trial", Trials, Jul. 18, 2013, vol. 14, No. 224, 13 pgs.

Grieve et al., "Widespread reductions in gray matter volume in depression", NeuroImage: Clinical, 2013, vol. 3, pp. 332-339.

Gross et al., "Individual Differences in Two Emotion Regulation Processes Implications for Affect, Relationships, and Well-Being", Journal of Personality and Social Psychology, 2003, vol. 85, No. 2, pp. 348-362.

Gualtieri et al., "The frequency of cognitive impairment in patients with anxiety, depression and bipolar disorder: An unaccounted source of variance in clinical trials", The Journal of Clinical Psychiatry, Jul. 2008, pp. 1-15.

Gur et al., "A method for obtaining 3-dimensional facial expressions and its standardization for use in neurocognitive studies", Journal of Neuroscience Methods, 2002, vol. 115, pp. 137-143.

Gyurak et al., "Frontoparietal Activation During Response Inhibition Predicts Remission to Antidepressants in Patients with Major Depression", Biological Psychiatry, Feb. 15, 2016, vol. 79, pp. 274-281.

Haber et al., "The Reward Circuit: Linking Primate Anatomy and Human Imaging", Neuropsychopharmacology Reviews, 2010, vol. 35, pp. 4-26, published online Oct. 7, 2009.

Hahn et al., "Reduced resting-state functional connectivity between amygdala and orbitofrontal cortex in social anxiety disorder", NeuroImage, 2011, vol. 56, pp. 881-889.

Halari et al., "Reduced activation in lateral prefrontal cortex and anterior cingulate during attention and cognitive control functions in medication-naive adolescents with depression compared to controls", The Journal of Child Psychology and Psychiatry, 2009, vol. 50, No. 3, pp. 307-316.

Halfon et al., "Lifecourse Health Development: Past, Present and Future", Matern. Child Health Journal, 2014, vol. 18, pp. 344-365, published online Aug. 22, 2013.

Hamilton, "A Rating Scale for Depression", J. Neurol. Neurosurg. Psychiat., 1960, vol. 23, pp. 56-62.

Hamilton et al., "Amygdala volume in major depressive disorder: a meta-analysis of magnetic resonance imaging studies", Molecular Psychiatry, 2008, vol. 13, pp. 993-1000.

Hamilton et al., "Default-Mode and Task-Positive Network Activity in Major Depressive Disorder: Implications for Adaptive and Maladaptive Rumination", Biol. Psychiatry, 2011, vol. 70, pp. 327-333.

Hamilton et al., "Depressive Rumination, the Default-Mode Network and the Dark Matter of Clinical Neuroscience", Biological Psychiatry, Aug. 15, 2015, vol. 78, pp. 224-230.

Hamilton et al., "Depressive Rumination, the Default-Mode Network, and the Dark Matter of Clinical Neuroscience", HHS Public Access—author manuscript, 16 pgs., published in final form as Biol. Psychiatry, Aug. 15, 2015, Vo. 78, No. 4, pp. 224-230, doi:10.1016/j.biopsych.2013.02.020.

Hamilton et al., "Functional Neuroimaging of Major Depressive Disorder: a Meta-Analysis and New Integration of Baseline Activation and Neural Response Data", Mechanisms of Psychiatric Illness, American Journal of Psychiatry, 2012, vol. 169, pp. 693-703.

Hammen et al., "Depression and Sensitization to Stressors Among Young Women as a Function of Childhood Adversity", Journal of Consulting and Clinical Psychology, 2000, vol. 68, No. 5, pp. 782-787.

Hardt et al., "Validity of adult retrospective reports of adverse childhood experiences: review of the evidence", Journal of child Psychology and Psychiatry, 2004, vol. 45, No. 2, pp. 260-273.

Harmer et al., "Antidepressant Drug Treatment Modifies the Neural Processing of Nonconscious Threat Cues", Biol. Psychiatry, 2006, vol. 59, pp. 816-820.

Harris et al., "Morning cortisol as a risk factor for subsequent major depressive disorder in adult women", British Journal of Psychiatry, 2000, vol. 177, pp. 505-510.

Harvey et al., "Cognitive control and brain resources in major depression: An fMRI study using the n-back task", NeuroImage, 2005, vol. 26, pp. 860-869.

Hasselbalch et al., "Cognitive Deficits in the Remitted State of Unipolar Depressive Order", Neuropsychology, 2012, vol. 26, No. 5, pp. 642-651.

Hatch et al., "Anorexia Nervosa: Towards An Integrative Neuroscience Model", Eur. Eat. Disorders Rev., 2010, vol. 18, pp. 165-179.

Hatch et al., "In First Presentation Adolescent Anorexia Nervosa, Do Cognitive Markers of Underweight Status Change with Weight Gain Following a Refeeding Intervention?", Int. J. Eat. Disord., 2010, vol. 43, pp. 295-306.

Hayes et al., "Emotion and cognition interactions in PTSD: a review of neurocognitive and neuroimaging studies", Frontiers in Integrative Neuroscience, Oct. 9, 2012, vol. 6, Article 90, pp. 1-14.

Hayes et al., "Quantitative meta-analysis of neural activity in posttraumatic stress disorder", Biology of Mood & Anxiety Disorders, 2010, vol. 2, No. 9, pp. 1-13.

Heatherton et al., "The Fagerstrom Test for Nicotine Dependence: a revision of the Fagerstrom Tolerance Questionnaire", British Journal of Addiction, 1991, vol. 86, pp. 1119-1127.

Heim et al., "Current research trends in early life stress and depression: Review of human studies on sensitive periods, gene-environment interactions, and epigenetics", Experimental Neurology, 2012, vol. 233, pp. 102-111.

Heim et al., "Decreased Cortical Representation of Genital somatosensory Field After Childhood Sexual Abuse", Am. J. Psychiatry, 2013, vol. 170, pp. 616-623.

Heim et al., "Effect of childhood trauma on adult depression and neuroendocrine function: sex-specific moderation by CRH receptor 1 gene", Frontiers in Behavioral Neuroscience, Nov. 6, 2009, vol. 3, Article 41, pp. 1-10.

Heim et al., "Neurobiological and Psychiatric Consequences of Child Abuse and Neglect", Developmental Psychobiology, Sep. 28, 2010, Wiley Online Library, DOI 10.1002/dev.20494, 20 pgs.

Heim et al., "The Impact of Early Adverse Experiences on Brain Systems Involved in the Pathophysiology of Anxiety and Affective Disorders", Biol. Psychiatry, 1999, vol. 46, pp. 1509-1522.

Heller, "Cortical-Subcortical Interactions in Depression: From Animal Models to Human Psychopathology", Frontiers in Systems Neuroscience, Mar. 7, 2016, vol. 10, Article 20, pp. 1-10.

Henson, "Understanding Internal Consistency Reliability Estimates: A Conceptual Primer on Coefficient Alpha", Measurement and Evaluation in Counseling and Development, Oct. 2001, vol. 34, No. 34, pp. 177-189.

Herman et al., "Limbic system mechanisms of stress regulation: Hypothalamo-pituitary-adrenocortical axis", Progress in Neuro-Psychopharmacology & Biological Psychiatry, 2005, vol. 29, pp. 1201-1213.

Hilimire et al., "Effects of subcallocal cingulate deep brain stimulation on negative self-bias in patients with treatment resistant depression", Brain Stim., 8, 2015, pp. 185-191.

Hinkelmann et al., "Changes in cortisol secretion during antidepressive treatment and cognitive improvement in patients with major depression: A longitudinal study", Psychoneuroendocrinology, Jan. 2012, vol. 37, No. 5, pp. 685-692.

Ho et al., "Fusiform gyrus dysfunction is associated with perceptual processing efficiency to emotional faces in adolescent depression: a model-based approach", Frontiers in Psychology, Feb. 2016, vol. 7, Article 40, pp. 1-14.

Holmes et al., "Prefrontal functioning during context processing in schizophrenia and major depression: An event-related fMRI study", Schizophrenia Research, 2005, vol. 76, pp. 199-206.

Holmes et al., "Response conflict and frontocingulate dysfunction in unmedicated participants with Major Depression", NIH Public Access—Author Manuscript, 22 pgs., published in final form as Neuropsychologia, Oct. 2008, vol. 46, No. 12, pp. 1904-2913, doi:10.1016/j.neuropsychologia.2008.05.028.

(56) References Cited

OTHER PUBLICATIONS

Holmes et al., "Utility of genetic determinants of lipids and cardiovascular evens in assessing risk", Nature Reviews | Cardiology, Apr. 2011, published online Feb. 15, 2011, vol. 8, pp. 207-221.
Horn et al., "Glutamatergic and resting-state functional connectivity correlates of severity in major depression—the role of pregenual anterior cingulate cortex and anterior insula", Frontiers in Systems Neuroscience, Jul. 15, 2010, vol. 4, Article 33, pp. 1-10.
Horn et al., "The structural-functional connector and the default mode network of the human brain", Neuroimage, vol. 102, 2014, pp. 142-151, available online Oct. 4, 2013.
Hosking et al., "Detection of genotyping errors by Hardy-Weinberg equilibrium testing", European Journal of Human Genetics, 2004, vol. 12, pp. 395-399.
Howie et al., "A Flexible and Accurate Genotype Imputation Method for the Next Generation of Genome-Wide Association Studies", PLoS Genetics, Jun. 19, 2009, vol. 5, Issue 6, e1000529, pp. 1-15.
Huang, "Early-life stress impacts the developing hippocampus and primes seizure occurrence: cellular, molecular, and epigenetic mechanisms", Frontiers in Molecular Neuroscience, Feb. 10, 2014, vol. 7, Article 8, pp. 1-15.
Huckins, "Reward and Self-Regulation in the Resting Brain", URL:https://search.proquest.com/docview/1695275330?pq-origsite=gscholar, 2015, pp. 18-24, XP055678294.
Hugdahl et al., "Brain Activation Measured with fMRI During a Mental Arithmetic Task in Schizophrenia and Major Depression", Am. J. Psychiatry, 2004, vol. 161, pp. 286-293.
Hugdahl et al., "On the existence of a generalized non-specific task-dependent network", Frontiers in Human Neuroscience, Aug. 2015, vol. 9, Article 430, pp. 1-15.
Huys et al., "Computational psychiatry as a bridge from neuroscience to clinical applications", Nature Neuroscience, Mar. 2016, published online Feb. 23, 2016, vol. 19, No. 3, pp. 404-413.
Iacono et al., "Minnesota Twin Family Study", Twin Research, Oct. 2002, vol. 5, No. 5, pp. 482-487.
Iacoviello et al., "Cognitive-Emotional Training as an Intervention for Major Depressive Disorder", Depression and Anxiety, 2014, vol. 31, pp. 699-706.
Insel et al., "Research Domain Criteria (RDoC): Toward a New Classification Framework for Research on Mental Disorders", Am. J. Psychiatry, Jul. 2010, vol. 156, No. 7, pp. 748-751.
Ioannidis, "Why Most Published Research Findings Are False", PLoS Medicine, Aug. 2005, vol. 2, Issue 8, pp. 0696-0701.
Ishibashi et al., "Binding of Pramipexole to Extrastriatal Dopamine D2/D3 Receptors in the Human Brain: A Positron Emission Tomography Study Using 11C-FLB 457", PLoS ONE, Mar. 2011, vol. 6, Issue 3, e17723, pp. 1-6.
Iwabuchi et al., "Localized connectivity in depression: a meta-analysis of resting state functional imaging studies", Neuroscience and Biobehavioral Reviews, vol. 51, 2015, pp. 77-86, available online Jan. 16, 2015.
Izumi et al., "Target brain sites of the anxiolytic effect of citalopram, a selective serotonin reuptake inhibitor", European Journal of Pharmacology, 2006, available online Feb. 21, 2006, vol. 534, pp. 129-132.
Jang et al., "The Impact of Genetic Variation in COMT and BDNF on Resting-State Functional Connectivity", Int. Journal of Imaging Syst. Technol., 2012, vol. 22, pp. 97-102.
Jaworska et al., "A review of fMRI studies during visual emotive processing in major depressive disorder", The World Journal of Biological Psychiatry, 2015, published online Mar. 17, 2014, vol. 16, pp. 448-471.
Jedema et al., "Corticotropin-Releasing Hormone Directly Activates Noradrenergic Neurons of the Locus Ceruleus Recorded in Vitro", The Journal of Neuroscience, Oct. 27, 2004, vol. 24, No. 43, pp. 9703-9713.
Johansen-Berg et al., "Anatomical Connectivity of the Subgenual Cingulate Region Targeted with Deep Brain Stimulation for Treatment-Resistant Depression", Cerebral Cortex, Jun. 2008, Advance Access publication Oct. 10, 2007, vol. 18, pp. 1374-1383.
Johnson et al., "SNAP: a web-based tool for identification and annotation of proxy SNPs using HapMap", Bioinformatics, 2008, Advance Access publication Oct. 30, 2008, vol. 24, No. 24, pp. 2938-2939.
Juruena et al., "Different responses to dexamethasone and prednisolone in the same depressed patients", Psychopharmacology, 2006, published online Oct. 3, 2006, vol. 189, pp. 225-235.
Kaffman et al., "Neurodevelopmental sequelae of postnatal maternal care in rodents: clinical and research implications of molecular insights", Journal of Child Psychology and Psychiatry, 2007, vol. 49, No. 3/4, pp. 224-244.
Kaiser et al., "Large-Scale Network Dysfunction in Major Depressive Disorder", JAMA Psychiatry, 2015, vol. 72, No. 6, pp. 603-611, published online Mar. 18, 2015.
Kaiser et al., "Large-Scale Network Dysfunction in Major Depressive Disorder (includes supplementary online content)", JAMA Psychiatry, published online Mar. 18, 2015, 37 pgs.
Kalayam et al., "Prefrontal Dysfunction and Treatment Response in Geriatric Depression", Arch. Gen. Psychiatry, 1999, vol. 56, pp. 713-718.
Kapoor et al., "Effects of Sertraline and Fluoxetine on P-Glycoprotein at Barrier Sites: In Vivo and In Vitro Approaches", PLOS, Feb. 28, 2013, vol. 8, Issue 2, e56525, pp. 1-6.
Karlsson et al., "Altered brain concentrations of citalopram and escitalopram in P-glycoprotein deficient mice after acute and chronic treatment", European Neuropsychopharmacology, 2013, vol. 23, pp. 1636-1644.
Karlsson et al., "Blood-brain barrier penetration of the enantiomers of venlafaxine and its metabolites in mice lacking P-glycoprotein", European Neuropsychopharmacology, 2010, vol. 20, pp. 632-640.
Kato et al., "ABCB1 (MDR1) gene polymorphisms are associated with the clinical response to paroxentine in patients with major depressive disorder", Progress in Neuro-Psychopharmacology & Biological Psychiatry, 2008, vol. 32, pp. 398-404.
Keedwell et al., "A Double Dissociation of Ventromedial Prefrontal Cortical Responses to Sad and Happy Stimuli in Depressed and Healthy Individuals", Biol. Psychiatry, 2005, vol. 58, pp. 495-503.
Keedwell et al., "The Neural Correlates of Anhedonia in Major Depressive Disorder", Biol. Psychiatry, 2005, vol. 58, pp. 843-853.
Keefe et al., "Cognitive Effects of Pharmacotherapy for Major Depressive Disorder: A Systematic Review", J. Clin. Psychiatry, 2014, published online Jun. 8, 2014, vol. 75, No. 8, pp. 864-876.
Keller, "Past, Present, and Future Directions for Defining Optimal Treatment Outcome in Depression", JAMA, Jun. 18, 2003, vol. 289, No. 23, pp. 3152-3160.
Keller et al., "A comparison of Nefazodone, the Cognitive Behavioral-Analysis System of Psychotherapy, and Their Combination for the Treatment of Chronic Depression", Journal of Medicine, May 18, 2000, vol. 342, No. 20, pp. 1462-1470.
Kemp et al., "Fronto-Temporal Alterations Within the First 200 ms During an Attentional Task Distinguish Major Depression, Non-Clinical Participants With Depressed Mood and Healthy Controls: A Potential Biomarker?", Human Brain Mapping, 2009, vol. 30, pp. 602-614.
Kempton et al., "Structural Neuroimaging Studies in Major Depressive Disorder", Arch. Gen. Psychiatry, 2011, vol. 68, No. 7, pp. 675-690.
Kendler, "The Structure of Psychiatric Science", Am. J. Psychiatry, 2014, vol. 171, pp. 931-938.
Kendler et al., "Stressful Life Events, Genetic Liability, and Onset of an Episode of Major Depression in Women", Am. J. Psychiatry, Jun. 1995, vol. 152, vol. 6, pp. 833-842.
Kent et al., "The Impact of Childhood Emotional Abuse: An Extension of the Child Abuse and Trauma Scale", Child Abuse & Neglect, 1998, vol. 22, No. 5, pp. 393-399.
Keogh et al., "Exploring the Factor Structure of the Mood and Anxiety Symptom Questionnaire (MASQ)", Journal of Personality Assessment, Jun. 10, 2010, vol. 74, No. 1, pp. 106-125.
Kessler et al., "Childhood adversity and adult psychiatric disorder in the US National Comorbidity Survey", Psychological Medicine, 1997, vol. 27, pp. 1101-1119.

(56) References Cited

OTHER PUBLICATIONS

Kessler et al., "Co-morbid major depression and generalized anxiety disorders in the National Comorbidity Survey follow-up", Psychological Medicine, Nov. 30, 2007, vol. 38, pp. 365-374.
Kessler et al., "Lifetime and 12-Month Prevalence of DSM-III-R Psychiatric Disorders in the United States", Archives of General Psychiatry, Jan. 1994, vol. 51, No. 1, pp. 8-19.
Kessler et al., "Lifetime Prevalence and Age-of-Onset Distributions of DMS-IV Disorders in the National Comorbidity Survey Replication", Archives of General Psychiatry, Jul. 2005, vol. 62, No. 5, pp. 593-602.
Kessler et al., "The World Health Organization Health and Work Performance Questionnaire (HPQ)", J. Occup. Environ. Med., 2003, vol. 45, pp. 156-174.
Khan et al., "BMI, sex, and antidepressant response", Journal of Affective Disorders, 2007, available online Sep. 27, 2006, vol. 99, pp. 101-106.
Khan et al., "Sex Differences in Antidepressant Response in Recent Antidepressant Clinical Trials", Journal of Clinical Psychopharmacology, Aug. 2005, vol. 25, No. 4, pp. 318-324.
Kilford et al., "Introduction to Connectivity: PPI and SEM", Methods for Dummies 2011/2012, 38 pgs.
Killgore et al., "Cortico-Limbic Responses to Masked Affective Faces Across PTSD, Panic Disorder, and Specific Phobia", Depression and Anxiety, 2014, vol. 31, pp. 150-159.
Kim et al., "Reduced Caudate Gray matter volume in women with Major Depressive Disorder", NIH Public Access—Author Manuscript, 13 pgs., published in final for as Psychiatry Res., Nov. 30, 2008, vol. 164, No. 2, pp. 114-122, doi:10.1016/j.pscycyresns.2007.12.020.
Kim et al., "The structural and functional connectivity of the amygdala: From normal emotion to pathological anxiety", Behavioural Brain Research, 2011, vol. 223, pp. 403-410.
Kloiber et al., "Overweight and Obesity Affect Treatment Response in Major Depression", Biol. Psychiatry, 2007, vol. 62, pp. 321-326.
Klumpp et al., "Anterior cingulate cortex and insula response during indirect and direct processing of emotional faces in generalized social anxiety disorder", Biology of Mood & Anxiety Disorders, Apr. 2, 2013, vol. 3, No. 7, pp. 1-9.
Knott et al., "EEG power, frequency, asymmetry and coherence in male depression", Psychiatry Research, Neuroimaging, 2001, vol. 106, pp. 123-140.
Kober et al., "Functional grouping and cortical-subcortical interactions in emotion: A meta-analysis of neuroimaging studies", NeuroImage, 2008, vol. 42, pp. 998-1031, available online Apr. 11, 2008.
Koenigs et al., "The functional neuroanatomy of depression: Distance roles for ventromedial and dorsolateral prefrontal cortex", NIH Public Access—Author manuscript, 10 pgs., published in final form as: Behav. Brain Res., Aug. 12, 2009, vol. 201, No. 2, pp. 239-243.
Korgaonkar et al., "Abnormal Structural Networks Characterize Major Depressive Disorder: A Connectome Analysis", Biol. Psychiatry, 2014, vol. 76, pp. 567-574.
Korgaonkar et al., "Establishing the Resting State Default Mode Network Derived from Functional Magnetic Resonance Imaging Tasks as an Endophenotype: A Twins Study", Human Brain Mapping, Jan. 24, 2014, vol. 35, pp. 3893-3902.
Korgaonkar et al., "Loss of White Matter Integrity in Major depressive Disorder: Evidence Using Tract-Based Spatial Statistical Analysis of Diffusion Tensor Imaging", Human Brain Mapping, 2011, published online Dec. 17, 2010, vol. 32, pp. 2161-2171.
Korgaonkar et al., "Mapping inter-regional connectivity of the entire cortex to characterize major depressive disorder: a whole-brain diffusion tensor imaging tractography study", NeuroReport, 2012, vol. 23, pp. 566-571.
Korgaonkar et al., "Using Standardized fMRI Protocols to Identify Patterns of Prefrontal Circuit Dysregulation that are Common and Specific to Cognitive and Emotional Tasks in Major Depressive Disorder: First Wave Results from the iSPOT-D Study", Neuropsychopharmacology, vol. 38, 2013, Online preview Dec. 5, 2012, pp. 863-871.
Koric et al., "How Cognitive Performance-Induced Stress Can Influence Right VLPFC Activation: An fMRI Study in Healthy Subjects and In Patients with Social Phobia", Human Brain Mapping, 2012, published online Jul. 18, 2011, vol. 33, pp. 1973-1986.
Kornstein et al., "Gender Differences in Treatment Response to Sertraline Versus Imipramine in Chronic Depression", Am. J. Psychiatry, Sep. 2000, vol. 157, pp. 1445-1452.
Koslow et al., "BRAINnet: A Standardized Global Human Brain Project", Technology and Innovation, Jan. 2013, vol. 15, pp. 17-29.
Kozak et al., "The NIMH Research Domain Criteria Initiative: Background, Issues and Pragmatics", Psychophysiology, 2016, vol. 53, pp. 286-297.
Kriegeskorte et al., "Circular analysis in systems neuroscience: the dangers of double dipping", Nature Neuroscience, May 2009, vol. 12, No. 5, pp. 535-540, published online Apr. 26, 2009.
Kupfer et al., "Neuroscience, clinical evidence, and the future of psychiatric classification in DSM-5", American Journal of Psychiatry, vol. 168, No. 7, Jul. 2011, pp. 672-674.
Lamers et al., "Structure of major depressive disorder in adolescents and adults in the US general population", The British Journal of Psychiatry, Aug. 2012, vol. 201, No. 2, pp. 143-150, printed from https://www.ncbi.nlm.nih.gov/pmc/articles/PMC3409428/?report=printable, 19 pgs.
Langenecker et al., "Current Neural and Behavioral Dimensional Constructs Across Mood Disorders", NIH Public Access—Author Manuscript, 19 pgs., published in final form as Curr. Behav. Neurosci. Rep., Sep. 1, 2014, vol. 1, No. 3, pp. 144-153, doi:10.1007/s40473-014-0018-x.
Langenecker et al., "Frontal and Limbic Activation During Inhibitory Control Predicts Treatment Response in Major Depressive Disorder", Biol. Psychiatry, 2007, vol. 62, No. 1272-1280.
Lanius et al., "Restoring large-scale brain networks in PTSD and related disorders: a proposal for neuroscientifically-informed treatment interventions", European Journal of Psychotraumatology, Mar. 31, 2015, vol. 5, No. 27313, pp. 1-12.
Lawrence et al., "Subcortical and Ventral Prefrontal Cortical Neural Responses to Facial Expressions Distinguish Patients with Bipolar Disorder and Major Depression", Biol. Psychiatry, 2004, vol. 55, pp. 578-587.
Leal et al., "BDNF-induced local protein synthesis and synaptic plasticity", Neuropharmacology, 2014, vol. 76, pp. 639-656.
Lee et al., "Role of the Hippocampus, the Bed Nucleus of the Stria Terminalis, and the Amygdala in the Excitatory Effect of Corticotropin-Releasing Hormone on the Acoustic Startle Reflex", The Journal of Neuroscience, Aug. 15, 1997, vol. 17, No. 16, pp. 6434-6446.
Lee et al., "The neural substrates of affective processing toward positive and negative affective pictures in patients with major depressive disorder", Progress in Neuro-Psychopharmacology & Biological Psychiatry, 2007, available online Jul. 5, 2007, vol. 31, pp. 1487-1492.
Leergaard et al., "Mapping the connectome: multi-level analysis of brain connectivity", Frontiers in Neuroinformatics, May 1, 2012, vol. 6, Article 14, pp. 1-6.
Lemke et al., "Psychomotor retardation and anhedonia in depression", Acta Psychiatrica Scandinavica, 1999, vol. 99, pp. 252-256.
Letizia et al., "Magnetic resonance imaging volumes of the hippocampus in drug-naive patients with post-traumatic stress disorder without comorbidity conditions", Journal of Psychiatric Research, 2008, vol. 42, No. 752-762.
Lewis et al., "Impact of Childhood Trauma on Treatment Outcome in the Treatment for Adolescents with Depression Study (TADS)", Journal of the American Academy of Child & Adolescent Psychiatry, Feb. 2010, vol. 49, No. 2, pp. 132-140.
Lewis et al., "Learning sculpts the spontaneous activity of the resting human brain", PNAS, Oct. 13, 2009, vol. 106, No. 41, pp. 17558-17563.
Li et al., "Adjusting multiple testing in multilocus analyses using the eigenvalues of a correlation matrix", Heredity, 2005, available online Aug. 3, 2005, vol. 95, pp. 221-227.

(56) References Cited

OTHER PUBLICATIONS

Liao et al., "Altered Effective Connectivity Network of the Amygdala in Social Anxiety Disorder: A Resting-State fMRI Study", PLoS ONE, Dec. 2010, vol. 5, Issue 12, e15238, pp. 1-9.
Liddell et al., "A direct brainstem-amygdala-cortical 'alarm' system for subliminal signals of fear", NeuroImage, 2005, vol. 24, pp. 235-243.
Liddell et al., "Rates of Decline Distinguish Alzheimer's Disease and Mild Cognitive Impairment Relative to Normal Aging: Integrating Cognition and Brain Function", Journal of Integrative Neuroscience, Apr. 2007, vol. 6, No. 1, pp. 141-174.
Lin et al., "ABCB1 gene polymorphisms are associated with the severity of major depressive disorder and its response to escitalopram treatment", Pharmacogenetics and Genomics, 2011, vol. 21, pp. 163-170.
Lin et al., "Both body weight and BMI predicts improvement in symptom and functioning for patients with major depressive disorder", Journal of Affective Disorders, 2014, vol. 161, pp. 123-126, available online Mar. 13, 2014.
Linden et al., "Sad benefit in face working memory: an emotional bias of melancholic depression", J. Affect. Disord., Dec. 2011, vol. 135, No. 1-3, pp. 251-257.
Linden et al., "The Functional neuroanatomy of Target Detection: An fMRI Study of Visual and Auditory Oddball Tasks", Cerebral Cortex, Dec. 1999, vol. 9, pp. 815-823.
Lindquist et al., "A functional architecture of the human brain: Emerging insights from the science of emotion", NIH Public Access—Author Manuscript, 16 pgs., published in final form as Trends Cogn. Sci, Nov. 2012, vol. 16, No. 11, pp. 533-540, doi: 10.1016/j.tics.2012.09.005.
Liotti et al., "Unmasking Disease-specific Cerebral Blood Flow Abnormalities: Mood Challenge in Patients with Remitted Unipolar Depression", Am. J. Psychiatry, Nov. 2002, vol. 159, pp. 1830-1840.
Liu et al., "Association study of corticotropin-releasing hormone receiptor1 gene polymorphisms and antidepressant response in major depressive disorders", Neuroscience Letters, Apr. 2007, vol. 414, No. 2, pp. 155-158.
Loeuillet et al., "Promoter polymorphisms and allelic imbalance in ABCG1 expression", Pharmacogenetics and Genomics, 2007, vol. 17, pp. 951-959.
Lovibond et al., "The Structure of Negative Emotional States: Comparison of the Depression Anxiety Stress Scales (DASS) with the Beck Depression and Anxiety Inventories", Behav. Res. Ther., 1995, vol. 33, No. 3, pp. 335-343.
Lupien et al., "Effects of stress throughout the lifespan on the brain, behaviour and cognition", Nature Reviews | Neuroscience, Jun. 2009, vol. 10, pp. 434-445, published online Apr. 29, 2009.
Lupien et al., "Larger amygdala but No. change in hippocampal volume in 10-year-old children exposed to maternal depressive symptomatology since birth", PNAS, Aug. 23, 2011, vol. 108, No. 34, pp. 14324-14329.
Luppino et al., "Overweight, Obesity, and Depression", Arch. Gen. Psychiatry, 2010, vol. 67, No. 3, pp. 220-229.
Ma, "Neuropsychological mechanism underlying antidepressant effect: a systematic meta-analysis", Molecular Psychiatry, 2015, vol. 20, pp. 311-319, published online Mar. 25, 2014.
Madhoo et al., "Lisdexamfetamine Dimesylate Augmentation in Adults with Persistent Executive Dysfunction After Partial or Full Remission of Major Depressive Disorder", Neuropsychopharmacology, 2014, preview online Dec. 6, 2013, vol. 39, pp. 1388-1398.
Majer et al., "Association of childhood trauma with cognitive function in health adults: a pilot study", BMC Neurology, 2010, vol. 10, No. 61, pp. 1-10.
Manoliu et al., "Insular dysfunction within the salience network is associated with severity of symptoms and aberrant inter-network connectivity in major depressive disorder", Frontiers in Human Neuroscience, Jan. 21, 2014, vol. 7, Article 930, pp. 1-17.
Marcus et al., "Human Connectome Project informatics: Quality control, database services, and data visualization", NeuroImage, 2013, available online May 24, 2013, vol. 80, pp. 202-219.
Mark et al., "Psychotropic Drug Prescriptions by Medical Specialty", Psychiatric Services, ps.psychiatryonline.org, Sep. 2009, vol. 60, No. 9, pp. 1167.
Markoff, "Obama seeking to boost study of human brain", Retrieved from: http://www.nytimes.com/2013/02/18/science/project-seeks-to-build-map-of-human-brain.html, 2013, 5 pgs.
Mathersul et al., "Explicit identification and implicit recognition of facial emotions: II. Core domains and relationships with general cognition", Journal of Clinical and Experimental Neuropsychology, 2009, vol. 31, No. 2, pp. 278-291.
Matsuo et al., "Prefrontal hyperactivation during working memory task in untreated individuals with major depressive disorder", Molecular Psychiatry, 2007, vol. 12, pp. 158-166, published online Sep. 19, 2006.
Matthews et al., "Decreased functional coupling of the amygdala and supragenual cingulate is related to increased depression in unmedicated individuals with current major depressive disorder", Journal of Affective Disorders, 2008, available online Jul. 7, 2008, vol. 111, pp. 13-20.
Mattson et al., "Clinical neuroprediction: Amygdala reactivity predicts depressive symptoms 2 years later", Social Cognitive and Affective Neuroscience, 2016, pp. 892-898, advance publication Feb. 10, 2016.
Mayberg, "Targeted electrode-based modulation of neural circuits for depression", The Journal of Clinical Investigation, Apr. 2009, vol. 119, No. 4, pp. 717-725.
Mayberg et al., "Regional Metabolic Effects of Fluoxetine in Major Depression: Serial Changes and Relationship to Clinical Response", Biol. Psychiatry, Oct. 15, 2000, vol. 48, Issue 8, pp. 830-843.
Mccrory et al., "Amygdala activation in maltreated children during pre-attentive emotional processing", The British Journal of Psychiatry, 2013, vol. 202, pp. 269-276.
Mccrory et al., "The link between child abuse and psychopathology: A review of neurobiological and genetic research", J. R. Soc. Med, 2012, vol. 105, pp. 151-156.
Mccrory et al., "The theory of latent vulnerability: Reconceptualizing the link between childhood maltreatment and psychiatric disorder", Development and Psychopathology, May 2015, vol. 27, pp. 493-505.
Mcewen, "Brain on stress: How the social environment gets under the skin", PNAS, Oct. 16, 2012, vol. 109, Supp. 2, pp. 17180-17185, 1561.
Mcewen et al., "Mechanisms of stress in the brain", Focus on Stress, Nature Neuroscience, Oct. 2015, vol. 18, No. 10, pp. 1353-1363, published online Sep. 25, 2015.
Mcfarlane et al., "The Impact of Early Life Stress on Psychophysiological, Personality and Behavioral Measures in 740 Non-Clinical Subjects", Journal of Integrative Neuroscience, Apr. 2005, vol. 4, No. 1, pp. 27-40.
Mcgee et al., "The Measurement of Maltreatment: A Comparison of Approaches", Child Abuse & Neglect, 1995, vol. 19, No. 2, pp. 233-249.
Mcgovern et al., "Role of the dorsal anterior cingulate cortex in obsessive-compulsive disorder: converging evidence from cognitive neuroscience and psychiatric neurosurgery", J. Neurosurg., Jan. 2017, vol. 126, pp. 132-147.
Mcintyre et al., "A randomized, double-blind, placebo-controlled study of vortioxetine on cognitive function in depressed adults", International Journal of Neuropsychopharmacology, 2014, vol. 17, pp. 1557-1567.
Meletti et al., "Fear and happiness in the eyes: An intra-cerebral event-related potential study from the human amygdala", Neuropsychologia, 2012, available online Oct. 25, 2011, vol. 50, pp. 44-54.
Menon, "Large-scale brain networks and psychopathology: a unifying triple network model", Trends in Cognitive Sciences, Oct. 2011, vol. 15, No. 10, pp. 483-506.
Menon et al., "Saliency, switching, attention and control: a network of insult function", Brain Struc. Func., Jun. 2010, vol. 214, No. 5-6, pp. 655-667.
Menu et al., "Antidepressants and ACB1 Gene C3435T Functional Polymorphism: A Naturalistic Study", Neuropsychobiology, 2010, vol. 62, pp. 193-197, published online Jul. 22, 2010.

(56) References Cited

OTHER PUBLICATIONS

Menzies et al., "Integrating evidence from neuroimaging and neuropsychological studies of obsessive-compulsive disorder: The orbitofronto-striatal model revisited", Neuroscience and Biobehavioral Reviews, 2008, vol. 32, pp. 525-549.

Mesulam, "From sensation to cognition", Brain, 1998, vol. 121, pp. 1013-1052.

Meyer et al., "Development and Validation of the Penn State Worry Questionnaire", Behav. Res. Ther., 1990, vol. 28, No. 6, pp. 487-495.

Michopoulos et al., "Neuropsychological and hypothalamic-pituitary-axis function in female patients with melancholic and non-melancholic depression", Eur. Arch. Psychiatry Clin. Neurosci., 2008, vol. 258, pp. 217-225.

Milaneschi et al., "Polygenic dissection of major depression clinical heterogeneity", HHS Public Access—author manuscript, 16 pgs., published in final form as Mol. Psychiatry, Apr. 2016, vol. 21, No. 4, pp. 516-522, doi:10.1038/mp.2015.86.

Miller et al., "An Integrative Theory of Prefrontal Cortex Function", Annu. Rev. Neurosci., 2001, vol. 24, pp. 167-202.

Mitchell, "Therapeutic drug monitoring of non-tricyclic antidepressant drugs", Clin. Chem. Lab Med., 2004, vol. 42, No. 11, pp. 1212-1218.

Mitterschiffthaler et al., "Neural response to pleasant stimuli in anhedonia: an fMRI study", NeuroReport, Feb. 10, 2003, vol. 14, No. 2, pp. 177-182.

Moon et al., "Whole-brain gray matter volume abnormalities in patients with generalized anxiety disorder: Voxel based morphometry", NeuroReport, vol. 25, No. 3, 2014, pp. 184-189.

Moran, "Anxiety and Working Memory Capacity: A Meta-Analysis and Narrative Review", Psychological Bulletin, 2016, vol. 142, No. 8, pp. 831-864.

Mostert et al., "Similar Subgroups Based on Cognitive Performance Parse Heterogeneity in Adults with ADHD and Healthy Controls", Journal of Attention Disorders, Feb. 1, 2018, vol. 22, No. 3, pp. 281-292.

Mueller et al., "Grey matter volume in Adolescent Anxiety: An Impact of the Brain-Derived Neurotropic Factor Val66Met Polymorphism?", NIH Public Access—Author Manuscript, 19 pgs., published in final form as: J. Am. Acad. Child Adolesc. Psychiatry, Feb. 2013, vol. 52, No. 2, pp. 184-195, doi:10.1016/j/jaac.2012.11.016.

Mulders et al., "Resting-state functional connectivity in major depressive disorder: A review", Neuroscience and Biobehavioral Reviews, 2015, available online Jul. 30, 2015, vol. 56, pp. 330-344.

Murphy et al., "Effect of a single dose of citalopram on amygdala response to emotional faces", British Journal of Psychiatry, Jun. 2009, vol. 194, No. 6, printed Feb. 22, 2014 from https://www.ncbi.nlm.nih.gov/pmc/articles/PMC2802527/?report=printable, 13 pages.

Murphy et al., "Effect of a single dose of citalopram on amygdala response to emotional faces", The British Journal of Psychiatry, 2009, vol. 194, pp. 535-540.

Murphy et al., "The impact of global signal regression on resting state correlations: Are anti-correlated networks introduced?", NeuroImage, Feb. 1, 2009, Published online Oct. 11, 2008, vol. 44, No. 3, pp. 893-905.

Murri et al., "HPA axis and aging in depression: Systematic review and meta-analysis", Psychoneuroendocrinology, 2014, vol. 41, pp. 46-62.

Musgrove et al., "Impaired Bottom-UP Effective Connectivity Between Amygdala and Subgenual Anterior Cingulate Cortex in Unmedicated Adolescents with Major Depression: Results from a Dynamic Casual Modeling Analysis", Brain Connectivity, 2015, vol. 5, No. 10, pp. 608-619.

Nanni et al., "Childhood Maltreatment Predicts Unfavorable Course of Illness and Treatment Outcome in Depression: A Meta-Analysis", Am. J. Psychiatry, 2012, vol. 169, pp. 141-151.

Neale et al., "Methodology for Genetic Studies of Twins and Families", Kluwer Academic Publishers B.V., 308 pgs.

Neale et al., "Mx: Statistical Modeling", Sixth Edition, Apr. 15, 2004, first published 1991, 218 pgs.

Nemeroff et al., "Differential responses to psychotherapy versus pharmacotherapy in patients with chronic forms of major depression and childhood trauma", PNAS, Nov. 25, 2003, vol. 100, No. 24, pp. 14293-14296.

Nemeroff et al., "The Preeminent Role of Childhood Abuse and Neglect in Vulnerability of Major Psychiatric Disorders: Toward Elucidating the Underlying Neurobiological Mechanisms", Journal of the American Academy of Chile & Adolescent Psychiatry, Apr. 2014, vol. 53, No. 4, pp. 395-397.

Nestler et al., "The Mesolimbic Dopamine Reward Circuit in Depression", Biol. Psychiatry, 2006, vol. 59, pp. 1151-1159.

Nicholson et al., "Interaction of noradrenaline and cortisol predicts negative intrusive memories in posttraumatic stress disorder", Neurobiology of Learning and Memory, 2014, vol. 112, pp. 204-211, available online Dec. 1, 2013.

Niendam et al., "Meta-analytic evidence for a superordinate cognitive control network subserving diverse executive functions", Cogn. Affect. Behav. Neurosci, 2012, published online Jan. 27, 2012, vol. 12, pp. 241-268.

Nierenberg et al., "Definitions of Antidepressant Treatment Response, Remission, Nonresponse, Partial Response, and Other Relevant Outcomes: A Focus on Treatment-Resistant Depression", Journal of Clinical Psychiatry, Feb. 2001, vol. 62 (Suppl 16).pp. 5-9.

Nih, "Screening for Drug Use in General Medical Settings—Resource Guide", U.S. Department of Health and Human Services, National Institutes of Health, 2012, 22 pgs.

Noordam et al., "Associate Between Genetic Variation in the ABCB1 Gene and Switching, Discontinuation, and Dosage of Antidepressant Therapy", Journal of Clinical Psychopharmacology, Aug. 2013, vol. 33, No. 4, pp. 546-550.

Norton, "Depression Anxiety and Stress Scales (DASS-21): Psychometric analysis across four racial groups", Anxiety, Stress & Coping, Sep. 2007, vol. 20, No. 3, pp. 253-265.

Ogle et al., "Guidance for the Discontinuation or Switching of Antidepressant Therapies in Adults", Journal of Pharmacy Practice, 2012, vol. 26, No. 4, pp. 389-396.

Oldehinkel et al., "Urinary free cortisol excretion in elderly persons with minor and major depression", Psychiatry Research, 2011, vol. 104, pp. 39-47.

Olino et al., "Latent trajectory classes of depressive and anxiety disorders from adolescence to adulthood: descriptions of classes and associate with risk factors", Comprehensive Psychiatry, May 2010, vol. 51, No. 3, pp. 224-235.

Oosterwijk et al, "States of mind: Emotions, body feelings, and thoughts share distributed neural networks", NeuroImage, 2012, vol. 62, pp. 2110-2128.

Opsahl, "Software for analysis of weighted, two-mode, and longitudinal networks, package", Nov. 18, 2015, 48 pgs.

Opsahl, "Structure and evolution of weighted networks", Queen Mary, University of London, 2009, thesis, 151 pgs.

O'Reilly et al., "Tools of the trade: psychophysiological interactions and functional connectivity", Social Cognitive and Affective Neuroscience, Jun. 2012, Published online May 7, 2012, vol. 7, No. 5, pp. 604-609.

Oskooilar et al., "Body Mass Index and Response to Antidepressants in Depressed Research Subjects", J. Clin. Psychiatry, Nov. 2009, vol. 70, No. 11, pp. 1609-1610.

Oswald et al., "History of childhood adversity is positively associated with ventral striatal dopamine responses to amphetamine", Psychopharmacology, 2014, vol. 231, pp. 2417-2433.

Ottaviani et al., "Amygdala responses to masked and low spatial frequency fearful faces: a preliminary fMRI study in panic disorder", Psychiatry Research: Neuroimaging, 2012, vol. 203, pp. 159-165.

Palm et al., "Attenuated responses to emotional expressions in women with generalized anxiety disorder", Psychological Medicine, 2011, vol. 41, pp. 1009-1018.

Papakostas, "Cognitive Symptoms in Patients with Major Depressive Disorder and Their Implications for Clinical Practice", J. Clin. Psychiatry, 2014, vol. 75, No. 1, pp. 8-14.

(56) References Cited

OTHER PUBLICATIONS

Papakostas et al., "Obesity among outpatients with major depressive disorder", International Journal of Neuropsychopharmacology, 2005, vol. 8, pp. 59-63.
Parker, "Defining melancholia: the primacy of psychomotor disturbance", Acta Psychiatrica Scandinavica, 2007, vol. 115, Suppl. 433, pp. 21-30.
Parker et al., "Classifying Depression by Mental State Signs", British Journal of Psychiatry, 1990, vol. 157, pp. 55-65.
Parker et al., "Gender differences in response to differing antidepressant drug classes: two negative studies", Psychological Medicine, 2003, vol. 33, pp. 1473-1477.
Parker et al., "Sub-typing depression, III. Development of a clinical algorithm for melancholia and comparison with other diagnostic measures", Psychological Medicine, 1995, vol. 25, pp. 833-840.
Patenaude et al., "A Bayesian model of shape and appearance for subcortical brain segmentation", NeuroImage, 2011, vol. 56, pp. 907-922.
Patton et al., "Factor Structure of the Barratt Impulsiveness Scale", Journal of clinical Psychology, Nov. 1995, vol. 51, No. 6, pp. 768-774.
Paul et al., "Age-Dependent Change in Executive Function and Gamma 40 HZ Phase Synchrony", Journal of Integrative Neuroscience, Apr. 2005, vol. 4, No. 1, pp. 63-76.
Paul et al., "Cross-Cultural Assessment of Neuropsychological Performance and Electrical Brain Function Measures: Additional Validation of an International Brain Database", International Journal of Neuroscience, Jul. 7, 2009, vol. 117, No. 4, pp. 549-568.
Paul et al., "Preliminary Validity of "Integneuro": A New Computerized Battery of Neurocognitive Tests", International Journal of Neuroscience, 2005, vol. 115, pp. 1549-1567, published online Jul. 7, 2009.
Pavlenko et al., "EEG Correlates of Anxiety and Emotional Stability in Adult Healthy Subjects", Neurophysiology, 2009, vol. 41, No. 5, pp. 337-345.
Peles et al., "MDR1 gene polymorphism: therapeutic response to paroxetine among patients with major depression", Progress in Neuro-Psychopharmacology & Biological Psychiatry, 2008, vol. 43, pp. 1439-1444.
Peluso et al., "Amygdala hyperactivation in untreated depressed individuals", Psychiatry Research: Neuroimaging, 2009, vol. 173, pp. 158-161.
Penza et al., "Neurobiological effects of childhood abuse: implications for the pathophysiology of depression and anxiety", Arch. Womens Mental Health, 2003, vol. 6, pp. 15-22.
Peper et al., "Genetic Influences on Human Brain Structure: A Review of Brain Imaging Studies in Twins", Human Brain Mapping, 2007, vol. 28, pp. 464-473.
Perlis et al., "Failure to Replicate Genetic Associations with Antidepressant Treatment Response in Duloxetine-Treated Patients", Biol. Psychiatry, 2010, vol. 67, pp. 1110-1113.
Peterson et al., "Resting-State Neuroimaging Studies: A New Way of Identifying Differences and Similarities Among the Anxiety Disorders?", The Canadian Journal of Psychiatry, Jun. 2013, vol. 59, No. 6, pp. 294-300.
Phan et al., "Association between Amygdala Hyperactivity to Harsh Faces and Severity of Social Anxiety in Generalized social Phobia", Biol. Psychiatry, 2006, vol. 50, pp. 424-429.
Phan et al., "Cortocolimbic Brain Reactivity to Social Signals of Threat Before and After Sertraline Treatment in Generalized Social Phobia", Biol. Psychiatry, 2013, vol. 73, pp. 329-336.
Phelps et al., "Contributions of the amygdala to emotion processing: From animal models to human behavior", Neuron, Oct. 20, 2005, vol. 48, pp. 175-187.
Phillips et al., "Neurobiology of Emotion Perception II: Implications for Major Psychiatric Disorders", Biol. Psychiatry, 2003, vol. 54, pp. 515-528.
Piccirillo et al., "High Plasma Concentrations of Cortisol and Thromboxane B2 in Patients with Depression", Am. J. Med. Sci., 1994, vol. 307, No. 3, pp. 228-232.

Pier et al., "Differential patterns of psychomotor functioning in unmedicated melancholic and nonmelancholic depressed patients", Journal of Psychiatric Research, 2004, vol. 38, pp. 425-435.
Pizzagalli et al., "Frontocingulate Dysfunction in Depression: Toward Biomarkers of Treatment Response", Neuropsychopharmacology Reviews, 2011, vol. 36, pp. 183-206, published online Sep. 22, 2010.
Pizzagalli et al., "Functional but not structural subgenual prefrontal cortex abnormalities in melancholia", Molecular Psychiatry, 2004, vol. 9, pp. 393-405.
Pizzagalli et al., "Reduced Caudate and Nucleus Accumbens Response to Rewards in Unmedicated Individual with Major Depressive Disorder", Am. J. Psychiatry, 2009, vol. 166, pp. 702-710.
Pizzagalli et al., "Resting Anterior Cingulate Activity and Abnormal Responses to Errors in Subjects with Elevated Depressive Symptoms: A 128-Channel EEG Study", Human Brain Mapping, Mar. 2006, vol. 27, No. 3, pp. 185-201.
Posener et al., "24-Hour Monitoring of Cortisol and Corticotropin Secretion in Psychotic and Nonpsychotic Major Depression", Archives of General Psychiatry, Aug. 2000, vol. 57, No. 8, pp. 755-760.
Posner, "Measuring alertness", Acad Sci 1129, pp. 193-199, 2008.
Power et al., "Functional Network Organization of the Human Brain", Neuron, Nov. 17, 2011, vol. 72, pp. 665-678.
Power et al., "Methods to detect, characterize, and remove motion artifact in resting state fMRI", NeuroImage, 2014, available online Aug. 29, 2013, vol. 84, pp. 320-341.
Power et al., "Spurious but systematic correlations in functional connectivity MRI networks arise from subject motion", NeuroImage, Feb. 1, 2012, available online Oct. 14, 2011, vol. 59, Issue 3, pp. 2142-2154.
Prater et al., "Aberrant Amygdala-Frontal Cortex connectivity During Perception of Fearful Faces and at Rest in Generalized Social Anxiety Disorder", Depression and Anxiety, 2013, published online Nov. 26, 2012, vol. 30, pp. 234-241.
Price et al., "Data-Driven Subgroups in Depression Derived from Directed Functional Connectivity Paths at Rest", Neuropsychopharmacology, May 2017, vol. 42, pp. 2623-2632.
Price et al., "Neuocircuitry of Mood Disorders", Neuropsychopharmacology Reviews, 2010, vol. 35, pp. 192-216.
Price et al., "Parsing Heterogeneity in the Brain Connectivity of Depressed and Healthy Adults During Positive Mood", Biological Psychiatry, Feb. 15, 2017, vol. 81, pp. 347-357.
Qin et al., "Abnormal Brain Anatomical Topological Organization of the Cognitive-Emotional and the Frontoparietal Circuitry in Major Depressive Disorder", Magnetic Resonance in Medicine, 2014, published online Nov. 22, 2013, vol. 72, pp. 1397-1407.
Qiu et al., "Regional homogeneity changes in social anxiety disorder: A resting-state fMRI study", Psychiatry Research: Neuroimaging, 2011, 194, pp. 47-53.
Quinn et al., "The impact of depression heterogeneity on cognitive control in major depressive disorder", Australian & New Zealand Journal of Psychiatry, vol. 46, No. 11, pp. 1079-1088, DOI:10.1177/0004867412461383.
Quinn et al., "The impact of depression heterogeneity on inhibitory control", Australian & New Zealand Journal of Psychiatry, vol. 46, No. 4, 2012, pp. 374-383, DOI: 10.1177/0004867411432073.
Quinn et al., "The Interdependence of Subtype and Severity: Contributions of Clinical and Neuropsychological Features to Melancholia and Non-melancholia in an Outpatient Sample", Journal of the International Neuropsychological Society, 2012, vol. 18, pp. 361-369.
R. Development Core Team, "A Language and Environment for Statistical Computing", Foundation for Statistical Computing, Vienna, 2008.
Rabellino et al., "Intrinsic Connectivity Networks in post-traumatic stress disorder during sub- and supraliminal processing of threat-related stimuli", Acta Psychiatrica Scandinavica, 2015, vol. 132, pp. 365-378.
Raichle et al., "A default mode of brain function", PNAS, Jan. 16, 2001, vol. 98, No. 2, pp. 676-682.
Raichle et al., "The Brain's Default Mode Network", Annu. Rev. Neurosci., 2015, published online May 4, 2015, vol. 38, pp. 433-447.

(56) References Cited

OTHER PUBLICATIONS

Rao et al., "Genetic Variation in Serotonin Transporter Alters Resting Brain Function in Healthy Individuals", Biol. Psychiatry, 2007, vol. 62, pp. 600-606.
Rao et al., "Path Analysis in Genetic Epidemiology", Encyclopedia of Life Sciences, Advanced Article, doi: 10.1038/npg.els.0005438, Jan. 27, 2006, pp. 1-7.
Ray et al., "ABCB1 (MDR1) predicts remission on P-gp substrates in chronic depression", The Pharmacogenomics Journal, 2015, published online Dec. 9, 2014, vol. 15, pp. 332-339.
Raz, "Typologies of attentional networks", Nat. Rev. Neurosci, vol. 7, No. 5, pp. 367-379, 2006.
Rebbeck et al., "Assessing The Function of Genetic Variants in Candidate Gene Association Studies", Nature Reviews | Genetics, Aug. 2004, vol. 5, pp. 589-597.
Reppermund et al., "Cognitive impairment in unipolar depression is persistent and non-specific: further evidence for the final common pathway disorder hypothesis", Psychological Medicine, 2009, vol. 39, pp. 603-614.
Rhebergen et al., "Course trajectories of unipolar depressive disorders identified by latent class growth analysis", Psychological Medicine, Jul. 2012, vol. 42, No. 7, pp. 1383-1396.
Risbrough, "Behavioral Correlates of Anxiety", Current Topics in Behavioral Neurosciences, Behavioral Neurobiology of Anxiety and Its Treatment, Jan. 2010, TOC, 205-228.
Roalf et al., "Neuroimaging Predictors of Cognitive Performance Across a Standardized Neurocognitive Battery", Neuropsychology, 2014, vol. 28, No. 2, pp. 161-176.
Roalf et al., "Neuroimaging predictors of cognitive performance across a standardized neurocognitive battery", NIH Public Access—Author Manuscript, 30 pgs., published in final form as Neuropsychology, Mar. 2014, vol. 28, No. 2, pp. 161-176, doi:10.1037/neu0000011.
Robinson et al., "Depression Treatment in Primary Care", Depression Treatment in Primary Care, JABFP, Mar.-Apr. 2005, vol. 18, No. 2, pp. 79-86.
Robinson et al., "The dorsal medial prefrontal (anterior cingulate) cortex-amygdala aversive amplification circuit in unmedicated generalised and social anxiety disorders: an observational study", Lancet Psychiatry, 2014, vol. 1, pp. 294-302, published online Aug. 27, 2014.
Rocca et al., "Default-mode network dysfunction and cognitive impairment in progressive MS", Neurology, Apr. 20, 2010, vol. 74, pp. 1252-1259.
Rogers et al., "Mental Rotation in Unipolar Major Depression", Journal of Clinical and Experimental Neuropsychology, 2002, published online Aug. 9, 2010, vol. 24, No. 1, pp. 101-106.
Rogers et al., "Parkinsonian Motor Characteristics in Unipolar Major Depression", Journal of Clinical and Experimental Neuropsychology, 2000, vol. 22, No. 2, pp. 232-244.
Rogers et al., "Reliance on external cues during serial sequential movement in major depression", J. Neurol. Neurosurg. Psychiatry, 2000, vol. 6 9, pp. 237-239.
Rogers et al., "Response Selection Deficits in Melancholic but not Nonmelancholic Unipolar Major Depression", Journal of Clinical and Experimental Neuropsychology, 2004, vol. 26, No. 2, pp. 169-179.
Rose et al., "Limbic over-activity in depression during preserved performance on the n-back task", NeuroImage, 2006, available online Sep. 12, 2005, vol. 29, pp. 203-215.
Rubinov et al., "Complex network measures of brain connectivity: Use and interpretations", NeuroImage, 2010, available online Oct. 9, 2009, vol. 52, pp. 1059-1069, available online Oct. 9, 2009.
Rubinow et al., "Cortisol Hypersecretion and Cognitive Impairment in Depression", Arch. Gen. Psychiatry, 1984, vol. 41, pp. 279-283.
Ruhe et al., "Successful Pharmacologic Treatment of Major Depressive Disorder Attenuates Amygdala Activation to Negative Facial Expressions: A Functional Magnetic Resonance Imaging Study", J. Clin. Psychiatry, 2012, published online Aug. 9, 2011, vol. 74, No. 4, pp. 451-459.
Rush et al., "An Evaluation of the Quick Inventory of Depressive Symptomatology and the Hamilton Rating Scale for Depression: A Sequenced Treatment Alternatives to Relieve Depression Trial Report", Biol. Psychiatry, 2006, vol. 59, pp. 493-501.
Rush et al., "Melancholic Symptom Features and DSM-IV", American Journal Psychiatry, Apr. 1994, vol. 151, No. 4, pp. 489-498.
Rush et al., "Selecting Among Second-Stop Antidepressant Medication Monotherapies", Arch. Gen. Psychiatry, Aug. 2008, vol. 65, No. 8, pp. 870-881.
Rush et al., "The 16-Item Quick Inventory of Depressive Symptomatology (QIDS), Clinician Rating (QIDS-C), and Self-Report (QIDS-SR): A Psychometric Evaluation in Patients with Chronic Major Depression", Biol. Psychiatry, 2004, vol. 54, pp. 573-583.
Rushworth et al., "Are there specialized circuits for social cognition and are they unique to humans?", Current Opinion in Neurobiology, 2013, vol. 23, pp. 436-442, available online Jan. 2, 2013.
Sachdev et al., "Slowness of Movement in Melancholic Depression", Biol. Psychiatry, 1994, vol. 35, pp. 253-262.
Sachet et al., "Characterizing white matter connectivity in major depressive disorder: automated fiber quantification and maximum density paths", IEEE International Symposium on Biomedical Imaging, 11, 2014, pp. 592-595.
Sagud et al., "Gender Differences in Depression", Coll. Antropol, 2002, vol. 26, pp. 149-157.
Sagud et al., "The lack of association between components of metabolic syndrome and treatment resistance in depression", Psychopharmacology, 2013, published online Apr. 12, 2013, vol. 230, pp. 15-21, published online Apr. 12, 2013.
Sambataro et al., "Age-related alterations in default mode network: Impact on working memory performance", Neurobiology of Aging, May 1, 2010, available online Jul. 31, 2008, vol. 31, No. 5, pp. 839-852.
Sanchez et al., "A comparative review of escitalopram, paroxetine, and sertraline. Are they all alike?", Int. Cain. Psychopharmacol, vol. 29, No. 4, pp. 185-196.
Sanders et al., "The Measurement of Psychological Maltreatment: Early Data on the Child Abuse and Trauma Scale", Child Abuse & Neglect, 1995, vol. 19, No. 3, pp. 315-323.
Sarginson et al., "ABCB1 (MDR1) polymorphisms and antidepressant response in geriatric depression", Pharmacogenetics and Genomics, 2010, vol. 20, No. 8, pp. 467-475.
Sartory et al., "In Search of the Trauma Memory: A Meta-Analysis of Functional Neuroimaging Studies of Symptom Provocation in Posttraumatic Stress Disorder (PTSD)", PLoS ONE, Mar. 2013, vol. 8, Issue 3, e58150, pp. 1-11.
Saveanu et al., "The International Study to Predict Optimized Treatment in Depression (iSPOT-D): Outcomes from the acute phase of antidepressant treatment", Journal of Psychiatric Research, Feb. 2015, vol. 61, pp. 1-12.
Saxena et al., "Differential Brain Metabolic Predictors of Response to Paroxetine in Obsessive-Compulsive Disorder Versus Major Depression", Am. J. Psychiatry, 2003, vol. 160, pp. 522-532.
Schatzberg, "ABCB-1: Antidepressant Response in Geriatric Depression and Chronic Depression", Biol. Psychiatry, 2014, vol. 75, No. 1S-401S, p. 23S.
Schatzberg et al., "ABCB1 Genetic Effects on Antidepressant Outcomes: A Report From the iSPOT-D Trial", Am. J. Psychiatry, vol. 172, No. 8, Aug. 2015, pp. 751-759.
Schatzberg et al., "HPA axis genetic variation, cortisol and psychosis in major depression", Molecular Psychiatry, 2014, published online Oct. 29, 2013, vol. 19, pp. 220-227.
Schmidt et al., "Early life stress paradigms In rodents: Potential animal models of depression?", Psychopharmacology, 214(1): 131-140, 2011.
Schoning et al., "Working-Memory fMRI Reveals Cingulate Hyperactivation in Euthymic Major Depression", Human Brain Mapping, 2009, published online Dec. 11, 2008, vol. 30, pp. 2746-2756.
Schout, "Measurement reliability and agreement in psychiatry", Statistical Methods in Medical Research, 1998, vol. 7, pp. 301-317.
Schriener et al., "Default mode network connectivity and reciprocal social behavior in 22q11.2 deletion syndrome", Scan, 2014, advance publication Aug. 2, 2013, vol. 9, pp. 1261-1267.

(56) References Cited

OTHER PUBLICATIONS

Schule et al., "The Combined Dexamethasone/CRH Test (DEX/CRH Test) and Prediction of Acute Treatment Response in Major Depression", PLoS ONE, Jan. 2009, vol. 5, Issue 1, e4324, pp. 1-12.
Schwarz et al., "Cognition and the Placebo Effect—Dissociating Subjective Perception and Actual Performance", PLOS One, Jul. 6, 2015, vol. 10, No. 7, DOI:10.1371/journal.pone.0130492, pp. 1-12.
Seeley et al., "Dissociable Intrinsic Connectivity Networks for Salience Processing and Executive Control", The Journal of Neuroscience, Feb. 28, 2007, vol. 27, No. 9, pp. 2349-2356.
Shamseddeen et al., "Impact of Physical and Sexual Abuse on Treatment Response in the Treatment of Resistant Depression in Adolescent Study (TORDIA)", Journal of the American academy of Chile & Adolescent Psychiatry, Mar. 2011, vol. 50, No. 3, pp. 293-301.
Shanmugan et al., "Common and Dissociable Mechanisms of Executive System Dysfunction Across Psychiatric Disorders in Youth", American Journal of Psychiatry, May 1, 2016, vol. 173, No. 5, pp. 517-526.
Sheehan et al., "The Mini-International Neuropsychiatric Interview (M.I.N.I.): The Development and Validation of a Structured Diagnostic Psychiatric Interview for DSM-IV and ICD-10", J. Clin. Psychiatry, 1998, vol. 59 (suppl. 20), pp. 22-33.
Shehzad et al., "The Resting Brain: Unconstrained yet Reliable", Cerebral Cortex, Oct. 2009, vol. 19, pp. 2209-2229, advance access publication Feb. 16, 2009.
Sheline et al., "APOE4 Allele Disrupts Resting State fMRI Connectivity in the Absence of Amyloid Plaques or Decreased CSF Aβ42", The Journal of Neuroscience, Dec. 15, 2010, vol. 30, No. 50, pp. 17035-17040.
Sheline et al., "Increased Amygdala Response to Masked Emotional Faces in Depressed Subject Resolves with Antidepressant Treatment: An fMRI Study", Biol. Psychiatry, Dec. 2001, vol. 50, pp. 651-658.
Sheline et al., "Resting-state functional MRI in depression unmasks increased connectivity between networks via the dorsal nexus", PNAS, Jun. 15, 2010, vol. 107, No. 24, pp. 11020-11025.
Sheline et al., "The default mode network and self-referential processes in depression", PNAS, Feb. 10, 2009, vol. 106, No. 6, pp. 1942-1947.
Shelton, "Steps Following Attainment of Remission: Discontinuation of Antidepressant Therapy", Primary Care Companion J. Clin. Psychiatry, 2001, vol. 3, No. 4, pp. 168-174.
Shelton et al., "Can recovery from depression be achieved?", Psychiatric Services, vol. 52, No. 11, 2001, pp. 1469-1478.
Shepard et al., "Corticosterone delivery to the amygdala increases corticotropin-releasing factor mRNA in the central amygdaloid nucleus and anxiety-like behavior", Brain Research, May 2000, vol. 861, No. 2, pp. 288-295.
Shilyansky et al., "Effects of antidepressant treatment on cognitive impairments associated with depression: a randomised longitudinal study", HHS Public Access—Author manuscript, , 21 pgs., published in final form as Lancet Psychiatry, vol. 3, No. 5, May 2016, pp. 425-435, doi:10.1016/S2215-0366(16)00012-2.
Shirk et al., "Prediction of Treatment Outcome from Relationship Variables in Child and Adolescent Therapy: A Meta-Analytic Review", Journal of Consulting and Clinical Psychology, 2-4, vol. 71, No. 3, 2003, pp. 452-464.
Shulman et al., "Common Blood Flow Changes across Visual Tasks: II. Decreases in Cerebral Cortex", Journal of Cognitive Neuroscience, Oct. 1997, vol. 9, No. 5, pp. 648-663.
Siegel et al., "Statistical Improvements in Functional Magnetic Resonance Imaging Analyses Produced by Censoring High-Motion Data Points", Human Brain Mapping, May 2014, published online Jul. 17, 2013, vol. 35, No. 5, pp. 1981-1996.
Siegle, "Beyond Depression Commentary: Wherefore Art Thou, Depression Clinic of Tomorrow", NIH Public Access—Author Manuscript, 7 pgs., published in final form as Clin. Psychol. (New York), Dec. 2011, vol. 18, No. 4, pp. 305-310, doi: 10.1111/j.1468-2850.2011.01261.x.
Siegle et al., "Beyond Depression Commentary: Wherefore Art Thou, Depression Clinic of Tomorrow?", Clinical Psychology Science and Practice, 2011, vol. 18, pp. 305-310.
Siegle et al., "Increased Amygdala and Decreased Dorsolateral Prefrontal BOLD Responses in Unipolar Depression: Related and Independent Features", Biol. Psychiatry, 2007, vol. 61, pp. 198-209.
Siegle et al., "Use of fMRI to Predict Recovery from Unipolar Depression with Cognitive Behavior Therapy", Am. J. Psychiatry, 2006, vol. 163, pp. 735-738.
Singh et al., "ABCB1 polymorphism predicts escitalopram dose needed for remission in major depression", Translational Psychiatry, 2012, vol. 2, No. e198, published online Nov. 27, 2012, 6 pgs.
Singh et al., "Anomalous Gray Matter Structural Networks in Major Depressive Disorder", NIH Public Access—Author Manuscript, 18 pgs., published in final form as Biol. Psychiatry, Nov. 15, 2013, vol. 74, No. 10, pp. 777-785, doi: 10.1016j. biopsych.2013.03.005.
Singh et al., "Antidepressant pharmacogenetics", Current Opinion Psychiatry, 2014, vol. 27, pp. 43-51.
Sladky et al., "Disrupted Effective Connectivity Between the Amygdala and Orbitofrontal Cortex in Social Anxiety Disorder During Emotion Discrimination Revealed by Dynamic Casual Modeling for fMRI", Cerebral Cortex, Apr. 2015, Advance Access publication Oct. 9, 2013, vol. 25, pp. 895-903.
Snyder, "Major Depressive Disorder Is Associated with Broad Impairments on Neuropsychological Measures of Executive Function: A Meta-Analysis and Review", Psychological Bulletin, 2013, vol. 139, No. 1, pp. 81-132.
Soares et al., "A Hitchhiker's Guide to Functional Magnetic Resonance Imaging", Frontiers in Neuroscience, 2016, vol. 10, published online Nov. 10, 2016, 58 pgs.
Somers et al., "Prevalence and Incidence Studies of Anxiety Disorders: A Systematic Review of the Literature", Can. J. Psychiatry, Feb. 2006, vol. 51, pp. 100-113.
Sotiropoulos et al., "Advances in diffusion MRI acquisition and processing in the Human Connectome Project", NeuroImage, 2013, available online May 20, 2013, vol. 80, pp. 125-143.
Spencer et al., "Failure to deactivate the default mode network indicates a possible endophenotype of autism", Molecular Autism, 2012, vol. 3, No. 15, 8 pgs.
Spreng et al., "Intrinsic Architecture Underlying the Relations Among the Default, Dorsal Attention and Frontoparietal Control Networks of the Human Brain", Journal of Cognitive Neuroscience, Aug. 2012, vol. 25, No. 1, pp. 74-86.
Sprengelmeyer et al., "The insular cortex and the neuroanatomy of major depression", Journal of Affective Disorders, 2011, vol. 133, pp. 120-127.
Steckler et al., "Corticotropin-Releasing Hormone Receptor Subtypes and Emotion", Biol. Psychiatry, 1999, vol. 46, pp. 1480-1508.
Steele et al., "Prefrontal cortical functional abnormality in major depressive disorder: A stereotactic metal-analysis", Journal of Affective Disorders, 2007, available online Dec. 15, 2006, vol. 101, pp. 1-11.
Steffens et al., "Structural Integrity of the Uncinate Fasciculus and Resting State Functional Connectivity of the Ventral Prefrontal Cortex in Late Life Depression", PLoS ONE, Jul. 2011, vol. 6, Issue 7, e22697, pp. 1-6.
Stein et al., "Increased Amygdala Activation to Angry and Contemptuous Faces in Generalized Social Phobia", Arch. Gen. Psychiatry, 2002, vol. 59, pp. 1027-1034.
Stern et al., "Resting-State Functional Connectivity between Fronto-Parietal and Default Mode Networks in Obsessive-Compulsive Disorder", PLoS ONE, May 3, 2012, vol. 7, Issue 5, e36356, pp. 1-9.
Stewart et al., "Resting and Task-Elicited Prefrontal EEG Alpha Asymmetry in Depression: Support for the Capability Model", NIH Public Access—Author Manuscript, 18 pgs., published in final form as Psychophysiology, May 2014, vol. 51, No. 5, pp. 446-455, doi:10.1111.psyp.12191.
Stroop, "Studies of Interference in Serial Verbal Reactions", Journal of Experimental Psychology, Dec. 1935, vol. XVIII, No. 6, pp. 643-662.

(56) References Cited

OTHER PUBLICATIONS

Stuhrmann et al., "Facial emotion processing in major depression: systematic review of neuroimaging findings", Biology of Mood & Anxiety Disorders, 2011, vol. 1, No. 10, pp. 1-17.
Stuhrmann et al., "Mood-congruent amygdala responses to subliminally presented facial expressions in major depression: associates with anhedonia", Journal of Psychiatry Neuroscience, 2013, vol. 38, No. 4, pp. 249-258.
Sun et al., "Two Patterns of White Matter Abnormalities in Medication-Naive Patients with First-Episode Schizophrenia Revealed by Diffusion Tensor Imaging and Cluster Analysis", JAMA Psychiatry, May 2015, vol. 72, No. 7, pp. 678-686.
Surguladze et al., "A Differential Pattern of Neural Response Toward Sad Versus Happy Facial Expressions in Major Depressive Disorder", Biol. Psychiatry, 2005, vol. 57, pp. 201-209.
Surguladze et al., "Recognition Accuracy and Response Bias to Happy and Sad Facial Expressions in Patients with Major Depression", Neuropsychology, 2004, vol. 19, No. 2, pp. 212-218.
Suslow et al., "Automatic Mood-Congruent Amygdala Responses to Masked Facial Expressions in Major Depression", Biol. Psychiatry, 2010, vol. 67, pp. 155-160.
Suzuki et al., "Early Life Stress and Trauma and Enhanced Limbic Activation to Emotionally Valenced Faces in Depressed and Healthy Children", NIH Public Access—Author manuscript, 23 pgs., published in final form as J. Am. Acad. Child Adoles. Psychiatry, Jul. 2014, vol. 53, No. 7, pp. 800-813, e10, doi: 10.1016/j.jaac.2014.04.013.
Swartz et al., "A Neural Biomarker of Psychological Vulnerability to Future Life Stress", Neuron, Feb. 4, 2015, vol. 85, pp. 505-511.
Sylvester et al., "Functional network dysfunction in anxiety and anxiety disorders", Trends in Neurosciences, Sep. 2012, vol. 35, No. 9, pp. 527-535.
Szegedy et al., "Going Deeper with Convolutions", CVPR2015 paper, provided by the Computer Vision Foundation, 2015, 9 pgs.
Tamminga et al., "Bipolar and Schizophrenia Network for Intermediate Phenotypes: Outcomes Across the Psychosis Continuum", Schizophrenia Bulletin, Feb. 20, 2014, vol. 40, Suppl. No. 2, pp. S131-S137.
Tan et al., "Epistasis between catechol-O-methyltransferase and type II metabotropic glutamate receptor 3 genes on working memory brain function", PNAS, Jul. 24, 2007, vol. 104, No. 30, pp. 12536-12541.
Tazzite et al., "Association between ABCB1 C3435T polymorphism and breast Cancer risk: a Moroccan case-control study and meta-analysis", BMC Genetics, 2016, vol. 17, No. 126, pp. 1-11.
The WHOQOL Group, "Development of the World Health Organization WHOQOL-BREF Quality of Life Assessment", Psychological Medicine, 1998, vol. 28, pp. 551-558.
Thibodeau et al., "Depression, Anxiety, and Resting Frontal EEG Asymmetry: A Meta-Analytic Review", Journal of Abnormal Psychology, 2006, vol. 115, No. 4, pp. 715-729.
Thiels et al., "Gender differences in routine treatment of depressed outpatients with the selective serotonin reuptake inhibitor sertraline", International Clinical Psychopharmacology, 2005, vol. 20, No. 1, pp. 1-7.
Thirion et al., "Which fMRI clustering gives good brain parcellations?", Frontiers in Neuroscience, Jul. 1, 2014, https://doi.org.10.3389/fnins.2014.00167, 37 pgs.
Thomas et al, "Amygdala Response to Fearful Faces in Anxious and Depressed Children", Arch. Gen. Psychiatry, Nov. 2001, vol. 58, pp. 1057-1063.
Thomas et al., "Brain imaging correlates of cognitive impairment in depression", Frontiers in Human Neuroscience, Oct. 9, 2009, vol. 3, Article 30, pp. 1-9.
Tibshirani et al., "Estimating the number of clusters in a data set via the gap statistic", J. R. Statist. Soc. B, 2001, vol. 63, Part 2, pp. 411-423.
Tibshirani et al., "Pre-validation and inference in microarrays", Statistical Applications in genetics and Molecular Biology, Aug. 2002, vol. 1, Issue 1, Article 1, 20 pgs.

Toornvliet et al., "Effect of age on functional P-glycoprotein in the blood-brain barrier measured by use of (R)-[11C]verapamil and positron emission tomography", Clinical Pharmacology & Therapeutics, 2006, vol. 79, No. 6, pp. 540-548.
Toups et al., "Relationship Between Obesity and Depression: Characteristics and Treatment Outcomes with Antidepressant Medication", Psychosomatic Medicine, 2013, vol. 75, pp. 863-872.
Touroutoglou et al., "Brain Network Connectivity—Behavioral Relationships Exhibit Trait-Like Properties: Evidence from Hippocampal Connectivity and Memory", Hippocampus, 2015, vol. 25, pp. 1591-1598.
Townsend et al., "fMRI activation in amygdala and orbitofrontal cortex in unmedicated subjects with major depressive disorder", NIH Public Access, Author Manuscript, 22 pgs., final form: Psychiatry Res., Sep. 30, 2010, vol. 183, No. 3, pp. 209-217, doi:10.1016/j.psychresns.2010.06.001.
Townsend et al., "fMRI activation in the amygdala and the orbitofrontal cortex in unmedicated subjects with major depressive disorder", Psychiatry Research: Neuroimaging, 2010, vol. 183, pp. 209-217.
Treadway et al., "Effort-Based Decision-Making in Major Depressive Disorder: A Translational Model of Motivational Anhedonia", Journal of Abnormal Psychology, 2012, vol. 121, No. 3, pp. 553-558.
Treadway et al., "Reconsidering anhedonia in depression: Lessons from translational neuroscience", Neuroscience and Biobehavioral Reviews, 2011, vol. 35, pp. 537-555.
Trestman et al., "Diurnal Neuroendocrine and Autonomic Function in Acute and Remitted Depressed Male Patients", Biol. Psychiatry, 1995, vol. 37, pp. 448-456.
Trivedi et al., "Evaluation of outcomes with citalopram for depression using measurement-based care in STAR*D: implications for clinical practice", Am. J. Psychiatry, vol. 163, No. 1,2006, pp. 28-40.
Turner et al., "Transcriptional control of the glucocorticoid receptor: CpG islands, epigenetics and more", Biochemical Pharmacology, 2010, vol. 80, pp. 1860-1868.
Tye et al., "Amygdala circuitry mediating reversible and bidirectional control of anxiety", Nature, Mar. 17, 2011, vol. 471, pp. 358-362.
Tzourio-Mazoyer et al., "Automated Anatomical Labeling of SPM Using a Macroscopic Anatomical Parcellation of the MNI MRI Single-Subject Brain", NeuroImage, 2002, vol. 15, pp. 273-289.
Uher et al., "Body weight as a predictor of antidepressant efficacy in the GENDEP project", Journal of Affective Disorders, 2009, available online Mar. 9, 2009, vol. 118, pp. 147-154.
Uhr et al., "Differential Enhancement of Antidepressant Penetration into the Brain in Mice with abcb1ab (mdr1ab) P-Glycoprotein Gene Disruption", Biol. Psychiatry, 2003, vo. 54, pp. 840-846.
Uhr et al., "Polymorphisms in the Drug Transporter Gene ABCB1 Predict Antidepressant Treatment Response in Depression", Neuron, Jan. 24, 2008, vol. 57, pp. 203-209.
Van De Ven et al., "Functional Connectivity as Revealed by Spatial Independent Component Analysis of fMRI Measurements During Rest", Human Brain Mapping, 2004, vol. 22, pp. 165-178.
Van Den Heuvel et al., "Exploring the brain network: A review on resting-state fMRI functional connectivity", European Neuropsychopharmacology, 2010, vol. 20, pp. 519-534.
Van Den Heuvel et al., "Functionally Linked Resting-State Networks Reflect the Underlying Structural Connectivity Architecture of the Human Brain", Human Bran Mapping, 2009, published online Feb. 23, 2009, vol. 30, pp. 3127-3141.
Van Den Heuvel et al., "Genetic control of functional brain network efficiency in children", European Neuropsychopharmacology, 2013, vol. 23, pp. 19-23.
Van Den Heuvel et al., "Microstructural Organization of the Cingulum Tract and the Level of Default Mode Functional Connectivity", The Journal of Neuroscience, Oct. 22, 2008, vol. 28, No. 43, pp. 10844-10851.
Van Den Heuvel et al., "Network hubs in the human brain", Trends in Cognitive Sciences, Dec. 2013, vol. 17, No. 12, pp. 683-696.
Van Essen et al., "The Human Connectome Project: A data acquisition perspective", NeuroImage, 2012, available online Feb. 17, 2012, vol. 62, pp. 2222-2231.

(56) References Cited

OTHER PUBLICATIONS

Van Essen et al., "The WU-Minn Human Connectome Project: An Overview", NeuroImage, 2013, available online May 16, 2013, vol. 80, pp. 62-79.
Van Hulst et al., "Distinct neuropsychological profiles within ADHD: a latent class analysis of cognitive control, reward sensitivity and timing", Psychological Medicine, 2015, vol. 45, Issue 5, pp. 734-745.
Van Loo et al., "Data-driven subtypes of major depressive disorder: a systematic review", BMC Medicine, 2012, vol. 10, No. 156, pp. 1-12.
Van Loo et al., "Major depressive disorder subtypes to predict long-term course", HHS Public Access—Author manuscript, 22 pgs., published in final form as Depress. Anxiety, Sep. 2014, vol. 31, No. 9, pp. 765-777.
Vargas et al., "A systematic literature review of resting state network-functional MRI in bipolar disorder", Journal of Affective Disorders, 2013, available online Jul. 2, 2013, vol. 159, pp. 727-735.
Vasic et al., "Aberrant functional connectivity of dorsolateral prefrontal and cingulate networks in patients with major depression during working memory processing", Psychological Medicine, 2009, vol. 39, pp. 977-987.
Veatch et al., "Genetically meaningful phenotypic subgroups in autism spectrum disorders", Genes, Brain and Behavior, 2014, vol. 13, pp. 276-285.
Veer et al., "Whole brain resting-state analysis reveals decreased functional connectivity in major depression", Frontiers in Systems Neuroscience, Sep. 30, 2010, vol. 4, Article 41, pp. 1-10.
Veiel et al., "A preliminary profile of neuropsychological deficits associated with major depression", Journal of Clinical and Experimental Neuropsychology, 1997, vol. 19, No. 4, pp. 587-603, published online Jan. 4, 2008.
Victor et al., "Relationship Between Amygdala Responses to Masked Faces and Mood State and Treatment in Major Depressive Disorder", Arch. Gen. Psychiatry, Nov. 2010, vol. 67, No. 11, pp. 1128-1138.
Vilgis et al., "Frontoparietal function in young people with dysthymic disorder (DSM-5: Persistent depressive disorder) during spatial working memory", Journal of Affective Disorders, 2014, available online Mar. 7, 2014, vol. 160, pp. 34-42.
Villafeuerte et al., "Gene-Based SNP Genetic Association Study of the Corticotropin-Releasing Hormone Receptor-2 (CRHR2) in Major Depression", American Journal of Medical Genetics (Neuropsychiatric Genetics, Mar. 8, 2002, vol. 114, pp. 222-226.
Vincent et al., "Evidence for a Frontoparietal Control System Revealed by Intrinsic Functional Connectivity", J. Neurophysiol, Sep. 17, 2008, vol. 100, pp. 3328-3342.
Vogelzangs et al., "Inflammatory and Metabolic Dysregulation and the 2-Year Course of Depressive Disorders in Antidepressant Users", Neuropsychopharmacology, 2014, vol. 39, pp. 1624-1634, published online Feb. 12, 2014.
Vuilleumier et al., "Distributed and interactive bran mechanisms during emotion face perception: Evidence from functional neuroimaging", Neuropsychologia, 2007, available online Jul. 18, 2006, vol. 45, pp. 174-194.
Wacker et al., "The role of the nucleus accumbens and rostral anterior cingulate cortex in anhedonia: Integration of resting EEG, fMRI and volumetric techniques", NeuroImage, 2009, available online Feb. 6, 2009, vol. 46, pp. 327-337.
Wagner et al., "Cortical Inefficiency in Patients with Unipolar Depression: An Event-Related fMRI Study with the Stroop Task", Biol. Psychiatry, 2006, vol. 59, pp. 958-965.
Walter et al., "Increased left prefrontal activation in patients with unipolar depression: An event-related, parametric,, performance-controlled fMRI study", Journal of Affective Disorders, 2007, available online Jan. 2, 2007, vol. 101, pp. 175-185.
Wang et al., "Prefrontal mechanisms for executive control over emotional distraction are altered in major depression", Psychiatry Research: Neuroimaging, 2008, vol. 163, pp. 143-155.
Watson et al., "Testing a Tripartite Model: I. Evaluating the Convergent and Discriminant Validity of Anxiety and Depression Symptom Scales", Journal of Abnormal Psychology, 1995, vol. 104, No. 1, pp. 3-14.
Watters et al., "Negative Biases and Risk for Depression; Integrating Self-Report and Emotion Task Markers", Depression and Anxiety, 2011, vol. 28, pp. 703-718.
Weissman et al., "The Cross-national Epidemiology of Panic Disorder", Arch. Gen. Psychiatry, Apr. 1997, vol. 54, pp. 305-309.
Westfall et al., "The Preeminence of Early Life Trauma as a Risk Factor for Worsened Long-Term Health Outcomes in Women", Curr. Psychiatry Rep, 2015, published online Sep. 18, 2015, vol. 17, No. 90, pp. 1-18, published online Sep. 18, 2015.
Whalen et al., "A Functional Magnetic Resonance Imaging Predictor of Treatment Response to Venlafaxine in Generalized Anxiety Disorder", Biol. Psychiatry, 2008, vol. 63, pp. 858-863.
Whalen et al., "Functional Neuroimaging Studies of the Amygdala in Depression", Seminars in Clinical Neuropsychiatry, Oct. 2002, vol. 7, No. 4, pp. 234-242.
White et al., "Developing the Frith-Happe Animations: A Quick and Objective Test of Theory of Mind for Adults with Autism", Autism Research, 2011, vol. 4, pp. 149-154.
Whiteford et al., "Global burden of disease attributable to mental and substance use disorders: findings from the Global Burden of Disease Study 2010", Lancet, 2013, vol. 382, pp. 1575-1586, published online Aug. 29, 2013.
Whitfield-Gabrieli et al., "Default Mode Network Activity and Connectivity in Psychopathology", Annual Review Clinical Psychology, 2012, vol. 8, pp. 49-76, first published online Jan. 6, 2012.
Whitfield-Gabrieli et al., "Hyperactivity and hyperconnectivity of the default network in schizophrenia and in first-degree relatives of persons with schizophrenia", PNAS, Jan. 27, 2009, vol. 106, No. 4, pp. 1279-1284.
Whitton et al., "Reward processing dysfunction in major depression, bipolar disorder and schizophrenia", NIH Public Access—Author Manuscript, 11 pgs., published in final form as Curr. Opin. Psychiatry, Jan. 2015, vol. 28, No. 1, pp. 7-12, doi:10.1097/YCO.0000000000000122.
Widge et al., "Treating refractory mental illness with closed-loop brain stimulation: Progress towards a patient-specific transdiagnostic approach", Experimental Neurology, 2017, available online Jul. 30, 2016, vol. 287, pp. 461-472.
Williams, "Precision psychiatry: a neural circuit taxonomy for depression and anxiety", HHS Public Access—Author Manuscript, 18 pgs., published in final form as Lancet Psychiatry, May 2016, vol. 3, No. 5, pp. 472-480, doi:10.1016/S2215-0366(15)00579-9.
Williams, Leanne, "Defining biotypes for depression and anxiety based on large-scale circuit dysfunction: a theoretical review of the evidence and future directions for clinical translation", Depress Anxiety, vol. 34, 2017, Originally published Sep. 21, 2016, pp. 9-24.
Williams, Leanne, "Precision psychiatry: a neural circuit taxonomy for depression and anxiety", Lancet Psychiatry, 2016, Published online Apr. 14, 2016, 9 pgs.
Williams et al., "Amygdala Reactivity to Emotional Faces in the Prediction of General and Medication-Specific Responses to Antidepressant Treatment in the Randomized iSPOT-D Trial", Neuropsychopharmacology, vol. 40, 2015, published online Apr. 29, 2015, preview online Mar. 31, 2015, pp. 2398-2408.
Williams et al., "Amygdala-Prefrontal Dissociation of Subliminal and Supraliminal Fear", Human Brain Mapping, 2006, vol. 27, pp. 652-661.
Williams et al., "Childhood trauma predicts antidepressant response in adults with major depression: data from the randomized international study to predict optimized treatment for depression", Translational Psychiatry, 6, 2016, published online May 6, 2016, 7 pgs.
Williams et al., "Defining biotypes for depression and anxiety based on large-scale circuit dysfunction: A theoretical review of the evidence and future directions for clinical translation", HHS Public Access—Author manuscript, 29 pgs., published in final for as: Depress. Anxiety, Jan. 2017, vol. 34, No. 9, pp. 9-24, doi:10.1002/da/22556.

(56) References Cited

OTHER PUBLICATIONS

Williams et al., "Developing a clinical translational neuroscience taxonomy for anxiety and mood disorder: protocol for the baseline follow-up Research domain criteria Anxiety and Depression ("RAD") project", BMC Psychiatry, Mar. 2016, vol. 16, No. 68, 2016, 14 pgs.
Williams et al., "Dynamic Organization of the Emotional Brain: Responsivity, Stability, and Instability", The Neuroscientist, 2007, vol. 13, No. 4, pp. 349-370.
Williams et al., "Explicit identification and implicit recognition of facial emotions: I. Age effects in males and females across 10 decades", Journal of Clinical and Experimental Neuropsychology, 2009, vol. 31, No. 3, pp. 257-277, published online Mar. 23, 2009.
Williams et al., "General and social cognition in first episode schizophrenia: Identification of separable factors and prediction of functional outcome using the IntegNeuro test battery", Schizophrenia Research, 2008, available online Nov. 28, 2007, vol. 99,. pp. 182-191.
Williams et al., "International Study to Predict Optimized Treatment for Depression (iSPOT-D), a randomized clinical trial: rationale and protocol", Trials, 2011, vol. 12, No. 4, pp. 1-17.
Williams et al., "Mapping frontal-limbic correlates of orienting to change detection", Cognitive Neuroscience and Neuropsychology, Feb. 2007, vol. 18, No. 3, pp. 197-202.
Williams et al., "Mapping the Time Course of Nonconscious and Conscious Perception of Fear: an Integration of Central and Peripheral Measures", Human Brain Mapping, Feb. 2004, vol. 21, No. 2, pp. 64-74.
Williams et al., "Mode of Functional Connectivity in Amygdala Pathways Dissociates Level of Awareness for Signals of Fear", The Journal of Neuroscience, Sep. 6, 2006, vol. 26, No. 36, pp. 9264-9271.
Williams et al., "'Negativity bias' in risk for depression and anxiety: Brain-body fear circuitry correlates, 5-HTT-LPR and early life stress", NeuroImage, 2009, available online May 14, 2009, vol. 47, pp. 804-814.
Williams et al., "Sensitivity, specificity, and predictive power of the "Brief Risk-resilience Index for Screening," a brief pan-diagnostic web screen for emotional health", Brain and Behavior, 2012, vol. 2, No. 5, pp. 576-589.
Williams et al., "Using Brain-Based Cognitive Measures to Support Clinical Decisions in ADHA", Pediatric Neurology, 2010, vol. 42, No. 2., pp. 118-126.
Winograd-Gurvich et al., "Negative symptoms: A review of schizophrenia, melancholic depression and Parkinson's disease", Brain Research Bulletin, 2006, available online Jul. 5, 2006, vol. 70, pp. 312-321.
Wisniewski et al., "Self-Rated Global Measure of the Frequency, Intensity, and Burden of Side Effects", Journal of Psychiatric Practice, Mar. 2006, vol. 12, No. 2, pp. 71-79.
Withall et al., "A longitudinal study of cognitive function in melancholic and non-melancholic subtypes of Major Depressive Disorder", Journal of Affective Disorders, 2010, available online Aug. 20, 2009, vol. 123, pp. 150-157.
Woo et al., "Obesity and Its Potential Effects on Antidepressant Treatment Outcomes in Patients with Depressive Disorders: A Literature Review", International Journal of Molecular Sciences, 2016, vol. 17, No. 80, doi:10.3390/ijms17010080, 20 pgs.
Woody et al., "Integrating NIMH Research Domain Criteria (RDoC) into depression research", Current Opinion in Psychology, 2015, vol. 4, pp. 6-12, available online Jan. 12, 2015.
World Health Organization, "Mental Health Atlas 2011", Mental Health Atlas, 2011, 81 pgs.
World Health Organization, "Mental Health Atlas 2011, Resources for Mental Health in the Eastern Mediterranean Region", World Health Organization, 2011, 79 pgs.
Wu et al., "Default-mode network connectivity and white matter burden in late-life depression", NIH Public Access—Author Manuscript, 18 pgs. published in final form as Psychiatry Res.., Oct. 31, 2011, vol. 194, No. 1, pp. 39-46, doi: 10.1016/j.psychresns.2011.04.003.
Xia et al., "BrainNet viewer: A Network visualization Tool for Human Brain Connectomics", PLoS ONE, Jul. 4, 2013, vol. 8, Issue 7, e68910, pp. 1-15.
Yan, Chao-Gan, "DPABI: A toolbox for Data Processing & Analysis for Brain Imaging", The R-fMRI Network, submitted Aug. 4, 2014, Retrieved from: http://rfmri.org/dpabi, 26 pgs.
Yan et al., "DPABI: Data Processing & Analysis for (Resting-State) Brain Imaging", Neuroinform., 2016, published online Apr. 13, 2016, vol. 14, pp. 339-351.
Yang et al., "Adolescents With Major Depression Demonstrate Increased Amygdala Activation", Journal of the American Academy of Child & Adolescent Psychiatry, Jan. 2010, vol. 49, No. 1, pp. 42-51.
Yang et al., "Adolescents With Major Depression Demonstrate Increased Amygdala Activation", NIH Public Access—Author Manuscript, , 15 pgs., published in final form as: J. Am. Acad. Child Adolesc. Psychiatry, Jan. 201, vol. 49, No. 1, pp. 42-51.
Yarkoni et al., "Large-scale automated synthesis of human functional neuroimaging data", Nature Methods, Aug. 2011, vol. 8, No. 8, 10 pgs., published online Jun. 26, 2011.
Yeo et al., "The organization of the human cerebral cortex estimated by intrinsic functional connectivity", J. Neurophysiol., Jun. 8, 2011, vol. 106, pp. 1125-1165.
Young et al., "The Quality of Care for Depressive and Anxiety Disorders in the United States", Arch. Gen. Psychiatry, Jan. 2001, vol. 58, pp. 55-61.
Yuste, "From the neuron doctrine to neural networks", Nature Reviews | Neuroscience, Aug. 2015, vol. 16, pp. 487-497.
Zarate et al., "Pramipexole for Bipolar II Depression: A Placebo-Controlled Proof of Concept Study", Biol. Psychiatry, 2004, vol. 56, pp. 54-60.
Zbozinek et al., "Diagnostic Overlap of Generalized Anxiety Disorder and Major Depressive Disorder in a Primary Care Sample", NIH Public Access—Author Manuscript, 14 pgs., published in final form as Depress. Anxiety, Dec. 2012, vol. 29, No. 12, pp. 1065-1071, doi:10.1002/da.22026.
Zhang et al., "Disease and the brain's dark energy", Nature Reviews | Neurology, Jan. 2010, vol. 6, pp. 15-28.
Zhang et al., "Imbalanced spontaneous brain activity in orbitofrontal-insular circuits in individuals with cognitive vulnerability to depression", J. Affect Discord, 198, pp. 56-63, 2016.
Zhang et al., "The neural correlates of reward-related processing in major depressive disorder: A meta-analysis of functional magnetic resonance imaging studies", Journal of Affective Disorders, 2013, vol. 151, pp. 531-539, available online Jul. 12, 2013.
Zhao et al., "Brain grey matter abnormalities in medication-free patients with major depressive disorder: a metal-analysis", Psychological Medicine, 2014, vol. 44, pp. 2927-2937.
Zhong et al., "Amygdala hyperactivation and prefrontal hypoactivation in subjects with cognitive vulnerability to depression", Biological Psychology, 2011, available online Aug. 29, 2011, vol. 88, pp. 233-242.
Zhou, "Structure, function and regulation of P-glycoprotein and its clinical relevance in drug disposition", Xenobiotica, Jul.-Aug. 2008, vol. 38, Nos. 7-8, pp. 802-832.
Zhu et al., "Classification of gene microarrays by penalized logistic regression", Biostatistics, Jul. 2004, vol. 5, vol. 3, pp. 427-443.
Zhu et al., "Evidence of a Dissociation Pattern in Resting-State Default Mode Network Connectivity in First-Episode, Treatment-Naive Major Depression Patients", Biol. Psychiatry, Apr. 2012, vol. 71, No. 7, pp. 611-617.
Zimmerman et al., "Severity classification on the Hamilton depression rating scale", Journal of Affective Disorders, 2013, available online Jun. 4, 2013, vol. 150, pp. 384-388.
Zuo et al., "Reliable intrinsic connectivity networks: Test-retest evaluation using ICA and dual regression approach", NeuroImage, 2010, available online Nov. 5, 2009, vol. 49, pp. 2163-2177.
Iwabuchi, "fMRI Niyoru Nokinokeisoku: Kiso to Tenbo (Measurement of Brain Function by fMRI: basics and outlook)", Radiological Saitama, Jul. 20, 2016, vol. 64, No. 3, pp. 235-243.
Ashburner et al., "SPM8 Manual, chapters 1 and 33", Feb. 4, 2013, XP055921454.

(56) References Cited

OTHER PUBLICATIONS

Cesar et al., "Methods for Cleaning the Bold fMRI Signal", Neuroimage, Dec. 9, 2016, 154, pp. 128-149.
Patel et al., "A wavelet method for modeling and despiking motion artifacts from resting-state fMRI time series", NeuroImage, Jul. 1, 2014, vol. 95, pp. 287-304, XP055914474, ISSN: 1053-8119, DOI: 10.1016/j.neuroimage.2014.03.012.

* cited by examiner

Symptoms & Functioning

Sample output

Scoring explanation:

Scores range from 0 to 10, as shown below.
Lower scores indicate less severe symptoms.

Categories range from mild to severe, as shown below.

Mild  Moderate  Severe

Alcohol & Substance Use

| Measure | Category | Score | |
|---|---|---|---|
| Alcohol Use | Moderate | 5 | |
| Substance Use | | 1 | |

Clinical Symptoms

| Measure | Significance | Score | Score Range | Category |
|---|---|---|---|---|
| DASS Depression | | | 0 – 42 | Moderate |
| DASS Anxiety | | | 0 – 42 | Moderate |
| DASS Stress | | | 0 – 42 | Mild |
| MASQ General Distress | Reflects aversive emotional states such as fear, anger, and guilt that are associated with both anxiety and depression. | | 10 – 50 | Severe |
| MASQ Anhedonic Depression | Reflects the tiredness and sluggishness associated with depressive moods and loss of positive emotional status such as feeling active, excited, delighted, enthusiastic, and interested. | | 10 – 50 | |
| MASQ Anxious Arousal | Reflects symptoms of physiological hyperarousal such as trembling, shaking, dizziness, sweating, and heart racing. | | 10 – 50 | |
| COPE Self-Distraction | using activities to avoid thinking about stressors | | 0 – 8 | |
| COPE Active Coping | taking active steps to remove or avoid the stressor including initiating direct action and increasing efforts | | 0 – 8 | |
| COPE Denial | refusal to believe that the stressor exists | | 0 – 8 | |
| COPE Substance Use | use of alcohol and/or other drugs to manage negative feelings | | 0 – 8 | |
| COPE Use of Emotional Support | getting moral support, sympathy, or understanding | | 0 – 8 | |
| COPE Use of Instrumental Support | seeking advice, assistance, or information | | 0 – 8 | |
| COPE Behavioral Disengagement | decreasing effort to deal with the stressor and/or giving up goals with which stressor interferes | | 0 – 8 | |
| COPE Venting | focus on distress and express related feelings | | 0 – 8 | |

*FIG. 14*

🖩 Cognitive and Emotional Assessment Scores

Positive Valence (Emotion) Systems

Approach Motivation & Reward Valuation

| Task | Band | Measurement | Significance |
|---|---|---|---|
| Emotion Recognition – Happy (Accuracy) | | Identification accuracy for happy emotion. | Bias towards happy emotion. |
| Emotion Recognition – Happy (Speed) | | Identification speed for happy emotion. | Bias towards happy emotion. |

Negative Valence (Emotion) Systems

Acute Threat

| Task | Band | Measurement | Significance |
|---|---|---|---|
| Emotion Recognition – Anger (Accuracy) | | Identification accuracy for anger emotion. | Bias towards anger emotion. |
| Emotion Recognition – Anger (Speed) | | Identification speed for anger emotion. | Bias towards anger emotion. |

Potential Threat

| Task | Band | Measurement | Significance |
|---|---|---|---|
| Emotion Recognition – Fear (Accuracy) | | Identification accuracy for fear emotion. | Bias towards fear emotion. |
| Emotion Recognition – Fear (Speed) | | Identification speed for fear emotion. | Bias towards fear emotion. |

Loss

| Task | Band | Measurement | Significance |
|---|---|---|---|
| Emotion Recognition – Sad (Accuracy) | | Identification accuracy for sad emotion. | Bias towards sad emotion. |
| Emotion Recognition – Sad (Speed) | | Identification speed for sad emotion. | Bias towards sad emotion. |

*FIG. 15B*

 Description of Assessment Scores

The results of your cognitive and emotional assessments are listed below. Scores on each measure are divided into 7 bands. Scores improve from band 1 to band 7. Most people score closest to the middle, in band 4. The percentage indicates how many people score in that band. For example, 38% of people score in band 4. The scores reflect variation of performance in a normal population. This population is matched to you according to age, gender, and level of education

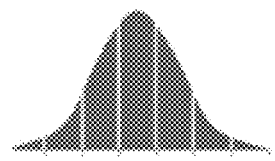 Band 1: significantly below average, 6.5% of individuals

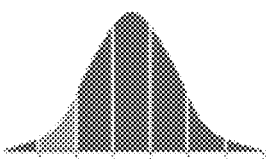 Band 2: below average, 9.5% of individuals

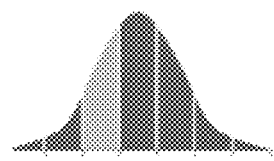 Band 3: low end of average, 15% of individuals

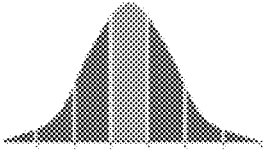 Band 4: average 38% of individuals

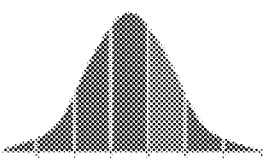 Band 5: high end of average, 15% of individuals

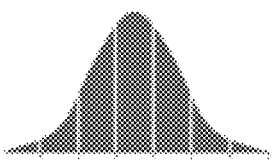 Band 6: above average, 9.5% of individuals

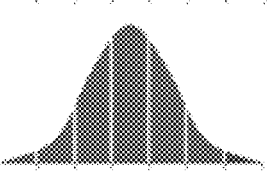 Band 7: significantly above average, 6.5% of individuals

*FIG. 15C*

SYSTEMS AND METHODS FOR DETECTING COMPLEX NETWORKS IN MRI IMAGE DATA

CROSS REFERENCE TO RELATED APPLICATIONS

The instant application claims priority to U.S. Non-Provisional patent application Ser. No. 16/368,774, filed Mar. 28, 2019, which claims priority to U.S. Non-Provisional patent application Ser. No. 15/997,631, filed Jun. 4, 2018 and issued as U.S. Pat. No. 10,285,658 on May 14, 2019, which claims priority to U.S. Non-Provisional patent application Ser. No. 15/820,338, filed Nov. 21, 2017 and issued as U.S. Pat. No. 10,034,645 on Jul. 31, 2018, which claims priority to U.S. Provisional Patent Application No. 62/485,196, filed Apr. 13, 2017, U.S. Provisional Patent Application No. 62/563,611, filed Sep. 26, 2017, U.S. Provisional Patent Application No. 62/568,676, filed Oct. 5, 2017, and U.S. Provisional Patent Application No. 62/589,452 filed Nov. 21, 2017, the disclosures of which are hereby incorporated by reference in their entirety.

FIELD OF THE INVENTION

The present invention relates generally to image processing, including automated image processing, and more specifically to the detection of objects and/or signals within images.

BACKGROUND

Object detection is a key component of many image processing and computer vision systems that enable a computer to locate and classify objects within an image or sequence of images. Classic examples of object detection include facial recognition, and object tracking. Processes for automated image tracking can also be useful for detecting objects or patterns that might not be immediately apparent to human viewers of the image. The ability for computers to perceive and comprehend visual data is key for enhancing the capabilities of computer systems to interact with, and provide feedback on, their environment.

SUMMARY OF THE INVENTION

Systems and methods for detecting complex networks in magnetic resonance imaging (MRI) image data in accordance with embodiments of the invention are illustrated. One embodiment includes an image processing system, including a processor, a display device connected to the processor, an image capture device connected to the processor, and a memory connected to the processor, the memory containing an image processing application, wherein the image processing application directs the processor to obtain a time-series sequence of image data from the image capture device, identify complex networks within the time-series sequence of image data, and provide the identified complex networks using the display device.

In another embodiment, the time-series sequence of image data includes data describing a set of images taken from a specific viewpoint over time.

In a further embodiment, images in the set of images are three dimensional images.

In still another embodiment, identifying complex networks within the time-series sequence of image data includes preprocessing the time-series sequence of image data, detecting structures within the time-series sequence of image data, and measuring connectivity between structures within the time-series sequence of image data.

In a still further embodiment, preprocessing the time-series sequence of image data includes realigning the time-series sequence of image data to a fixed orientation, unwarping the time-series sequence of image data, and despiking the time-series sequence of image data.

In yet another embodiment, a magnetic resonance imaging image processing system, including at least one processor, a memory connected to the at least one processor and containing an image processing application, a display in communication with the at least one processor, synchronization circuitry, a magnetic resonance imaging machine in communication with the synchronization circuitry and the at least one processor, wherein the magnetic resonance imaging machine is directed to obtain image data describing at least a patient's brain, and a stimulus device connected to the synchronization circuitry, wherein the stimulus device is configured to provide a stimulus to a patient, wherein the image processing application directs the processor to obtain the image data from the magnetic resonance imaging machine via a network, generate a time-series sequence of image data of the patient's brain, wherein the time-series sequence of image data is time-stamped with the times of stimuli provided by the stimulus device using the synchronization circuitry, and pre-process the time-series sequence of image data to identify brain regions, generate at least one neurological model, the at least one neurological model including a data structure describing at least one network within the time-series sequence of image data, and metrics specifying neurological activity observable within the time-series sequence of image data, assign a biotype to the patient based on the neurological model, and provide a graphical user interface containing the assigned biotype using the display.

In a yet further embodiment, preprocessing the time-series sequence of image data further includes realigning the time-series sequence of image data, unwarping the time-series sequence of image data, despiking the time-series sequence of image data; and, registering brain structures observable within the time-series sequence of image data and a brain atlas, wherein the brain atlas comprises a data structure stored in the memory and describes physical regions within a reference brain.

In another additional embodiment, despiking the time-series sequence of image data comprises measuring displacement between images in the time-series sequence of image data, and identifying time periods in the time-series sequence of image data where the displacement between images is greater than a frame displacement threshold.

In a further additional embodiment, the atlas is the Automated Anatomical Labeling atlas.

In another embodiment again, at least one of the at least one neurological model is a first level reactivity model, and the metrics specifying the neurological activity specify strength of neuronal activation across brain regions.

In a further embodiment again, the image processing application further directs the processor to generate a first level reactivity model, wherein generating the first level reactivity model includes extracting image data describing brain structures from image data describing non-brain structures in the time-series sequence of image data, removing global signals from the image data using a white noise mask, spatially smoothing the image data using a blurring kernel, and determining a degree of neuronal activation in response to stimuli delivered corresponding to the time-stamps in the time-series sequence of image data.

In still yet another embodiment, the blurring kernel is an 8 millimeter blurring kernel.

In a still yet further embodiment, the at least one of the at least one neurological model is a psychophysiological interaction model, and the metrics specifying the neurological activity specify degree of connectivity between brain regions.

In still another additional embodiment, the image processing application further directs the processor to generate a psychophysiological interaction model from the pre-processed time-series sequence of image data, wherein generating the psychophysiological interaction model includes performing slice time correction on the pre-processed time-series sequence of image data using a descending interleaved acquisition sequence, normalizing the pre-processed time-series sequence of image data to a coordinate system, spatially smoothing the pre-processed time-series sequence of image data using a blurring kernel, defining at least one volume of interest in the pre-processed time-series sequence of image data using a mask, extracting an eigenvariate from the at least one volume of interest, generating a volume of interest data structure including a deconvolved time course including the physiological component of the psychophysiological interaction model, a psychological variable describing a parametric contrast of task onsets from a contrast of interest, and data describing the interaction between the physiological and psychological variables.

In a still further additional embodiment, the at least one neurological model comprises a resting state model.

In still another embodiment again, generating the resting state model including concatenating preprocessed image data across stimuli, segmenting the concatenated image data by tissue types, generating at least one regressor matrix, generating residual images from the segmented preprocessed image data, and bandpass filtering the residual images.

In a still further embodiment again, the tissue types are at least white matter, grey matter, and cerebrospinal fluid.

In yet another additional embodiment, the at least one resting state model is a region of interest resting state model.

In a yet further additional embodiment, the at least one resting state model is a voxel wise resting state model.

In yet another embodiment again, generating the voxel wise resting state model further includes extracting a time-series sequence of image data corresponding to a particular set of stimuli from the segmented time-series sequence of image data, and applying regression against the extracted time-series sequence of image data for a particular set of stimuli against the segmented time-series sequence of image data for all voxels, indicating the overall resting state for each voxel.

In a yet further embodiment again, assigning a biotype includes obtaining a database of biotype classifications including image data annotated with reactivity and connectivity metrics associated with specific biotypes, matching metrics from the resting state model to the best fitting biotype classification.

In another additional embodiment again, the database of biotype classifications is generated using machine learning on a training data set.

In a further additional embodiment again, assigning a biotype includes generating an indicator of fit describing how closely the biotype matches the patient.

In still yet another additional embodiment, the assigned biotype is associated with at least one treatment, and the image processing application further directs the processor to recommend the at least one treatment to the user.

In another embodiment, the at least one treatment is an at least one drug, and a medical professional treats the patient by prescribing the at least one drug to the patient.

In a further embodiment, the image processing application further directs the processor to generate at least one efficacy metric based on the assigned biotype, wherein the at least one efficacy metric indicates the likelihood of success of treating the patient using the at least one drug.

In still another embodiment, the magnetic resonance imaging machine is connected to a first communications port capable of transmitting data over a network, the processor is connected to a second communications port capable of receiving data over the network; and the magnetic resonance imaging machine and the processor are connected via the network using the first communications port and the second communications port.

In a still further embodiment, the stimulus device provides a Go No-Go test battery and an emotional regulation test battery to the patient.

In yet another embodiment, the stimulus device is a visual display device.

In a yet further embodiment, a method for identifying complex networks in time-series sequence of image data, includes obtaining time-series sequence of image data from an image capture device, realigning the time-series sequence of image data to a fixed orientation using an image processing server system, unwarping the time-series sequence of image data using the image processing server system, despiking the time-series sequence of image data using the image processing server system, detecting objects within the time-series sequence of image data using the image processing server system, measuring connectivities between detected objects within the time-series sequence of image data using the image processing server system, matching the measured connectivities between detected objects to at least one complex network stored in a database of complex networks using the processor, and displaying the at least one matched complex network using a display device.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

FIG. 14 is an example of a survey rankings in accordance with an embodiment of the invention.

FIGS. 15A, 15B, and 15C are example assessment score reports in accordance with an embodiment on the invention.

DETAILED DESCRIPTION

Turning now to the drawings, systems and methods for detecting complex networks such as (but not limited to) neural circuit pathways in image data are discussed. Further, methods for complex network detection within a three-dimensional (3D) matrix of pixel data are disclosed. Object detection within images is a key aspect of machine vision, and allows computers to parse and understand image data. In a time ordered sequence of images (video), object detection over the video can be used to track activity, and enable detection of complex networks. Further, in a larger system where other components can trigger changes in the observed image, time synchronization circuitry can be used to match system activity to observed responses in a series of images.

Enhanced object detection capabilities have numerous applications, including, but not limited to, automation of tagging and classification of objects within images, as well as images themselves. The ability to classify objects allows a computer to perform additional processing, extract additional data, and/or utilize image information in other processing operations. In some cases, object detection can trigger image processing systems to produce warnings, reports, and/or other human-interpretable signals to automatically notify a user.

Network detection methods described below can be used with unconventional image capture systems, and can further be used to allow computer systems to process data in new and unconventional ways. In numerous embodiments, object detection and classification are used to generate a taxonomy of objects. Taxonomies of objects can then be used for rapid analysis of future images. In some embodiments, machine learning techniques can be applied to generate taxonomies.

One of ordinary skill in the art will appreciate that while specific implementations of methods and systems for performing complex network detection are described below, there are numerous embodiments in accordance with the spirit of the invention. While specific discussion will be directed to performing complex network detection within MRI image data, the systems and methods described below can be used to detect complex networks in a variety of types of image data and/or applications.

Image Processing Systems

Image processing systems can be used to acquire image data, process image data, and display processed data. In numerous embodiments, image processing systems are constructed of multiple computing systems. In a variety of embodiments, image processing systems are implemented on a single computing system. Image processing systems can process a wide variety of image data, however certain specific embodiments can be utilized for processing MRI image data.

Figure 1:
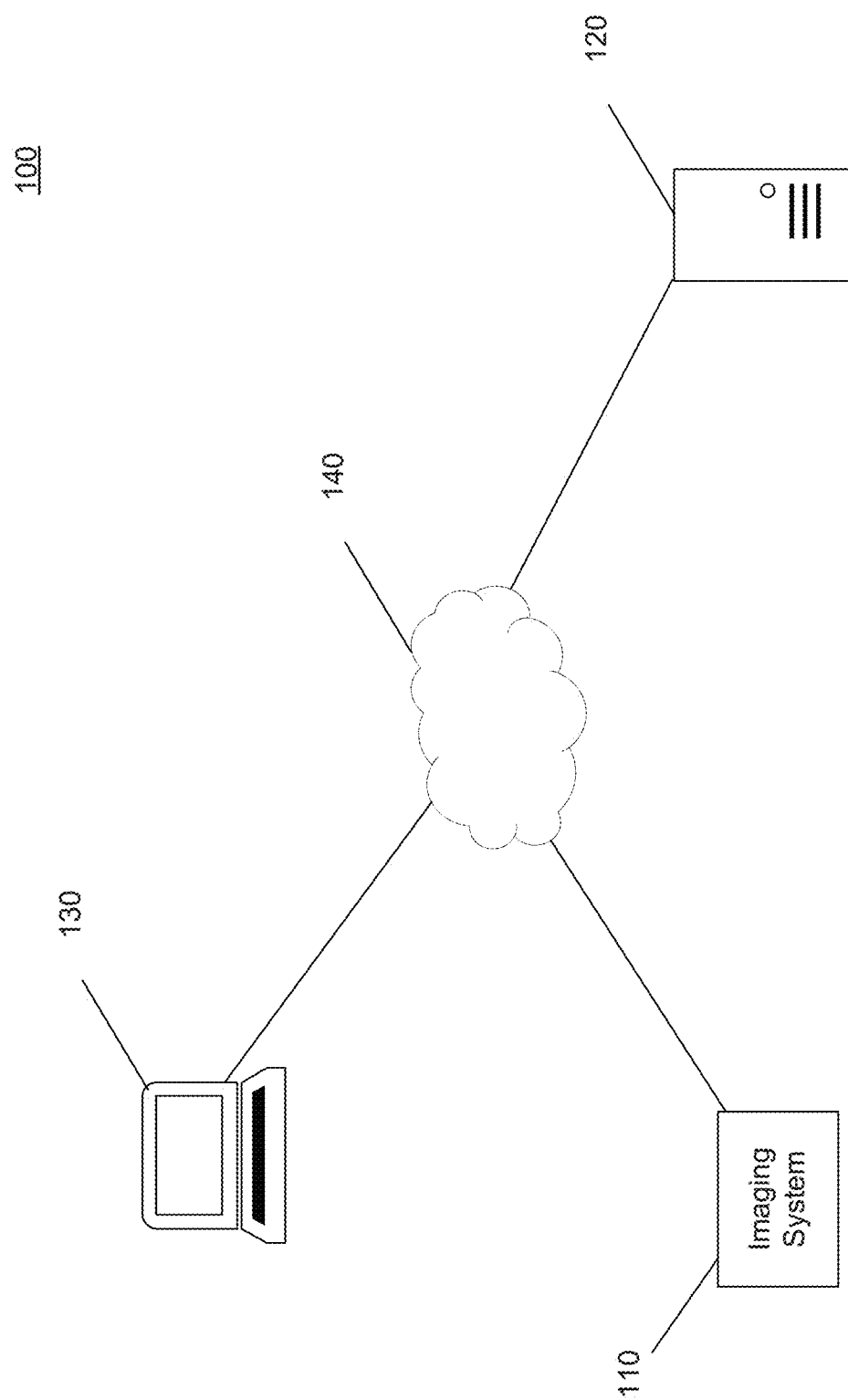
FIG. 1 is a system diagram illustrating connected components of an image processing system in accordance with an embodiment of the invention.

Turning now to FIG. 1, a system diagram of an image processing system in accordance with an embodiment of the invention is illustrated. Image processing system 100 has at least one image capture device 110. Image capture device 110 is connected to image processing server system 120 and image processing interface device 130 via network 140. In many embodiments, the image capture device is an MRI imaging device. However, the image capture device can be any device capable of capturing an image as appropriate to the requirements of a given application.

The image capture device can include various peripheral devices, including terminals, display devices, and other interface devices. The image processing server system can be implemented on a personal computer, a server computer system, or any other computing device as appropriate to the requirements of a given application. The image processing interface device can be a personal computer, a tablet computer, a smartphone, a monitor, and/or any other device as appropriate to the requirements of a given application.

Image processing server systems can include a processor, memory, and/or at least one storage system containing an image processing application that includes machine readable instructions that configures the computer to process image data in accordance with methods described below. In some embodiments, the image processing interface device and the image processing server system are on the same platform. The network can be, but is not limited to, the Internet, a local area network, a wireless local area network, wide area network, a software defined network, and/or any other type or combination of types of network as appropriate to the requirements of a given application.

Devices described above can communicate via the network via communications ports. In many embodiments, data is transferred between one or more devices via the network. In a variety of embodiments, data transfer between one or more devices is achieved using physical media transfer, such as a flash drive, compact discs, or any other physical storage media as appropriate to the requirements of a given application.

Once images are obtained by the image capture device, image data describing the captured image can be sent via the network to the image processing server system for analysis. In some embodiments, image data is also sent to the image processing interface device. In numerous embodiments, the image processing server system processes received image data and outputs results to the image processing interface device. In a variety of embodiments, some processing is done by the image processing interface device.

Processed data and/or any other output of the system can be provided to the user by a user interface device. In many embodiments, user interface devices provide graphical user interfaces which enable a user to access data. In many embodiments, the user interface device is connected to the network.

In many embodiments, one or more of the devices on the network incorporate, or have access to, synchronization circuitry. Synchronization circuitry can be used to synchronize image capture with provided stimuli. In numerous embodiments, the image processing interface device is configured to provide stimulus using a stimulus device. In a variety of embodiments, stimulus devices are controlled by the image processing server system, and/or the image capture device. A stimulus device can be a visual display device, such as, but not limited to, a monitor, a virtual reality headset, a projector, and/or any other visual display device as appropriate to the requirements of a given application. A stimulus device can be an audio display device, such as a speaker. Stimulus devices can provide visual stimuli, audio stimuli, tactile stimuli, and/or any other stimuli as appropriate to the requirements of a given application.

While specific network configurations have been described above, one of ordinary skill in the art can appreciate that any configuration or devices could be used as appropriate to the requirements of specific applications. Methods for image processing using image processing systems are described below.

Performing Complex Network Detection in MRI Image Data Using Image Processing Systems MRI scans of a patient's head yield high quality image data of the patient's brain in a non-invasive manner. While there are many different types of MRI scanning techniques, two categories of MRI scans are the functional MRI (fMRI) and the structural MRI (sMRI). sMRI scans generally acquire 3D image data of a patient's brain, defining the structural anatomy. In many embodiments, sMRI scanning can include different imaging techniques such as, but not limited to, diffusion tensor imaging, or any other specialized scanning technique. fMRI scans are a type of MRI scan that yields time-series sequence of image data describing neuronal activation within the patient's brain. In many embodiments neuronal activation patterns can indicate the degree of connectivity between different regions of the patient's brain. In many embodiments, MRI data is preprocessed to remove artifacts. In a variety of embodiments, neuronal activation patterns can indicate the degree of reactivity to particular stimuli in the patient's brain. Image processing systems can be used to process fMRI data to extract data regarding connectivity and reactivity. Based on connectivity and/or reactivity data, one or more biotypes can be assigned to the patient. Biotypes can be associated with one or more drugs and/or therapies that can be more effective in treating at least one negative symptom that the patient suffers from. In many embodiments, machine learning can be utilized to associate biotypes with specific connectivities and/or reactivities. In a variety of embodiments, support vector machines are used to associate biotypes with specific connectivities and/or reactivities. Systems and methods for associating specific connectivities and/or reactivities with biotypes are described below.

Figure 2:
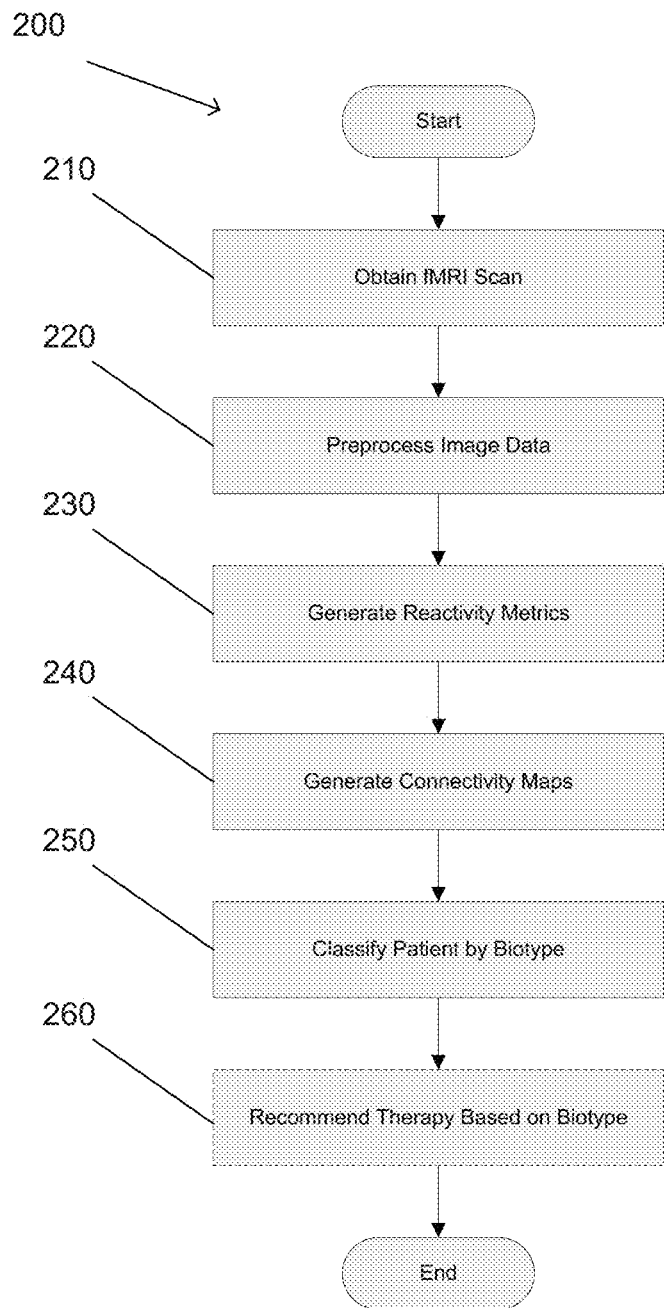
FIG. 2 is a flow chart illustrating a method for detecting and classifying objects in images in accordance with an embodiment of the invention.

Turning now to FIG. 2, a process for performing complex network detection in accordance with an embodiment of the invention is shown. Process 200 includes (210) obtaining fMRI scan data, and preprocessing (220) image data. Reactivity metrics are generated (230), connectivity maps are generated (240), and the observed connectivity forms the basis of a complex network classification enabling assignment of a biotype (250) to the observed neural circuit pathways. In some embodiments, a therapy can be recommended (260) based on the assigned biotype. In many embodiments, process 200 is performed by image processing server systems. However, in some embodiments, part or all of process 200 can be performed by image capture devices and/or image processing interface devices. Methods for obtaining image data are described below.

While various processes for identifying and/or classifying complex networks, such as neural circuit pathways, are described above with reference to FIG. 2, any of a variety of processes can be utilized to identify and classify complex networks using image data as appropriate to the requirements of specific applications in accordance with numerous embodiments of the invention. A number of processes that can be utilized to identify and classify complex networks in accordance with certain embodiments of the invention are discussed below.

Obtaining Image Data

Image data can be obtained using specialized image capture devices, such as MRI machines, that output MRI scan data. In many embodiments, patients are placed inside of MRI machines. Stimuli can be provided via a stimulus device to the patient and their psychophysical responses can be recorded using at least the MRI machine. These responses can be recorded over time using fMRI techniques to generate time-series data. In many embodiments, a resting state fMRI is generated. In a number of embodiments MRI data taken during performance of tasks can be utilized to filter MRI data obtained during periods in which tasks are not being performed to provide a more accurate model of resting state neural circuit activation.

Figure 3:
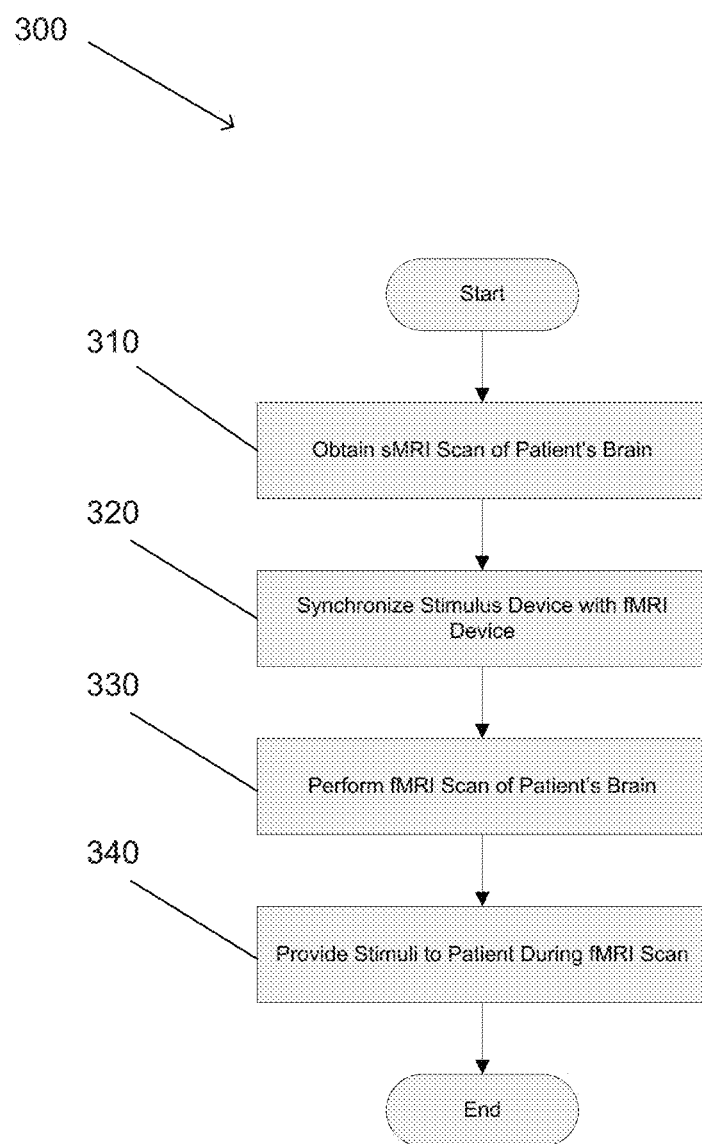
FIG. 3 is a flow chart illustrating a method for performing a test battery in accordance with an embodiment of the invention.

Turning now to FIG. 3, a method for obtaining image data in accordance with an embodiment of the invention is illustrated. Process 300 includes obtaining (310) a sMRI scan of a patient's brain. Process 300 also includes synchronizing (320) at least one stimulus device with the fMRI device, performing (330) and fMRI scan of the patient's brain while providing (340) stimuli to the patient. In numerous embodiments, the sMRI scan is image data captured by an MRI machine. In a variety of embodiments, the same MRI machine is used to perform the sMRI scan and the fMRI scan. MRI machines can have ancillary components, including connected computing devices that collect and store data from the scanning components of the MRI. In many embodiments, performing an fMRI scan generates a time-series of image data depicting neural activity within the brain of the patient. The time-series sequence of image data can be sets of sets of images, which together show the 3-D structure of the brain. In some embodiments, each image is a 3-D image representing a portion of the brain. A sub-portion of an image is called a voxel. In many embodiments, a single time-series sequence of image data set is generated during the course of an fMRI session. However, in numerous embodiments, several time-series of image data are acquired. In a variety of embodiments, at least one set of time-series of image data is acquired per stimulus battery (task).

Stimuli can be applied to the patient during scanning to measure the effect of the stimuli on neuron activation within the brain. In many embodiments, stimuli are images displayed to the patient. Synchronizing stimuli with the images in the time-series associates the response with the stimulus that caused it. Synchronization of stimulus devices with MRI scanners can be achieved using synchronization circuitry. In numerous embodiments, synchronization is mediated by a software application designed to associate continuous time series image data with a continuous time series stimulus regime. In this way, the image data output by the MRI machine can be processed relative to specific stimuli. In a variety of embodiments, time-series data is generated that is time stamped, where the time stamps are synchronized with time stamps present within image date captured by the MRI machine. In numerous embodiments, the delay between stimulus and the resultant image data time stamp is on the order of 100 milliseconds. In order to correct for delay, stimulus images can be jittered by +/−200 milliseconds. However, any jitter amount can be applied as appropriate to the requirements of given applications. That is, effects of stimuli detected within the image can be correlated to the specific stimulus that caused the response.

While various stimuli and measurement techniques that can be utilized in the detection of complex networks such as, but not limited to, neural circuit pathways are described above with reference to FIG. 3, any of a variety of stimuli and measurement techniques can be utilized as appropriate to the requirements of a given application in accordance with many embodiments of the invention. Additionally, while systems and methods utilizing MRI machines in accordance with various embodiments of the invention are described above, similar systems and methods can be applied to image data obtained from other image capture devices, such as, but not limited to, computed tomography scanners, positron emission tomography scanners, or any other brain imaging device as appropriate to the requirements of a given application. Methods and types of stimuli are described below.

fMRI Stimuli

Figure 4:
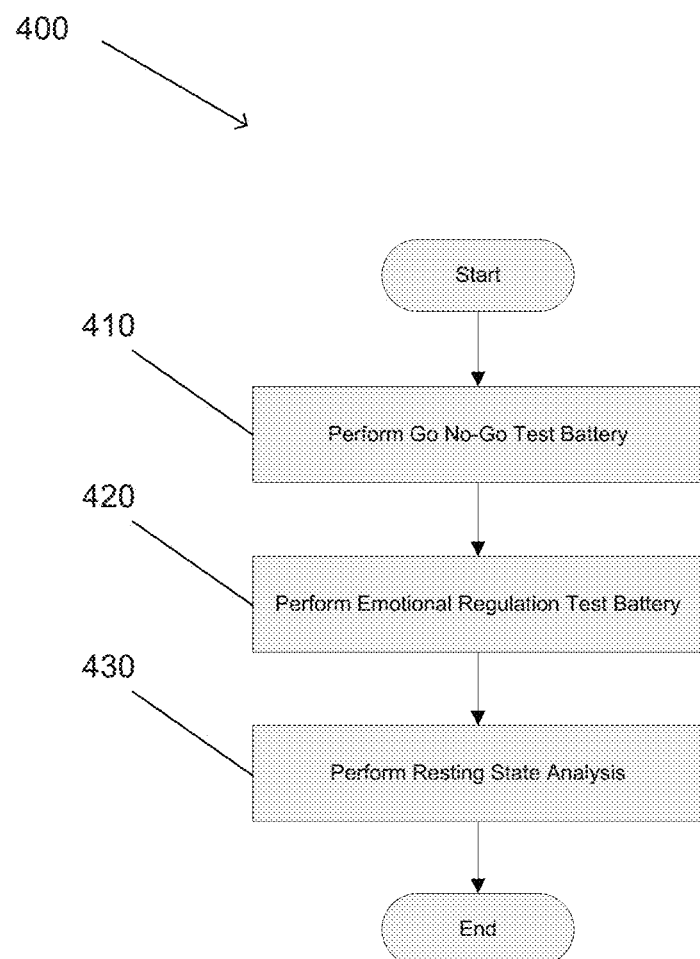
FIG. 4 is a flow chart illustrating a method for providing stimuli in accordance with an embodiment of the invention.

Psychophysical responses are dependent upon stimuli provided. Particular stimuli, and the patient's responses can be used to generate diagnostic and treatment data. In many embodiments, diagnostic and treatment data describes a patient's biotype, and/or appropriate treatments tailored to the patient's specific biotype. In many embodiments, correlating particular responses to specific stimuli can be used to generate data. In some embodiments, the particular sequence of stimuli is kept consistent across tests for the same patient. In a variety of embodiments, the particular sequence of stimuli is kept consistent across many patients. The sequence of stimuli can be chosen in such a way as to reduce the likelihood of artifacts Turning now to FIG. 4, a method for providing stimulus to a patient in accordance with an embodiment of the invention is illustrated. The method 400 includes performing (410) a Go No-Go test battery, and performing (420) an emotional regulation test battery. In many embodiments, motional test batteries include at least one face test battery. Face test batteries can include, but are not limited to, conscious faces test batteries, nonconscious faces test batteries, or any other emotional regulation task as appropriate to the requirements of a given application. Method 400 further includes performing (430) a resting state analysis.

In many embodiments, Go No-Go test batteries involve providing a series of representations to a patient as stimuli, wherein some representations indicate a "Go" state, and some representations indicate a "No-Go" state. For example, a Go state can be a word, such as, but not limited to, "Press," and/or a color indicator such as, but not limited to, green. A No-Go state can be a word, and/or a color indicator such as, but not limited to, red. In many embodiments, representations are displayed at predefined intervals. In some embodiments, indicators are displayed for 500 milliseconds, with a 750 millisecond stimulus interval. However, any display and/or stimulus interval duration can be used in accordance with the requirements of a given application.

Faces test batteries can include providing representations of faces representing emotional states. Representations can be placed in a specific, pseudorandom, or random ordering. Conscious face test batteries can display the representations at intervals allowing for conscious recognition by the patient, such as, but not limited to, 500 millisecond display times with 750 millisecond interstimulus delay. Nonconscious face test batteries can be designed in a similar way to conscious face test batteries with backwards masking. An emotional state representation can be displayed for 10 milliseconds, followed by a neural (non-emotion state) representation for 490 milliseconds. However, any time intervals can be used as appropriate to the requirements of given applications. For example, any set of intervals that allows for nonconscious recognition of emotional state representations can be used.

Resting state scans can be acquired by presenting the patient with a black screen, and/or any other neutral, non-task stimuli, and performing an fMRI scan while the patient remains awake. While several tests have been described above with respect to FIG. 4, one of ordinary skill in the art would recognize that any number of tasks and tests can be used in accordance with the requirements of various applications.

One of ordinary skill in the art will recognize that the tests could be performed in any order, and that no specific ordering is required. Further, not all tests need to be performed. In some embodiments, only a resting state analysis is utilized. Methods for preprocessing acquired image data are described below.

Preprocessing Image Data

Preprocessing image data can be performed by image processing systems to remove artifacts, and prepare the image data for subsequent analysis and processing steps. In numerous embodiments, preprocessing can be used to standardize image data to known reference images. For example, in several embodiments, MRI image data can be preprocessed to yield time-series sequence of image data in which brain structures and/or regions within the preprocessed time-series can be identified by the image processing system. In a variety of embodiments, a machine learning system is utilized to identify brain structures and/or regions using a training dataset of brain images. In a variety of embodiments, the image processing system uses a reference atlas to identify structures.

Figure 5:
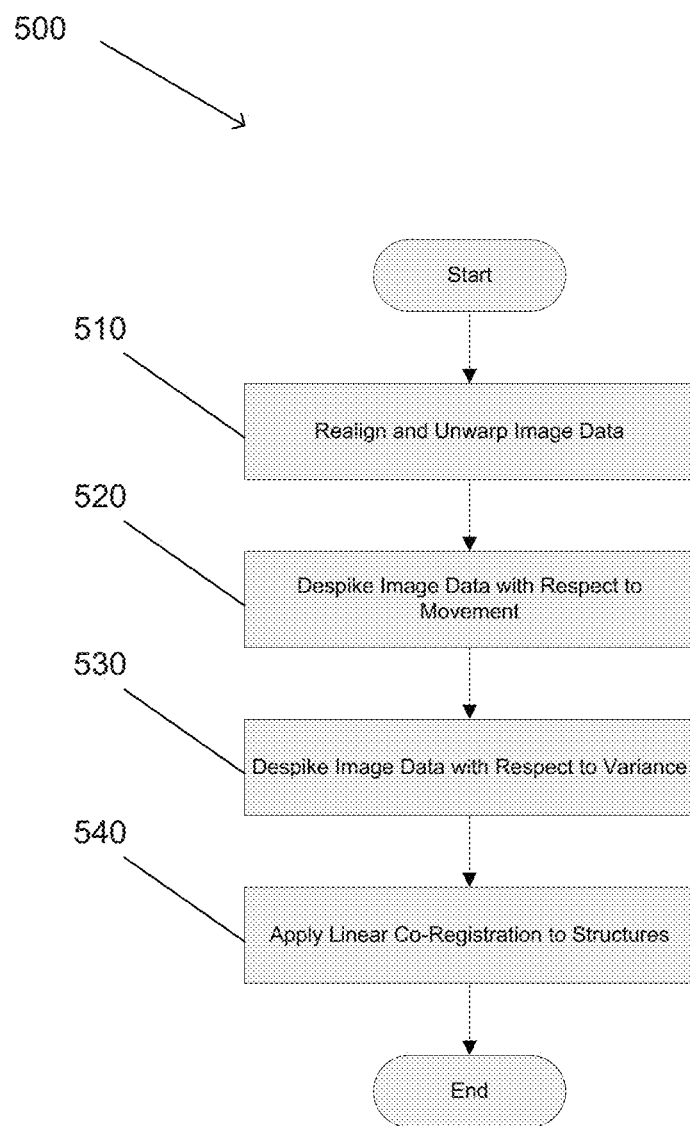
FIG. 5 is a flow chart illustrating a method for preprocessing image data in accordance with an embodiment of the invention.

Turning now to FIG. 5, a method for preprocessing image data is illustrated. Process 500 includes realigning and unwarping (510) image data. Image data can be despiked (520) with respect to movement and despiked (530) with respect to variance and/or any source of noise artifacts as appropriate to the requirements of a given application. In many embodiments, spikes with respect to variance are the result of extreme responses, such as, but not limited to, periods of very high activity followed by periods of very low activity. Further, process 500 includes applying (540) linear co-registration to identified structures in the image data. Realigning and unwarping image data can be used to remove movement artifacts from a fMRI scan time-series of images. Methods for realigning and unwarping image data that can be used in accordance with several embodiments of the invention can be found in the Statistical Parametric Mapping (SPM) library by the Wellcome Trust Centre for Neuroimaging of University College London, London, England. The manual of SPM version 8 (SPM8) can be found at http://www.fil.ion.ucl.ac.uk/spm/doc/spm8_manual.pdf. However, other processes, including other versions of SPM, such as SPM12 can be used as appropriate to the requirements of a given application.

fMRI image data can be despiked with respect to movement and variance. In many embodiments, the repetition time (TR) can be used to map when spikes occurred. In a variety of embodiments, a frame displacement (FD) threshold is established and used to detect spikes. In some embodiments, an FD threshold of 0.3 mm is used. However, any of a variety of FD thresholds can be used in accordance with various applications of given embodiments of the invention. In numerous embodiments, default variance cut-offs, and spike regressors are generated. Variance cut-offs and/or spike regressors can be utilized when performing later regression steps. In many embodiments, the cut-offs are used to ensure quality data for regression models.

Further, quality control (QC) images and metrics can be generated. For example, scaled and unscaled mean variance images across the time series can be generated. In some embodiments, max variance images across the time series can be generated. In a variety of embodiments, temporal signal to noise ratios can be measured across the time-series. While specific QC images and metrics are described above, any number of different QC metrics could be used in accordance with given applications.

Linear co-registration can be performed using the FSL software library of by the Oxford Centre for Functional MRI of the Brain of the University of Oxford (FMRIB), Oxford, England, including the FMRIB's Linear Image Registration Tool (FLIRT). An online manual for the FSL software package, including FLIRT, and a variety of other programs discussed herein, can be found at (https://fsl.fmrib.ox.ac.uk/fsl/fslwiki/). While a specific method for preprocessing image data is described above, any number of steps could be incorporated for preprocessing image data in accordance with the requirements of a given application. Preprocessed data can be used in a variety of ways, including, but not limited to, generating reactivity models and connectivity models. Methods of generating reactivity models are discussed below.

Generating Reactivity Models

Reactivity models can be generated from preprocessed image data. Reactivity models indicate which regions and/or structures of the brain become active and/or reactive in response to a stimulus. In numerous embodiments, reactivity processing is performed region by region in the brain. Reactivity processing can involve generating first level reactivity models. First level reactivity models can include data describing the reactivity of particular regions of interest (ROI) in the brain. ROIs can be individual structures, and/or groups of structures. In many embodiments, reactivity models describe the degree of activity within various regions of the brain. In several embodiments, the degree of activity in a region can be classified as hypoactive, typical, or hyperactive. The activity of particular regions can be utilized to determine effective treatments. Treatments can affect the activity of particular brain regions. In a variety of embodiments, additional processing steps are utilized to prepare the preprocessed image data for analysis.

Figure 6:
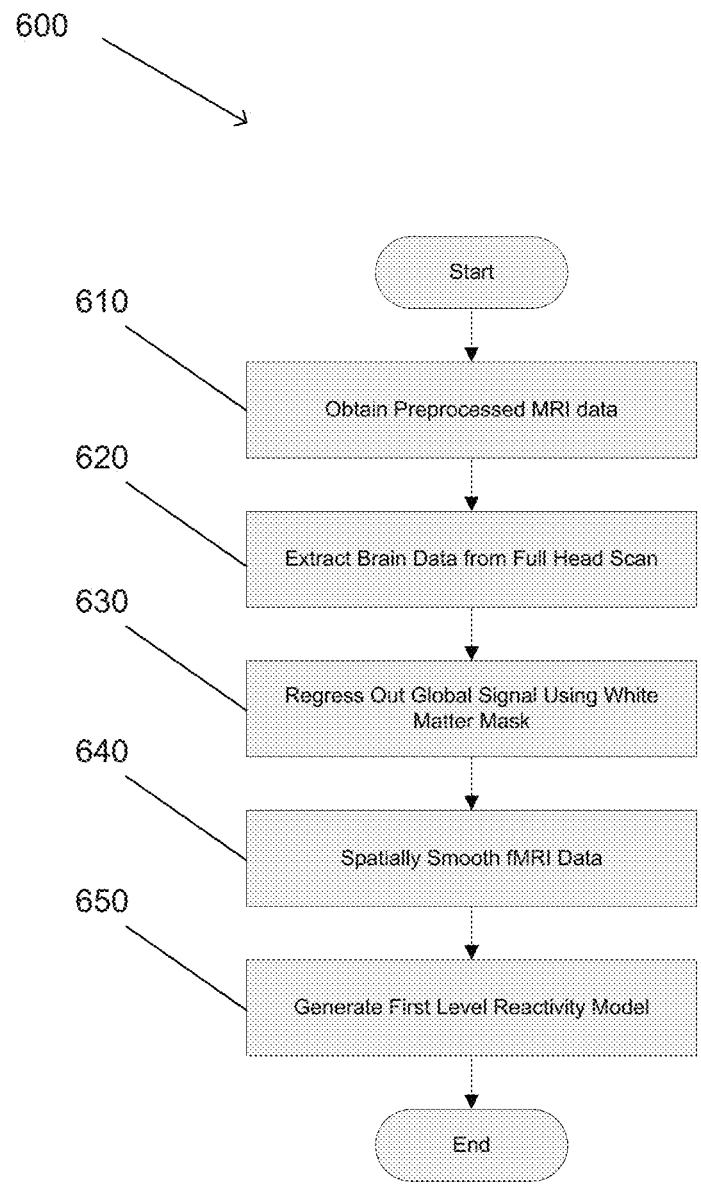
FIG. 6 is a flow chart illustrating a high level overview of a method for generating reactivity models in accordance with an embodiment of the invention.

Turning now to FIG. 6, a method for generating reactivity models in accordance with an embodiment of the invention is illustrated. Process 600 includes obtaining (610) preprocessed image data. Brain data is extracted (620) and global signals can be regressed (620) out using a white matter mask. The image data can be spatially smoothed (630) and first level reactivity models can be generated (640).

In many embodiments, preprocessed image data is obtained from the memory of an image processing server system. However, preprocessed image data can be obtained from a variety of storage systems, such as, but not limited to, flash drives, random access memory, hard disk drives, solid state drives, SD cards, or any other storage medium as appropriate to the requirements of a given application. Brain data can be extracted from preprocessed image data in such a way that non-brain tissue can be removed from the image. In a variety of embodiments, the Brain Extraction Tool (BET) of the FSL software package can be used to perform brain extraction. However, any of a variety of structure detection methods can be used to extract non-brain material from images, including, but not limited to, edge detection, greyscale matching, gradient matching, corner detection, ridge detection, Hough transforms, structure tensors, feature description algorithms, and/or any other feature detection algorithm as appropriate to the requirements of given applications.

Global signals can be removed via regression using a white noise mask. In a variety of embodiments, the white noise mask is warped into the native space of the image data being processed. The image data can be smoothed by applying a blurring kernel across each image in the time-series. In a variety of embodiments, a blurring kernel of 8 millimeters is utilized. However, any number of different kernel sizes can be used as appropriate to the requirements of a given application. In a variety of embodiments, nuisance regressors are applied to remove additional spikes. First level reactivity models can be generated from the image data. In many embodiments, first level reactivity models describe neuron activation, including varying degrees of activation such as hypo, typical, and hyper activation in response to specific stimuli.

While a specific method of generating reactivity models is illustrated above, one of ordinary skill in the art would appreciate that the recited processes could be performed in different orders, or some processes may be added or omitted as appropriate to the requirements of a given application. In addition to generating reactivity models, preprocessed data can be used to generate connectivity models. Methods for generating connectivity models are described below.

Generating Connectivity Models

Connectivity models can describe the connections between various regions of the brain. In some cases, neuronal connections between regions are underdeveloped, typically developed, or overdeveloped. In a variety of embodiments, connectivity models and reactivity models describe complex networks. However, complex networks can contain information from just reactivity models, or just connectivity models in accordance with the requirements of a given application. In several embodiments, connectivity models are generated from preprocessed image data. In many embodiments, pre-processed image data can be passed through additional connectivity preprocessing steps to enable creation of accurate connectivity models from captured MRI data. Various connectivity models and metrics can describe how signals from different regions and/or structures of the brain of the patient are transmitted.

In many embodiments, the organization of the connections between various brain structures and/or regions can be used to indicate responsiveness to various psychoactive chemicals. Connectivity models and metrics can include psychophysical interaction (PPI) models, ROI resting state models, and voxel wise resting state models. PPI models can describe connectivity between a ROI and other brain regions, thereby indicating the brain regions where the activity depends on the psychological context and the physiological state of the ROI. Resting state models are used to estimate the resting state of a particular ROI, or a region defined by a voxel or set of voxels. Methods for performing connectivity analysis are described below.

Figure 7:
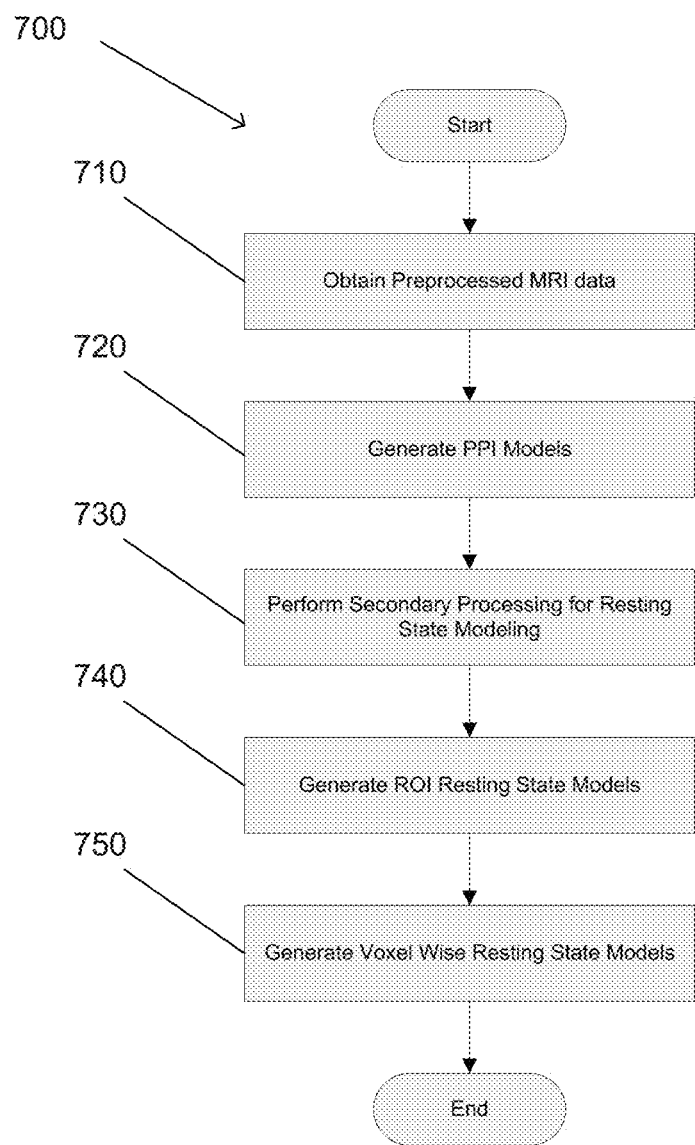
FIG. 7 is a flow chart illustrating a high level overview of a method for generating connectivity models in accordance with an embodiment of the invention.

Turning now to FIG. 7, a method for performing connectivity analysis in accordance with an embodiment of the invention is illustrated. Process 700 includes obtaining preprocessed image data. Preprocessed image data can be obtained in a similar manner as describe above with respect to reactivity models. Process 700 further includes generating (720) PPI models, and performing (730) secondary processing for resting state modeling. ROI resting state models can be generated (740) and voxel wise resting state models can be generated (750). Methods for performing additional connectivity preprocessing steps are described below.

Connectivity Preprocessing

Figure 8:
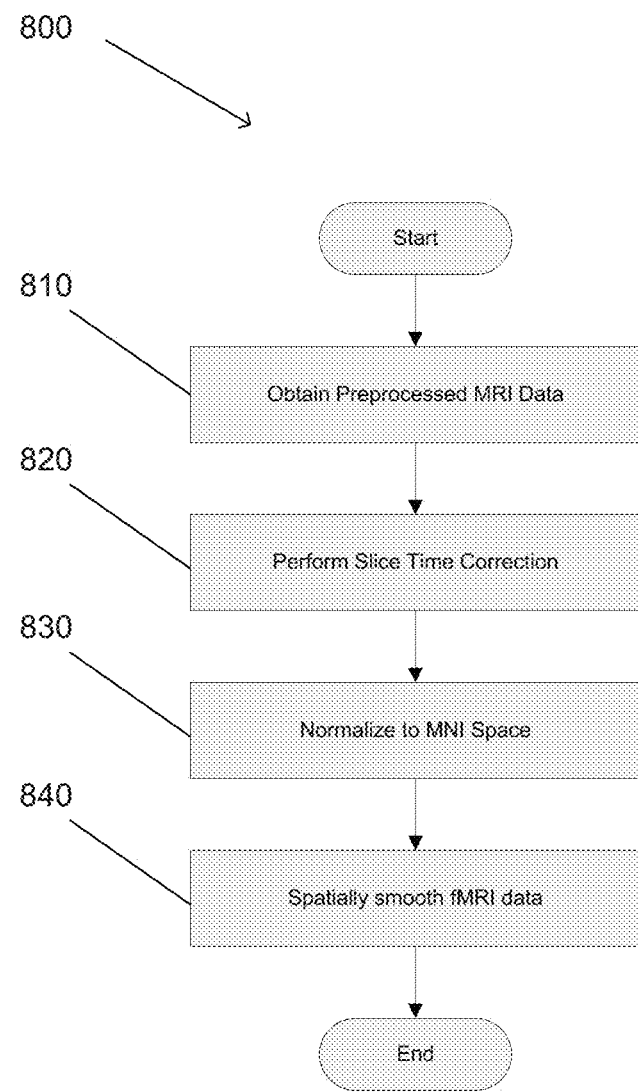
FIG. 8 is a flow chart illustrating a method for preprocessing data for connectivity analysis in accordance with an embodiment of the invention.

Preprocessed image data can be passed through additional connectivity preprocessing steps to enable accurate measurements of time-series data. Connectivity preprocessing can include mapping the image data to a coordinate system in order to define regions of the brain. Turning now to FIG. 8, a process for performing connectivity preprocessing in accordance with an embodiment of the invention is described below.

Process 800 includes obtaining (810) preprocessed image data. Slice time correction can be performed (820) and image data can be normalized (830) to a coordinate system. The image data can further be smoothed (830).

In many embodiments, slice time correction can be achieved using a given number of slices with a repeat time (TR) of 2.5 seconds and a descending interleaved acquisition sequence. In some embodiments, the given number of slices is 40, however any number of slices could be used in accordance with the requirements of a given application. Slice time correction can help correct for error introduced by non-simultaneous slice recording during a scanning iteration. Further, when the image data is normalized to a coordinate system, a variety of coordinate systems can be used. In many embodiments, the Montreal Neurological Institute (MNI) coordinate system is used. However, numerous other coordinate systems could be used, including, but not limited to, the Talairach coordinate system. Additionally, spatial smoothing can be performed similarly to the methods described above with respect to relativity analysis. In a variety of embodiments, once connectivity preprocessing has occurred, connectivity models can be generated. Furthermore, first level general linear models (GLM) can be initialized. Methods for generating PPI models are described below.

Generating PPI Models

PPI models can be used to determine which neuronal activations in a brain at a given time are dependent on a given stimulus. PPI analysis gives insight into the functionality of an individual's brain. In many embodiments, the FEAT program of the FSL software package can be used to generate PPI models. However, any number of programs and/or packages can be used to generate PPI models as appropriate to the requirements of a given application.

Figure 9:
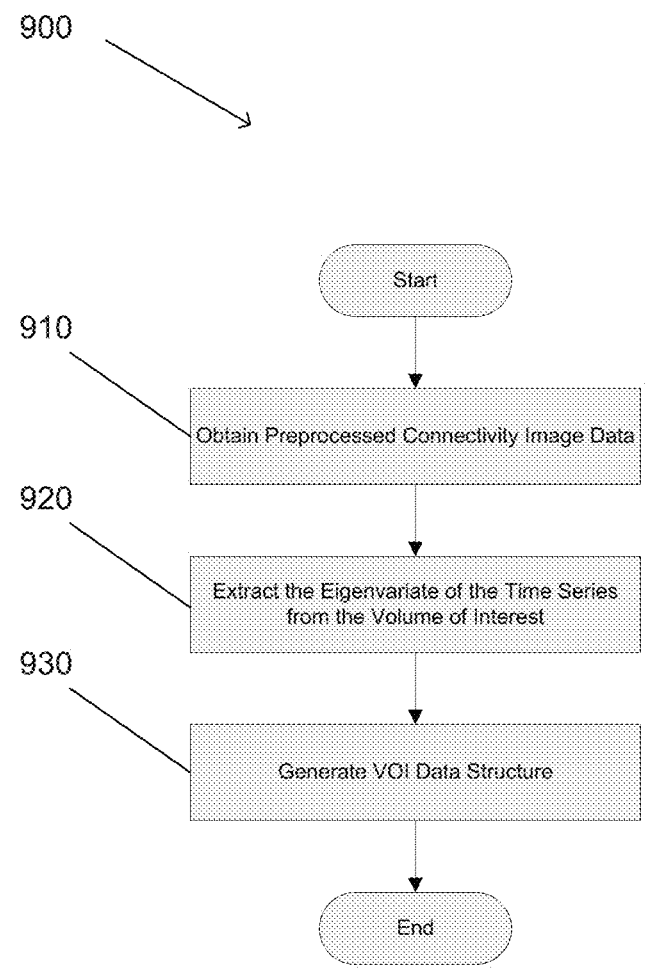
FIG. 9 is a flow chart illustrating a method for generating PPI models in accordance with an embodiment of the invention.

Turning now to FIG. 9, a process for generating PPI models in accordance with an embodiment of the invention is illustrated. Process 9 includes obtaining (910) preprocessed connectivity image data. The eigenvariate of the time series is extracted (920) from the volume of interest (VOI), and a VOI data structure is generated (930).

In many embodiments, the VOI is defined by a mask. In a variety of embodiments, the VOI is defined by a masked that is anatomically-derived. Anatomically-derived masks can be spheres that mask out specific regions of the brain. However, any shape of mask, including complex three-dimensional structures can be used as appropriate to the requirements of a given application. In numerous embodiments, the mask used to define the VOI masks out regions that are not in a ROI. The eigenvariate of the time series from the VOI can be extracted using the SPM8 library. In some embodiments, extracting the eigenvariate further includes obtaining a specific task. In a variety of embodiments, extracting the eigenvariate includes obtaining a specific mask. In many embodiments, extracting the eigenvariate includes obtaining a contrast number from a first level GLM. Generating a VOI data structure can include a deconvolved time course containing only the physiological component of the PPI, the psychological variable describing the parametric contrast of task onsets from the contrast of interest, and the interaction between the physiological and psychological variables. This data structure can function as the PPI model. In numerous embodiments, nuisance regressors are used from the first level GLM. While a specific method of generating a PPI data structure has been described above, any number of additional variables can be used as appropriate to the requirements of a given application. Connectivity preprocessed image data can be further utilized to generate resting state models. Methods for generating resting state models are described below.

Generating Resting Models

Resting state models can be used to determine the default resting state of the brain. The default resting state can give insight into the normal level of reactivity for a particular region of the brain for the individual in question. Hypo, typical, or hyper activation between different regions can give valuable insight into both brain related disorders, and potential treatment methods.

In many embodiments, resting state models are acquired by performing fMRI scans on a patient who is instructed to perform no tasks, and is not provided any stimuli. In a variety of embodiments, resting state models can be generated using fMRI data acquired during a test battery. Residual images can be generated using the test battery fMRI data, which can be used to generate a model of the patient's resting state. Image data acquired during various tasks can be useful in helping isolate neural activation observed during intervals in which tasks are not being performed, but that is task related. In this way, neural circuit pathways activated during resting state can be better separated from activations that are artifacts arising from the challenges of maintaining patients in a true resting state during imaging. While removal of such artifacts typically results in more informative neural circuit pathway classification, neural circuit pathway classification can be performed using processes without, or with minimal artifact removal.

Figure 10:
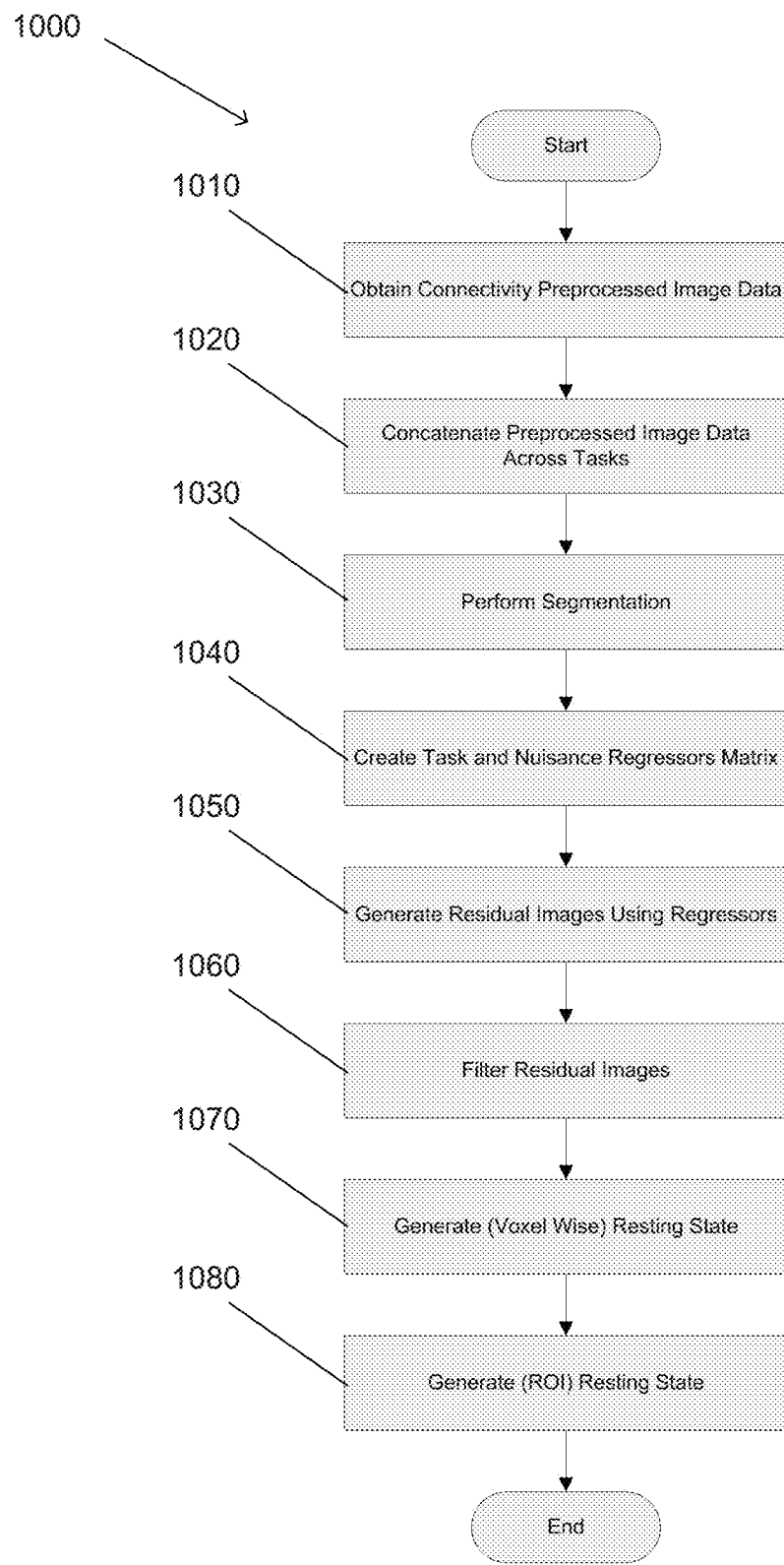
FIG. 10 is a flow chart illustrating a method for modeling resting state in accordance with an embodiment of the invention.

Turning now to FIG. 10, a process for generating resting state models in accordance with an embodiment of the invention is illustrated. Process 1000 includes obtaining (1010) connectivity preprocessed image data, and concatenating (1020) preprocessed image data across tasks. Segmentation is performed (1030), and a task and nuisance regressors matrix is generated (1040). Residual images are generated (1050) using the regressors matrix, and the residual images are filtered (1060). Voxel wise resting state models are generated (1070) and ROI resting state models are generated (1080).

In many embodiments, time-series data is generated for each task provided to the patient. Time-series data can be concatenated to form a single time-series image sequence. In many embodiments, concatenation is performed by appending successive time-series to a chosen first time series. Segmentation can be performed on the time-series in order to segment the structural images into white matter, grey matter, and cerebrospinal fluid (CSF) probability maps. In many embodiments, segmentation is performed using the FAST program from the FSL library. In order to optimize segmentation, white matter and CSF masks can be eroded from the edges inward for several iterations in order to ensure that the masks are capturing correct tissue matter. In a variety of embodiments, erosion can be performed using the SPM library. In many embodiments, three iterations are applied, however any number of iterations can be applied in accordance with the requirements of a given application. The segmented time-series sequence of image data can be warped into coordinate space defined by the Montreal Neurological Institute (MNI space), and additional masking can be applied to fine tune segmentation. For example, a mask can be used to remove additional grey matter from the white matter segment as a result of the erosion. In many embodiments, the mask is an atlas from the AAL Single Subject Atlas set provided by the Montreal Neurological Institute. Once segmentation has been performed, the mean time-series for each segment can be stored and/or provided.

A regressor matrix can be generated for use with the segmented time-series. In many embodiments, the regressor matrix includes some or all of: task regressor information, including a constant to indicate overall task effects; spike regressor information; realignment parameters, and their temporal derivatives and their squares; and white matter and CSF time-series across all tasks. Residual images can be generated by running regression to move the variance associated with a particular task, movement, and white matter/CSF noise using the generated regressor matrix. Residual images can then be filtered by bandpass filtering. In many embodiments, a high frequency cutoff of 0.009 Hz and a low frequency cutoff of 0.08 Hz is used. However, different cut-offs can be used as appropriate to the requirements of a given application.

Resting state models can be generated using the filtered images. Voxel wise resting state models can be generated by extracting the time-series for a specific task, and regressing against the time-series from all voxels in the brain. Fisher tests, Z-transforms, and/or a time-series across a brain atlas can be generated, indicating the overall resting state for each voxel. ROI resting state models can be generated by using the DPABI toolbox by The R-fMRI Network, which can be found at http://rfmri.org/dpabi. As noted above, the ability to develop resting state models using information concerning task related activation of voxels can assist with removal of artifacts resulting from the challenges of a patient maintaining a true resting state during imaging. In many embodiments, however, resting state models are built using only data obtained while a patient is not receiving stimuli.

Resting state models can be used to identify neural circuit pathways that correspond to biotype classifications. In many embodiments, specific patterns of reactivity and connectivity can be used to classify the presence of a specific complex in the observed data. In the context of MRI data the specific complex network classifications can be referred to as biotype classifications, and medication information to treat a given reactivity imbalance can be issued using the image processing system. An example of biotype classification is discussed below.

Biotype Classification

Neural circuit pathway circuits revealed by image processing systems in accordance with various embodiments of the invention can be used to automatically identify and/or classify the presence of complex networks that can be referred to as biotypes. In numerous embodiments, machine learning is used to automatically identify and/or perform biotype classification based upon observed resting state neural pathway circuits. In some embodiments, a support vector machine is used to automatically perform biotype classification. In several embodiments, convolutional neural networks are used to perform biotype classification. A database can be used to train machine learning systems to identify and classify specific biotypes based on observed neural activation and connectivity. In many embodiments, the database is made of MRI image data annotated with complex network classifications, and/or any other type of training data can be used as appropriate to the requirements of a given application. Data in the database can be collected using standardized data collection procedures, including, but not limited to, standardized stimuli order, standardized stimuli time, standardized image processing, and/or any other standardization technique as appropriate to the requirements of a given application.

Biotype classifications can be assigned by analyzing the connectivity and reactivity between regions of the brain. In many embodiments, resting state models are used to assign biotype classifications. Resting state models can contain a set of numbers representing the strength of connection between regions of the brain. Regions of the brain can be associated with various neural circuits. In numerous embodiments, approximately 50 regions are selected for analysis, however a larger or smaller number of regions can be used in accordance with the requirements of a given application. The average strength of the connections over the selected regions are compared to baseline measurements. Based on the average strength of the connections, a determination can be made as to whether or not the neural circuitry is behaving normally or abnormally. In a variety of embodiments, abnormality is determined using a threshold. The threshold can be a specific strength, a predefined number of standard deviations from the norm, and/or any other criterion as appropriate to the requirements of a given application.

Normal and/or abnormal circuits can be used to assign at least one biotype. In many embodiments, assigning biotype classifications using abnormal circuits is performed using a heuristic. In some embodiments, a ranking system is used. In a variety of embodiments, a machine learning algorithm is used. The machine learning algorithm can learn how to weight the importance of specific regions when determining how to assign biotypes. In a number of embodiments, a profile approach is utilized. A profile approach can include matching a patient's observed neural circuit pathways to a database of known neural circuit pathway profiles. A patient may be assigned one or more biotypes. In many embodiments, patients neural circuit pathways can appropriately be classified as an amalgam of biotype classifications. In some embodiments, the image processing system provides the biotype classifications that a patient's resting state neural circuit pathways most closely matches. Provision of biotype classifications can include an indicator of fit, indicating how closely the patient matches a given biotype. The indicator of fit can be a percentage, a statistical estimate, or any other indicator in accordance with the requirements of a given application.

Figure 11:
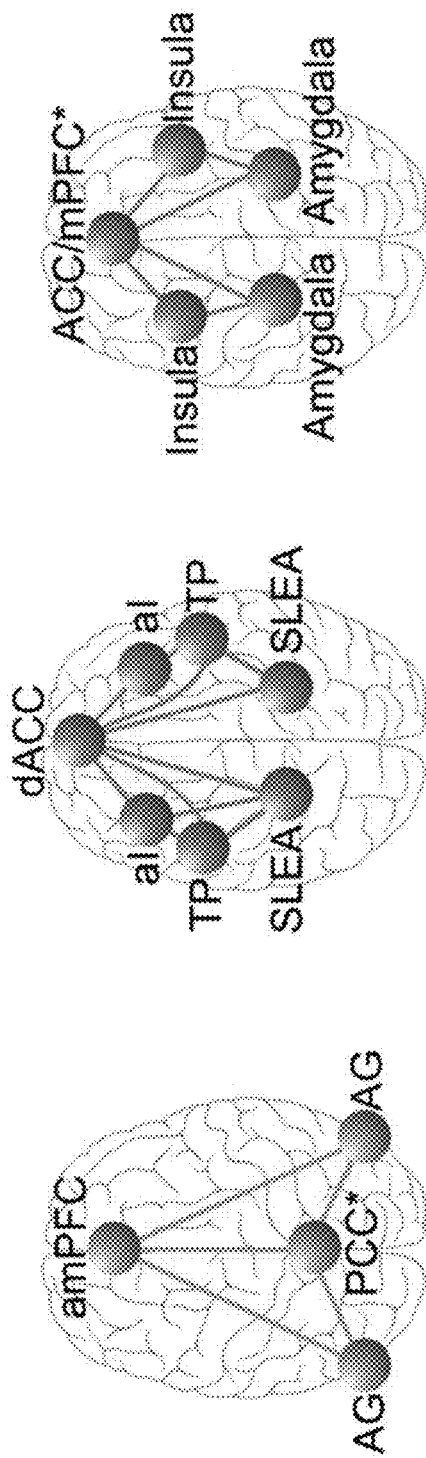
FIG. 11 is a graphic illustrating several neural circuit pathways in accordance with an embodiment of the invention.
Figure 12:
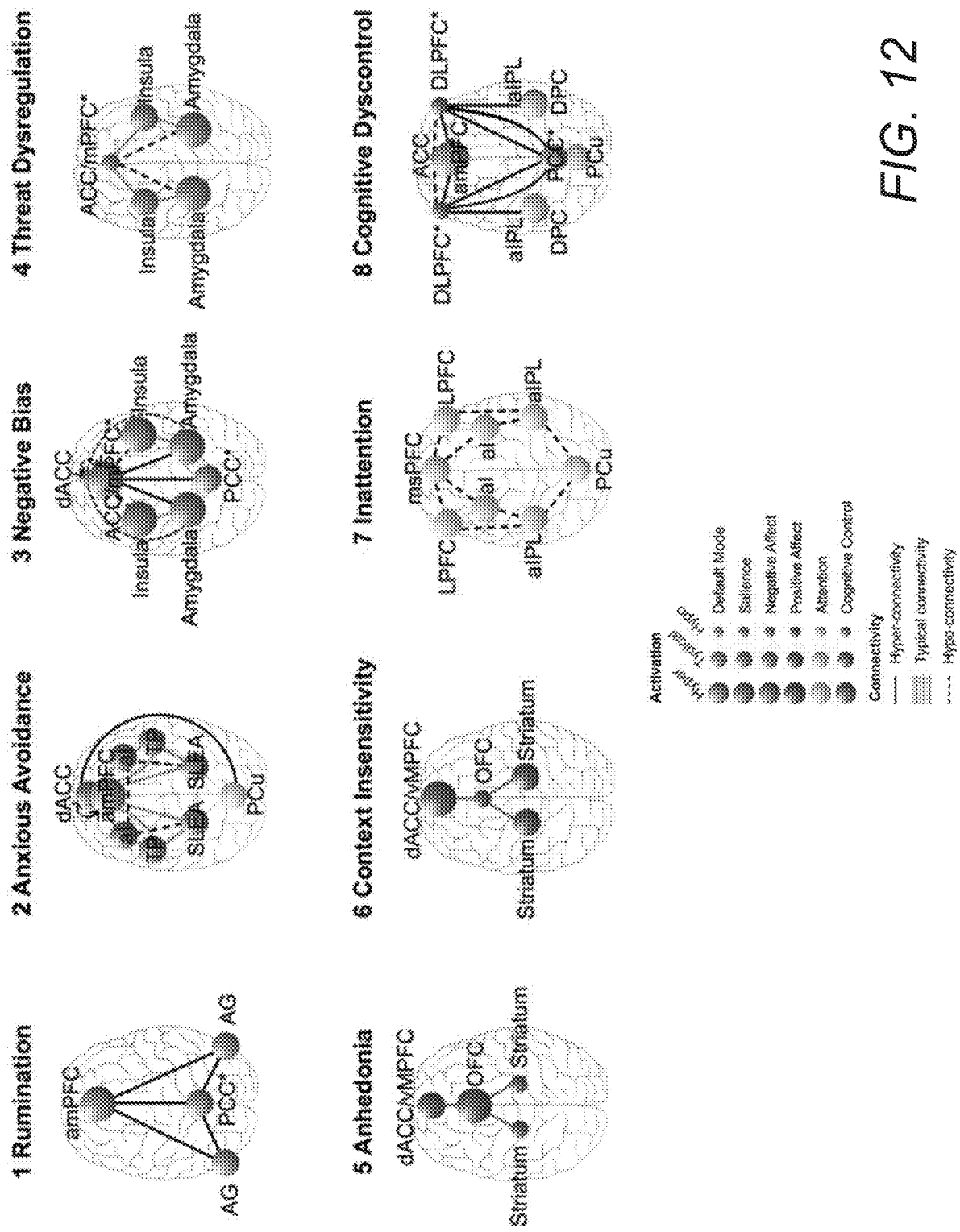
FIG. 12 conceptually illustrates several biotype neural circuit pathways in accordance with an embodiment of the invention.

Connections between various regions in the brain that are responsible for the brain performing a set of different physiological and/or psychological functions can be defined as neural circuit pathways. Neural circuit pathways can be mapped and stored in a taxonomy, and/or brain atlas. Turning now to FIG. 11, a set of example neural circuit pathways are illustrated in accordance with an embodiment of the invention. Deviations in reactivity in specific regions, and/or connectivity can disrupt the normal function of the neural circuit pathways. Hypo, typical, and hyper activity and/or connectivity states can be correlated to specific neurological issues that can be expressed as mental disorders. Turning now to FIG. 12, a chart illustrating the interplay between connectivity and reactivity in accordance with an embodiment of the invention is illustrated. Brain images showing the neural circuitry for the default mode, salience, negative affect, positive affect, attention, and cognitive control are illustrated, as well as example conditions (rumination, anxious avoidance, negative bias, threat dysregulation, anhedonia, context insensitivity, inattention, and cognitive dyscontrol) and their respective abnormal connectivity and reactivity are illustrated. While specific neural circuit pathways are illustrated in FIG. 12, numerous neural circuit pathways exist as complex networks within the brain and can be identified and/or assigned in accordance with the requirements of a given application.

Figure 13:
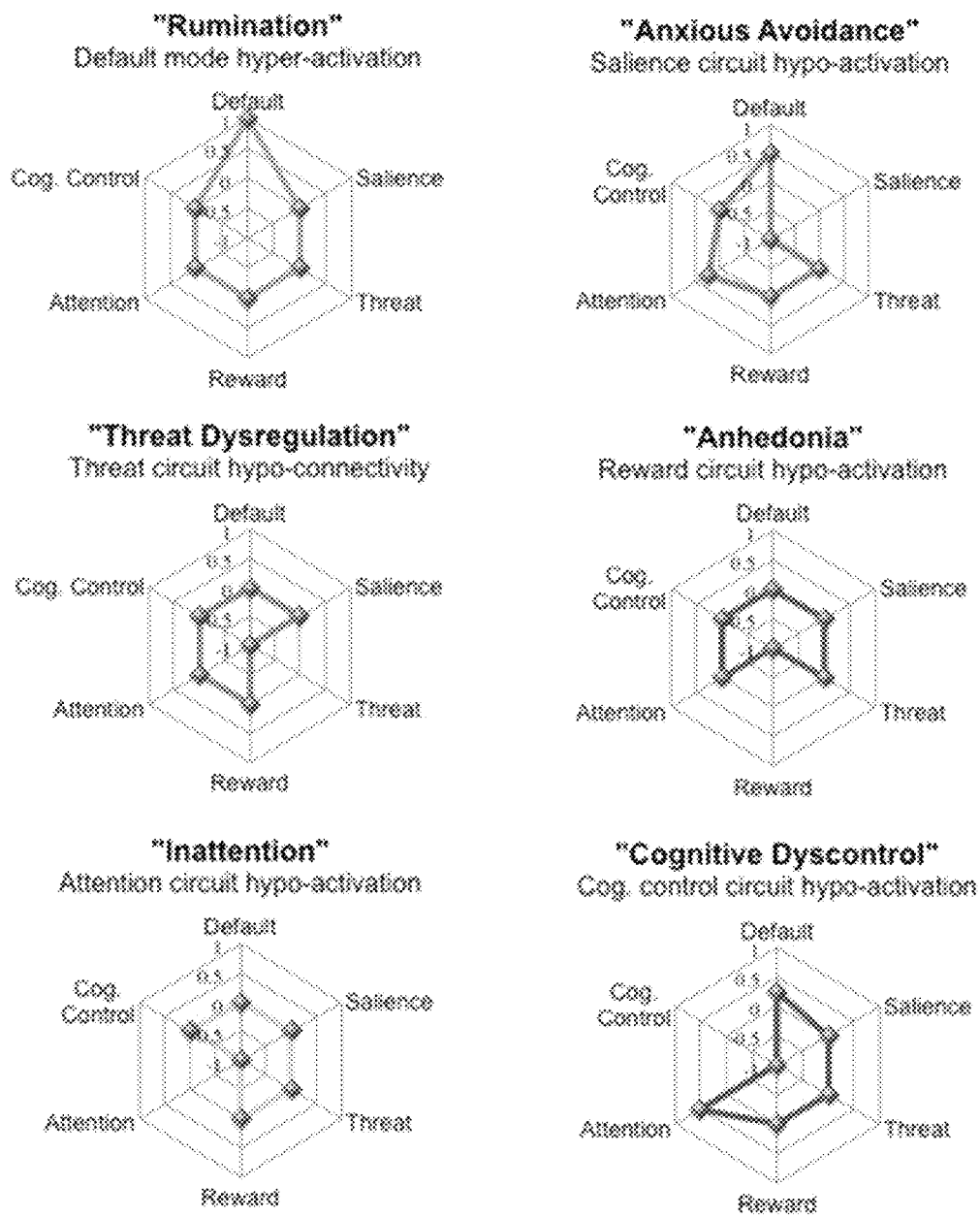
FIG. 13 is an illustration of various biotypes in accordance with an embodiment of the invention.
Figure 15A:
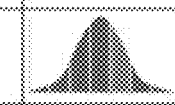

Image processing systems can generate image data representing a patient's brain to produce similar outputs using reactivity and connectivity models. Patient biotype can further be displayed as a radar plot as illustrated in FIG. 13. In many embodiments, scores can be generated that represent the various connections and reactions in neural tissue. In a variety of embodiments, scores can be generated which represent the various circuits that cause particular symptoms. In numerous embodiments, data, such as scores, obtained images, processed images, biotype classifications, and/or any other type of data collected or generated by image processing systems can be provided to the user. In a variety of embodiments, data is provided via a user interface device. However, any number of devices and methods can be used to provide data to a user in accordance with a given application. Turning now to FIGS. 14, 15A, 15B, and 15C, scoring sheets in accordance with an embodiment of the invention are illustrated. In some embodiments, scores can be accompanied by a description of the particular biotype. In many embodiments, score reports and biotype assignment are automatically performed by the image detection system based on the connectivity and reactivity data. In numerous embodiments, only a resting state fMRI is needed to assign biotypes. Based on assigned biotypes, specific drugs and/or drug classes can be recommended to regulate dysfunction caused by the abnormal neural circuitry. Methods for assigning drugs are described below.

Assigning Drugs Based on Biotype

Figure 16:
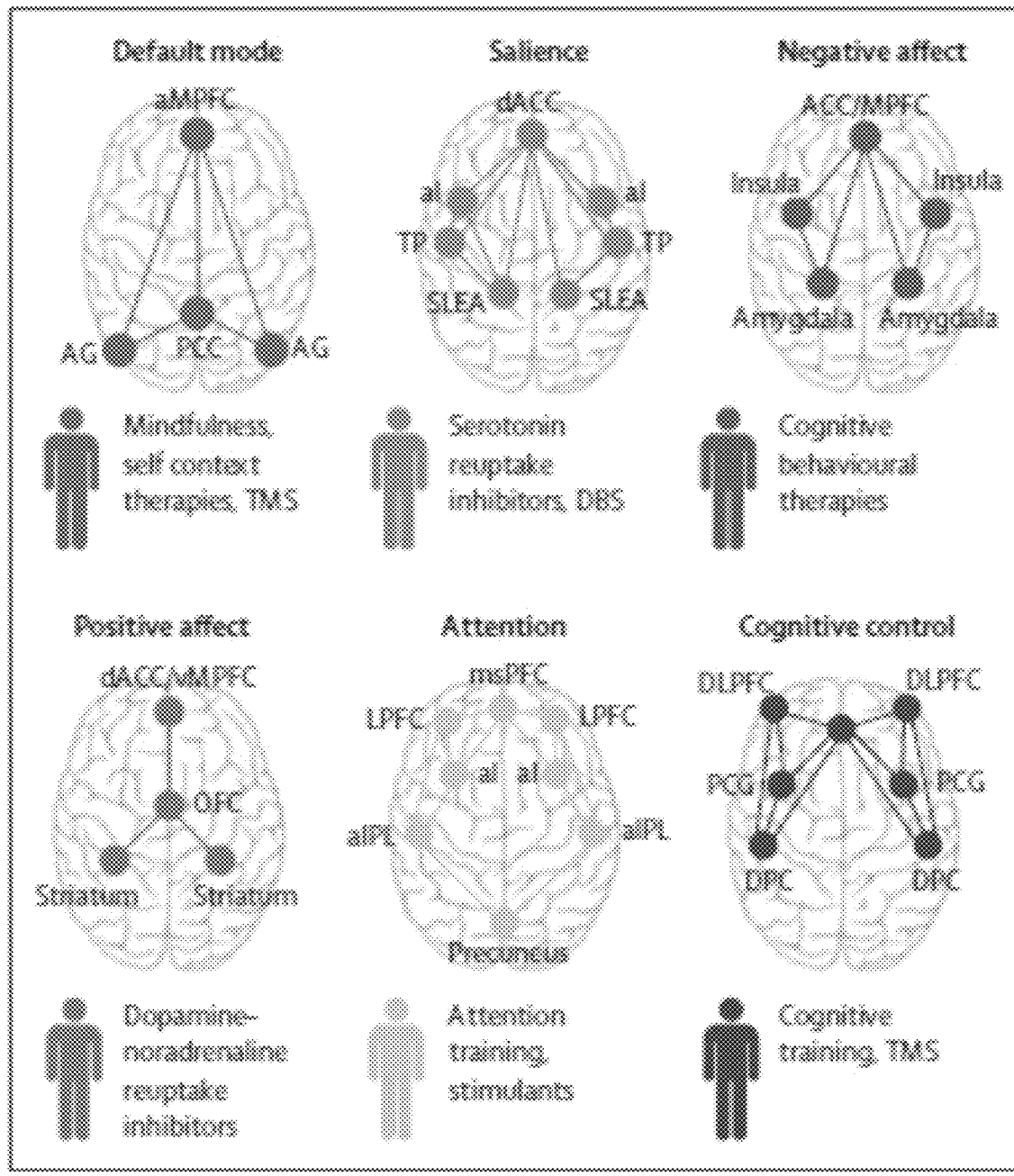
FIG. 16 is an illustration of various neural circuit pathways in accordance with an embodiment of the invention.

In many embodiments, specific complex networks within the brain (i.e. biotype classifications) as identified by the image processing system can be used to assign drugs to remediate the patient. Different drugs and drug classes affect different chemical issues within the brain. By identifying the abnormal circuitry, and how it is behaving abnormally, specific drugs therapies and mental health therapeutic techniques can be recommended in order to target the specific neural circuit pathways likely responsible for particular behavioral tendencies. Turning now to FIG. 16, examples of specific therapies that affect specific neural circuits in accordance with an embodiment of the invention are illustrated. In many embodiments, the image processing system can be integrated with a drug database that describes the function of particular psychoactive medication. Image processing systems can assign drugs based on their physiological effects to remediate the identified abnormal circuitry. In some embodiments, machine learning is utilized to refine the effect of particular therapies on biotypes, and/or amalgams of biotypes. In some embodiments, therapies can be stored in a database, such as, but not limited to, a brain atlas, a taxonomy, a drug database, or any other data structure as appropriate to the requirements of a given application. In many embodiments, therapies stored in a database are associated with at least one biotype and/or neural circuit.

In numerous embodiments, doctors treat patients using methods suggested by image processing systems. In a variety of embodiments, patients are scanned using MRI machines. The resulting scan data can be used by image processing systems to assign biotypes. Biotypes can be associated with one or more treatments and/or drug therapies, which can be administered to the patient. In numerous embodiments, biotypes and/or scores can be used to generate an efficacy metric describing efficacy of a particular drug and/or class of drugs on the particular patient. Efficacy metrics can be used to predict treatment outcomes for patients for particular treatments. In numerous embodiments, efficacy metrics are used to recommend a particular treatment with the highest likelihood of success.

Although the present invention has been described in certain specific aspects, many additional modifications and variations would be apparent to those skilled in the art. In particular, any of the various processes described above can be performed in alternative sequences in order to achieve similar results in a manner that is more appropriate to the requirements of a specific application. It is therefore to be understood that the present invention can be practiced otherwise than specifically described without departing from the scope and spirit of the present invention. Thus, embodiments of the present invention should be considered in all respects as illustrative and not restrictive.

What is claimed is:

1. A method for recommending personalized treatment protocols for mental health conditions, comprising:
obtaining a functional scan of a patient's brain;
classifying the patient's brain with a biotype using a neurological model, where the classification is based upon whether each brain network of a plurality of brain networks is hyper active, typically active, or hypo active, and where the plurality of brain networks comprises: default mode, salience, negative affect, positive affect, attention, and cognitive control networks;
selecting a treatment protocol from a database based on the biotype, where the database comprises associations between treatment protocols and biotypes; and
recommending the selected treatment protocol for treatment of a mental health condition of the patient.

2. The method of claim 1, wherein the selected treatment protocol is a drug.

3. The method of claim 1, wherein the selected treatment protocol is a behavioral therapy.

4. The method of claim 1, wherein the selected treatment protocol is a neuromodulation therapy.

5. The method of claim 1, further comprising:
classifying the patient's brain with a second biotype using the neurological model; and
selecting the treatment protocol from the database based on both the biotype and the second biotype.

6. The method of claim 1, further comprising:
calculating an efficacy metric reflecting an estimated likelihood of success of application of the selected treatment protocol to the patient; and
providing the efficacy metric.

7. The method of claim 1, wherein the functional scan of the patient's brain is a functional magnetic resonance imaging scan.

8. The method of claim 1, further comprising providing a visualization of the biotype, where the visualization indicates relative connectivity in a plurality of neural circuits of the brain.

9. The method of claim 8, wherein neural circuits in the plurality of neural circuits are selected from the group consisting of: default mode; salience; negative affect; positive affect; attention; and cognitive control.

10. The method of claim 1, wherein the treatment protocol comprises a plurality of treatment modalities.

11. A personalized mental health treatment recommendation system, comprising:
a processor; and
a memory, the memory storing an application configuring the processor to:
obtain a functional scan of a patient's brain;
classify the patient's brain with a biotype using a neurological model, where the classification is based upon whether each brain network of a plurality of brain networks is hyper active, typically active, or hypo active, and where the plurality of brain networks comprises: default mode, salience, negative affect, positive affect, attention, and cognitive control networks;;
select a treatment protocol from a database based on the biotype, where the database comprises associations between treatment protocols and biotypes; and
recommend the selected treatment protocol for treatment of a mental health condition of the patient.

12. The system of claim 11, wherein the selected treatment protocol is a drug.

13. The system of claim 11, wherein the selected treatment protocol is a behavioral therapy.

14. The system of claim 11, wherein the selected treatment protocol is a neuromodulation therapy.

15. The system of claim 11, wherein the application further configures the processor to:
classify the patient's brain with a second biotype using the neurological model; and
select the treatment protocol from the database based on both the biotype and the second biotype.

16. The system of claim 11, wherein the application further configures the processor to:
calculate an efficacy metric reflecting an estimated likelihood of success of application of the selected treatment protocol to the patient; and
provide the efficacy metric.

17. The system of claim 11, wherein the functional scan of the patient's brain is a functional magnetic resonance imaging scan.

18. The system of claim 11, wherein the application further configures the processor to provide a visualization of the biotype, where the visualization indicates relative connectivity in a plurality of neural circuits of the brain.

19. The system of claim 18, wherein neural circuits in the plurality of neural circuits are selected from the group consisting of: default mode; salience; negative affect; positive affect; attention; and cognitive control.

20. The system of claim 11, wherein the treatment protocol comprises a plurality of treatment modalities.

* * * * *